United States Patent [19]
Liskay et al.

[11] Patent Number: 5,922,855
[45] Date of Patent: Jul. 13, 1999

[54] MAMMALIAN DNA MISMATCH REPAIR GENES MLH1 AND PMS1

[75] Inventors: Robert M. Liskay, Lake Oswego; C. Eric Bronner; Sean M. Baker, both of Portland, all of Oreg.; Roni J. Bollag, Martinez, Ga.; Richard D. Kolodner, Jamaica Plain, Mass.

[73] Assignees: Oregon Health Sciences University, Portland, Oreg.; Dana-Farber Cancer Institute, Boston, Mass.

[21] Appl. No.: 08/209,521

[22] Filed: Mar. 8, 1994

Related U.S. Application Data

[63] Continuation-in-part of application No. 08/168,877, Dec. 17, 1993., abandoned

[51] Int. Cl.⁶ ................................................ C07H 21/04
[52] U.S. Cl. .................. 536/23.5; 536/24.3; 536/24.31; 536/24.33
[58] Field of Search ............................ 435/6, 91.1, 91.2; 536/22.1, 23.5, 24.1, 24.3, 24.33, 24.31

[56] References Cited

PUBLICATIONS

Marsha S. Williamson et al., "Meiotic Gene Conversion Mutants in *Saccharomyces cerevisiae* I. Isolation and Characterization of PMS1–1 and PMS1–2," *Genetics,* Aug., 1985, pp. 609–646.

Gene Levinson et al., "High Frequencies of Short Frameshifts in Poly–CA/TG Tandem Repeats Borne by Bacteriophage M13 in *Escherichia coli* K–12," *Nucleic Acids Research,* Jun. 2, 1987, pp. 5323–5337.

S. L. Naylor et al., "Loss of Heterozygosity of Chromosome 3p Markers in Small–Cell Lung Cancer," *Nature,* Oct. 1, 1987, pp. 451–454.

Klaas Kok et al., "Deletion of a DNA Sequence at the Chromosomal Region 3p21 in all Major Types of Lung Cancer," *Nature,* Dec. 10, 1987, pp. 578–581.

Douglas K. Bishop et al., "Specificity of Mismatch Repair Following Transformation of *Saccharomyces cerevisiae* with Heteroduplex Plasmid DNA," *Proc. Natl. Acad. Sci. USA,* May 1989, pp. 3713–3717.

Stanley Fields et al., "A Novel Genetic System to Detect Protein–Protein Interactions," *Nature,* Jul. 20, 1989, pp. 245–246.

John A. Mankovich et al., "Nucleotide Sequence of the *Salmonella typhimurium* mutL Gene Required for Mismatch Repair: Homology of MutL to HexB of *Streptococcus pneumoniae* and to PMS1 of the Yeast *Sacchaomyces cerevisiae,"Journal of Bacteriology,* Oct. 1989, pp. 5325–5331.

Marc Prudhomme et al., "Nucleotide Sequence of the *Streptococcus pneumoniae* hexB Mismatch Repair Gene: Homology of HexB to MutL of *Salmonella typhimurium* and to PMS1 of *Saccharomyces cerevisiae,* " *Journal of Bacteriology,* Oct 1989, pp. 5332–5338.

Wilfried Kramer et al., "Cloning and Nucleotide Sequence of DNA Mismatch Repair Gene PMS1 from *Saccharomyces cerevisiae*: Homology of PMS1 to Procaryotic MutL and HexB," *Journal of Bacteriology,* Oct 1989, pp. 5339–5346.

Iqbal Unnisa Ali et al., "Presence of Two Members of c–erbA Receptor Gene Family (c–erbAβ and c–erbA2) in Smallest Region of Somatic Homozygosity on Chromosome 3p21–p25 in Human Breast Carcinoma," *Journal of the National Cancer Institute,* Dec. 6, 1989, pp. 1815–1820.

Peter Lichter et al., "High–Resolution Mapping of Human Chromosome 11 by in Situ Hybridization with Cosmid Clones," *Science,* Jan. 5, 1990, pp. 64–69.

Paul Modrich, "Mechanisms and Biological Effects of Mismatch Repair," *Annu. Rev. Genet.,* 1991, pp. 229–253.

Stephen J. Elledge et al., "λYES: A Multifunctional cDNA Expression Vector for the Isolation of Genes by Complementation of Yeast and *Escherichia Coli* Mutations," *Proc. Natl. Acad. Sci. USA,* Mar. 1991, pp. 1731–1735.

Ann L. Boyle et al., "Rapid Physical Mapping of Cloned DNA on Banded Mouse Chromosomes by Fluorescence in Situ Hybridization," *Genomics,* Aug. 19, 1991, pp. 106–115.

Farida Latif et al., "Chromosome 3p Deletions in Head and Neck Carcinomas: Statistical Ascertainment of Allelic Loss[1]," Jan. 8, 1992, pp. 1451–1456.

Robert A.G. Rennan et al., "Isolation and Characterization of Two *Saccharomyces cervisiae* Genes Encoding Homologs of the Bacterial HexA and MutS Mismatch Repair Proteins," *Genetics,* Dec. 1992, pp. 963–973.

(List continued on next page.)

*Primary Examiner*—Kenneth R. Horlick
*Attorney, Agent, or Firm*—Kolisch, Hartwell, Dickinson, McCormack & Heuser

[57] ABSTRACT

We have discovered two human genes, hMLH1 and hPMS1, each of which apparently encodes for a protein involved in DNA mismatch repair. The hMLH1 gene encodes for a protein which is homologous to the bacterial DNA mismatch repair protein MutL, and is located on human chromosome 3p21.3–23. We believe that mutations in the hMLH1 gene cause hereditary non-polyposis colon cancer (HNPCC) in some individuals based upon the similarity of the hMLH1 gene product to the yeast DNA mismatch repair protein MLH1, the coincident location of the hMLH1 gene and the HNPCC locus on chromosome 3, and hMLH1 missense mutations in affected individuals from a chromosome 3-linked HNPCC family. The human hPMS1 gene is homologous to the yeast DNA mismatch repair gene PMS1, and is located on human chromosome 7q. We believe that the hPMS1 gene is a strong candidate for HNPCC testing because the yeast proteins MLH1 and PMS1 have been shown to be involved in the same DNA repair pathway and because hMLH1 and hMSH2 have both been implicated in HNPCC families. The most immediate use for hMLH1 and hPMS1 will be in screening tests on individuals who are members of families which exhibit high frequencies of early onset cancer. We have also isolated and sequenced mouse MLH1 and PMS1 genes. We have produced chimeric mice with a mutant form of the PMS1 gene that will enable us to derive mice that are heterozygous or homozygous for mutation in mPMS1. These mice will be useful for cancer research. We have also produced and isolated antibodies directed to hPMS1 which are useful in assays to detect the presence of protein in tumor samples.

3 Claims, 17 Drawing Sheets

OTHER PUBLICATIONS

Robert A. G. Reenan et al., "Characterization of Insertion Mutations in the *Saccharomyces cerevisiae* MSH1 and MSH2 Genes: Evidence for Seperate Mitochondrial and Nuclear Functions," *Genetics,* Dec. 1992, pp. 975–985.

M.F. Lyon et al., "Mouse Chromosome Atlas," Jan. 20, 1993.

Henry T. Lynch et al., "Genetics, Natural History, Tumor Spectrum, and Pathology of Hereditary Nonpolyposis Colorectal Cancer: An Updated Review," *Gastroenterology,* May 1993, pp. 1535–1549.

Jean Marx, "New Colon Cancer Gene Discovered," *Science,* May 7, 1993, pp. 751–752.

Päivi Peltomäki et al., "Genetic Mapping of a Locus Predisposing to Human Colorectal Cancer," *Science,* May 7, 1993, p. 810–819.

Yurij Ionov et al., "Ubiquitous Somatic Mutations in Simple Repeated Sequences Reveal a New Mechanism for Colonic Carcinogenesis," *Nature,* Jun. 10, 1993, pp. 558–561.

Thomas A. Kunkel, "Slippery DNA and Diseases," *Nature,* Sep. 16, 1993, pp. 274–276.

Micheline Strand et al., "Destabilization of Tracts of Simple Repetitive DNA in Yeast by Mutations Affecting DNA Mismatch Repair," *Nature,* Sep. 16, 1993, pp. 274–276.

Hye–Jung Han et al., "Genetic Instability in Pancreatic Cancer and Poorly Differentiated Type of Gastric Cancer," *Cancer Research,* Nov. 1, 1993, pp. 5087–5089.

John I. Risinger et al., "Genetic Instability of Microsatellites in Encometrial Carcinoma," *Cancer Research,* Nov. 1, 1993, pp. 5100–5103.

Annika Lindblom et al., "Genetic Mapping of a Second Locus Predisposing to a Hereditary Non–Polyposis Colon Cancer," *Nature Genetics,* Nov. 1993, pp. 279–282.

Richard Fishel et al., "The Human Mutator Gene Homolog MSH2 and Its Association with Hereditary Nonpolyposis Colon Cancer," *Cell,* Dec. 3, 1993, pp. 1027–1038.

Fredrick S. Leach et al., "Mutations of a mutS Homolog in Hereditary Nonpolyposis Colorectal Cancer," *Cell,* Dec. 17, 1993, pp. 1215–1225.

Ramon Parsons et al., "Hypermutability and Mismatch Repair Deficiency in RER+ Tumor Cells," *Cell,* Dec. 17, 1993, pp. 1227–1236.

Steven M. Powell et al., "Molecular Diagnosis of Familial Adenomatous Polyposis," *The New England Journal of Medicine,* Dec. 30, 1993, pp. 1982–1987.

Thomas A. Prolla et al., "Dual Requirement in Yeast DNA Mismatch Repair for MLH1 and PMS1, Two Homologs of the Bacterial mutL Gene," *Molecular and Cellular Biology,* Jan. 1994, pp. 407–415.

C. Eric Bronner et al., "Mutation in the DNA Mismatch Repair Gene Homologue hMLH1 is Associated with Hereditary Non–Polyposis Colon Cancer," *Nature,* Mar. 17, 1994, pp. 258–261.

Borts et al., *Genetics* 124:573–584, 1990.

Kramer et al., *Molecular and Cellular Biol.* 9(10): 4432–4440, 1989.

```
                                               1         10        20
SALMONELLA   - MutL                       MPIQVLPPQLANQIAAGEVVERPASVVK
                                           *  **  **********  ******  *
STREPTOCOCCUS - HexB                      MSHIIELPEMLANQIAAGEVIERPASVCK
                                                    *   *  **      *
SACCHAROMYCES - Pms1   MFHHIENLLIETEKRCKQKEQRYIPVKYLFSHTQIHQINDIDVHRITSGQVITDLTTAVK
                       1        10        20        30        40        50        60

40        50        60        70        80
       MutL   ELVENSLDAGATRVDIDIERGGAKLIRIRDNGCGIKKEELALALARHATSKIASLDDLEA
              *****  ***  *  **    * ***  **   *  ***  *******   **
       HexB   ELVENAIDAGSSQIIIEIEEAGLKKVQITDNGHGIAHDEVELALRRHATSKIKNQADLFR
              *** * ****   ** *       **     *** **     *    * ****     *
       Pms1   ELVDNSIDANANQIEIIFKDYGLESIECSDNGDGIDPSNYEFLALKHYTSKIAKFQDVAK
                     70        80        90        100       110       120

100       110       120       130       140
       MutL   IISLGFRGEALASISSVSRLTLTSRTAEQAEAWQAYAEGRDMDVTVKPAAHPVGTTLEVL
              *  ********  **  ***   ***             * **   *   ****     *
       HexB   IRTLGFRGEALPSIASVSVLTLLTAVDGASHGTKLVARGGEVE.EVIPATSPVGTKVCVE
              **********    *     *    *        *    *            **  * *
       Pms1   VQTLGFRGEALSSLCGIAKLSVITTTSPPKADKELYDMVGHIT.SKTTTSRNKGTTVLVS
                          130       140       150       160       170

160       170       180       190       200
       MutL   DLFYNTPARRK.FMRTEKTEFNHIDEIIRRIALARFDVTLNLSHNGKLVRQYRAVAKDGQ
              ***  *****  *       *  *     **   *           *          *  *
       HexB   DLFFNTPARLK.YMKSQQAELSHIIDIVNRLGLAHPEISFSLISDGKEMTR...TAGTGQ
              **  * ** **  *                  *             **    **
       Pms1   QLFHNLPVRQKEFSKTFKRQFTKCLTVIQGYAIINAAIKFSVWNITPKGKKNLILSTMRN
                        190       200       210       220       230

220       230       240       250       260
       MutL   KERRLGAICGTPFLEQALAIEWQHGDLTLRGWVADPNHTTTALTEIQYCYVNGRMMRDRL
                     *    *      **          *   *    *  *          ***    *
       HexB   LRQAIAGIYGLVSAKKMIEIENSDLDFEISGFVSLPELTRANRHYISL.FINGRYIKNFL
                    *  *        **     *                 *                 *
       Pms1   SSMRKN.ISSVFGAGGMRGELEVDLVLDLNPFKNRMLGKYTDDPDFLDLDYKIRVKGYIS
                      250       260       270       280       290

280                                   290       300
       MutL   INHAIRQACEDKLGA.........................DQQPAFVLYLEIDPHQVDV
                  **  **                                  *  *        *  **
       HexB   LNRAILDGFGSKLMV.........................GRFPLAVIHIHIDPYLADV
                 *                                            **       * **
       Pms1   QNSFGCGRNSKDRQFIYVNKRPVEYSTLLKCCNEVYKTFNNVQFPAVFLNLELPMSLIDV
                   310       320       330       340       350

310       320       330       340       350       360
       MutL   NVHPAKHEVRFHQSRLVHDFIYQGVLSVLQQQTETALPLEEIAPAPRHVQENRIAAGRNH
              ****  * ***          ***   **   **       *                    *
       HexB   NVHPTKQEVRISKEKELMTLVSEAIANSLKEQTLIPDALENLAKSTVRNREKVEQTILPL
              **  *            *                         *           *
       Pms1   NVTPDKRVILLHNERAVID.IFKTTLSDYYNRQELALPKRMCSQSEQQAQKRLKTEVFDD
                        370       380       390       400       410

450       460       470       480       490       500
       HexB   SFPELEFFGQMHGTYLFA....QGRDGLYIIDQHAAQERVKYEEYRESIGNVDQSQQQLL
                *  *  **                *  ****   *     *                  * *
       Pms1   DFKKMEVVGQFNLGFIIVTRKVDNKSDLFIVDQHASDEKYNFETLQAVTVF...KSQKLI
                        710       720       730       740       750

510       520       530       540       550       560
       HexB   VPYIFEFPADDALRLKERMPLLEEVGVFLAEYGENQFILREHPIWMAEEEIESGIYEMCD
               *  *      **  *      *  *  *   *    *   *
       Pms1   IPQPVELSVIDELVVLDNLPVFEKNGFKLKIDEEEEFGSRVKLLSLPTSKQTLFDLGDFN
                        760       770       780       790       800       810

570                 580       590       600       610
       HexB   MLLLTKEVSIKKYRAELA........IMMSCKRSIKANHRIDDHSARQLLYQLSQCDNPY
                   *   *    **              *  *     *            **   **  *
       Pms1   ELIHLIKEDGGLRRDNIRCSKIRSMFAMRACRSSIMIGKPLNKKTMTRVVHNLSELDKPW
                        820       830       840       850       860       870

620
       HexB   NCPHGRPVLVHFT
              ******   *
       Pms1   NCPHGRPTMRHLM
                   880       890
```

Figure 2

Human MLH1 cDNA Nucleotide Sequence

```
CTTGGCTCTTCTGGCGCCAAAATGTCGTTCGTGGCAGGGGTTATTCGGCGGCTGGACGAG    60
                   M  S  F  V  A  G  V  I  R  R  L  D  E
ACAGTGGTGAACCGCATCGCGGCGGGGGAAGTTATCCAGCGGCCAGCTAATGCTATCAAA   120
 T  V  V  N  R  I  A  A  G  E  V  I  Q  R  P  A  N  A  I  K
GAGATGATTGAGAACTGTTTAGATGCAAAATCCACAAGTATTCAAGTGATTGTTAAAGAG   180
 E  M  I  E  N  C  L  D  A  K  S  T  S  I  Q  V  I  V  K  E
GGAGGCCTGAAGTTGATTCAGATCCAAGACAATGGCACCGGGATCAGGAAAGAAGATCTG   240
 G  G  L  K  L  I  Q  I  Q  D  N  G  T  G  I  R  K  E  D  L
GATATTGTATGTGAAAGGTTCACTACTAGTAAACTGCAGTCCTTTGAGGATTTAGCCAGT   300
 D  I  V  C  E  R  F  T  T  S  K  L  Q  S  F  E  D  L  A  S
ATTTCTACCTATGGCTTTCGAGGTGAGGCTTTGGCCAGCATAAGCCATGTGGCTCATGTT   360
 I  S  T  Y  G  F  R  G  E  A  L  A  S  I  S  H  V  A  H  V
ACTATTACAACGAAAACAGCTGATGGAAAGTGTGCATACAGAGCAAGTTACTCAGATGGA   420
 T  I  T  T  K  T  A  D  G  K  C  A  Y  R  A  S  Y  S  D  G
AAACTGAAAGCCCCTCCTAAACCATGTGCTGGCAATCAAGGGACCCAGATCACGGTGGAG   480
 K  L  K  A  P  P  K  P  C  A  G  N  Q  G  T  Q  I  T  V  E
GACCTTTTTTACAACATAGCCACGAGGAGAAAAGCTTTAAAAAATCCAAGTGAAGAATAT   540
 D  L  F  Y  N  I  A  T  R  R  K  A  L  K  N  P  S  E  E  Y
GGGAAAATTTTGGAAGTTGTTGGCAGGTATTCAGTACACAATGCAGGCATTAGTTTCTCA   600
 G  K  I  L  E  V  V  G  R  Y  S  V  H  N  A  G  I  S  F  S
GTTAAAAAACAAGGAGAGACAGTAGCTGATGTTAGGACACTACCCAATGCCTCAACCGTG   660
 V  K  K  Q  G  E  T  V  A  D  V  R  T  L  P  N  A  S  T  V
GACAATATTCGCTCCATCTTTGGAAATGCTGTTAGTCGAGAACTGATAGAAATTGGATGT   720
 D  N  I  R  S  I  F  G  N  A  V  S  R  E  L  I  E  I  G  C
GAGGATAAAACCCTAGCCTTCAAAATGAATGGTTACATATCCAATGCAAACTACTCAGTG   780
 E  D  K  T  L  A  F  K  M  N  G  Y  I  S  N  A  N  Y  S  V
AAGAAGTGCATCTTCTTACTCTTCATCAACCATCGTCTGGTAGAATCAACTTCCTTGAGA   840
 K  K  C  I  F  L  L  F  I  N  H  R  L  V  E  S  T  S  L  R
AAAGCCATAGAAACAGTGTATGCAGCCTATTTGCCCAAAAACACACACCCATTCCTGTAC   900
 K  A  I  E  T  V  Y  A  A  Y  L  P  K  N  T  H  P  F  L  Y
CTCAGTTTAGAAATCAGTCCCCAGAATGTGGATGTTAATGTGCACCCCACAAAGCATGAA   960
 L  S  L  E  I  S  P  Q  N  V  D  V  N  V  H  P  T  K  H  E
GTTCACTTCCTGCACGAGGAGAGCATCCTGGAGCGGGTGCAGCAGCACATCGAGAGCAAG  1020
 V  H  F  L  H  E  E  S  I  L  E  R  V  Q  Q  H  I  E  S  K
CTCCTGGGCTCCAATTCCTCCAGGATGTACTTCACCCAGACTTTGCTACCAGGACTTGCT  1080
 L  L  G  S  N  S  S  R  M  Y  F  T  Q  T  L  L  P  G  L  A
GGCCCCTCTGGGGAGATGGTTAAATCCACAACAAGTCTGACCTCGTCTTCTACTTCTGGA  1140
 G  P  S  G  E  M  V  K  S  T  T  S  L  T  S  S  S  T  S  G
AGTAGTGATAAGGTCTATGCCCACCAGATGGTTCGTACAGATTCCCGGGAACAGAAGCTT  1200
 S  S  D  K  V  Y  A  H  Q  M  V  R  T  D  S  R  E  Q  K  L
GATGCATTTCTGCAGCCTCTGAGCAAACCCCTGTCCAGTCAGCCCCAGGCCATTGTCACA  1260
 D  A  F  L  Q  P  L  S  K  P  L  S  S  Q  P  Q  A  I  V  T
```

Figure 3

Human MLH1 cDNA Nucleotide Sequence (cont'd)

```
GAGGATAAGACAGATATTTCTAGTGGCAGGGCTAGGCAGCAAGATGAGGAGATGCTTGAA    1320
 E  D  K  T  D  I  S  S  G  R  A  R  Q  Q  D  E  E  M  L  E
CTCCCAGCCCCTGCTGAAGTGGCTGCCAAAAATCAGAGCTTGGAGGGGGATACAACAAAG    1380
 L  P  A  P  A  E  V  A  A  K  N  Q  S  L  E  G  D  T  T  K
GGGACTTCAGAAATGTCAGAGAAGAGAGGACCTACTTCCAGCAACCCCAGAAAGAGACAT    1440
 G  T  S  E  M  S  E  K  R  G  P  T  S  S  N  P  R  K  R  H
CGGGAAGATTCTGATGTGGAAATGGTGGAAGATGATTCCCGAAAGGAAATGACTGCAGCT    1500
 R  E  D  S  D  V  E  M  V  E  D  D  S  R  K  E  M  T  A  A
TGTACCCCCCGGAGAAGGATCATTAACCTCACTAGTGTTTTGAGTCTCCAGGAAGAAATT    1560
 C  T  P  R  R  R  I  I  N  L  T  S  V  L  S  L  Q  E  E  I
AATGAGCAGGGACATGAGGTTCTCCGGGAGATGTTGCATAACCACTCCTTCGTGGGCTGT    1620
 N  E  Q  G  H  E  V  L  R  E  M  L  H  N  H  S  F  V  G  C
GTGAATCCTCAGTGGGCCTTGGCACAGCATCAAACCAAGTTATACCTTCTCAACACCACC    1680
 V  N  P  Q  W  A  L  A  Q  H  Q  T  K  L  Y  L  L  N  T  T
AAGCTTAGTGAAGAACTGTTCTACCAGATACTCATTTATGATTTTGCCAATTTTGGTGTT    1740
 K  L  S  E  E  L  F  Y  Q  I  L  I  Y  D  F  A  N  F  G  V
CTCAGGTTATCGGAGCCAGCACCGCTCTTTGACCTTGCCATGCTTGCCTTAGATAGTCCA    1800
 L  R  L  S  E  P  A  P  L  F  D  L  A  M  L  A  L  D  S  P
GAGAGTGGCTGGACAGAGGAAGATGGTCCCAAAGAAGGACTTGCTGAATACATTGTTGAG    1860
 E  S  G  W  T  E  E  D  G  P  K  E  G  L  A  E  Y  I  V  E
TTTCTGAAGAAGAAGGCTGAGATGCTTGCAGACTATTTCTCTTTGGAAATTGATGAGGAA    1920
 F  L  K  K  K  A  E  M  L  A  D  Y  F  S  L  E  I  D  E  E
GGGAACCTGATTGGATTACCCCTTCTGATTGACAACTATGTGCCCCCTTTGGAGGGACTG    1980
 G  N  L  I  G  L  P  L  L  I  D  N  Y  V  P  P  L  E  G  L
CCTATCTTCATTCTTCGACTAGCCACTGAGGTGAATTGGGACGAAGAAAAGGAATGTTTT    2040
 P  I  F  I  L  R  L  A  T  E  V  N  W  D  E  E  K  E  C  F
GAAAGCCTCAGTAAAGAATGCGCTATGTTCTATTCCATCCGGAAGCAGTACATATCTGAG    2100
 E  S  L  S  K  E  C  A  M  F  Y  S  I  R  K  Q  Y  I  S  E
GAGTCGACCCTCTCAGGCCAGCAGAGTGAAGTGCCTGGCTCCATTCCAAACTCCTGGAAG    2160
 E  S  T  L  S  G  Q  Q  S  E  V  P  G  S  I  P  N  S  W  K
TGGACTGTGGAACACATTGTCTATAAAGCCTTGCGCTCACACATTCTGCCTCCTAAACAT    2220
 W  T  V  E  H  I  V  Y  K  A  L  R  S  H  I  L  P  P  K  H
TTCACAGAAGATGGAAATATCCTGCAGCTTGCTAACCTGCCTGATCTATACAAAGTCTTT    2280
 F  T  E  D  G  N  I  L  Q  L  A  N  L  P  D  L  Y  K  V  F
GAGAGGTGTTAAATATGGTTATTTATGCACTGTGGGATGTGTTCTTCTTTCTCTGTATTC    2340
 E  R  C
CGATACAAAGTGTTGTATCAAAGTGTGATATACAAAGTGTACCAACATAAGTGTTGGTAG    2400
CACTTAAGACTTATACTTGCCTTCTGATAGTATTCCTTTATACACAGTGGATTGATTATA    2460
AATAAATAGATGTGTCTTAACATA                                        2484
```

Figure 3 (cont'd)

Human MLH1 genomic sequence surrounding exon corresponding to nucleotides 139-228 of the cDNA (UPPERCASE)

```
ttaatgaggcactattgtttgtatttggagtttgttatcattgcttggctcatattaaaatatgta
cattagagtagttgcagactgataaattattttctgtttgatttgccagTTTAGATGCAAAATCCA
CAAGTATTCAAGTGATTGTTAAAGAGGGAGGCCTGAAGTTGATTCAGATCCAAGACAATGGCACCG
GGATCAGGgtaagtaaaacctcaaagtagcaggatgtttgtgcgcttcatggaagagtcaggacct
ttctctgttctggaaactaggcttttgcagatgggattttttcactgaaaaattcaacaccaacaa
taaatatttattgagtacctattatttgcgg
```

Human MLH1 genomic sequence surrounding exon corresponding to nucleotides 229-327 of the cDNA (UPPERCASE)

```
gaattcaaagagatttggaaaatgagtaacatgattatttactcatcttttggtatctaacaAAA
GAAGATCTGGATATTGTATGTGAAAGGKTCACTACTAGTAAACTGCAGTCCTTTGAGGADTTTAGC
CAGTATTTCTACCTATGGCTTTCGAGGTGAGgtaagctaaagattcaagaaatgtktaaaatatcc
tcctgtgatgacattgtytgtcatttgttagtatgtatttctcaacatagataaataaggtttggt
accttttacttgttaaatgtatgcaaatctghgcaaacttaatgadctttaactttcaaagactga
g
```

Figure 4

```
HUMAN  MSFVAGVIRRLDETVVNRIAAGEVIQRHANAIKEMIENCLDAKSISIQVIVKEGGLRLIQIQDNGTGIRKEDLDIVCERFTTSKLQSFEDLASISTYGFR 100
YEAST  MSLR---IKALDASVVNKIAAGEHIISEVNAIKEMMENSIDANAIMDILVKEGGIRVLQITDNGSGINADIFILCERFTTSKLQKEEDISQHQTYGFR 97

HUMAN  GEALASISHVAHVTITTKTADGKCAYHASYSDGHLKAHPKFQAGNQGTIQHIVEDLFYNIATHRKAIKNPSEFYGKIIIEVGRLYSVHNAGHSFEVKIQGET 200
YEAST  GEALASISHVARVTVITKVKEDRCAWNVSJAFGKMLESPKFVAGKDGTTILVEDLFNIPSHLRAIRSHNDEYSKIDIVGRYAIHSKDHGESCKFIDS 197

HUMAN  VADVRTIHNASTVENTFSHGNAVSREHTEI---GQEHKTIAFKMNGYISNAYSVKQI-FLLFINHRLVESTSLRKAIETVAAYLPNTHPFLYTSL 296
YEAST  NYSLSVKHSYTVQHRLHTVENKSVASNLITFHISKVHEINIE-SVDGKVQINFISKKSISLIFETINNRLVTCDILFRALNSVYSNYLPKGFRPHIYLGI 296

HUMAN  EHSRQNVDVNHPTKHEVHFLHEESHLRVQQHIESKHLGSNSSRMYFT------QTILGLAGPSGEMVKST------TSLHSSSTSGSSDIVYA 380
YEAST  VHEAAVDVNHPTKHFREVFEISQDEHEKIANQLHAEISAIDTHFKASSISTNKPESJIHFNDTIESDRNRKSLRQAQVVENSYTTANSQLRKAHRQE 396

HUMAN  HQMVRTISREQHLDAFIQPLSKPLSSQPQAIVTEDKTDISSGRARQQDEEMIEIPAPAEVAAKNQSLHGDTTKGTSEMSEKRGPTSSNHRKHRHR-EHSDV 479
YEAST  NKLVHIHASQAKITSEHSS-HQQFNFEGSSTKRQLSEPKVTNVSHSQEAEKHTLN------HSEQPRDANTINDND--LKDQEKHKQKLQHYKI 481

HUMAN  EMVEDISRKEMTAA-------CTHRRHI-INLTSVLSHQHEINEQGHEVHREMLHHSFVGQHNPQWALA--HQHQTKLMLNTTKLSEELFYQLLIYDFANF 571
YEAST  PSIADDEKNALPISKDGYIRVKEHVNMLTSIKKHREKVDDSIHRELTDIFANLNYMGWDEERRLAIQHDLKIFHIDYGSVCYELFYQGLTDFANF 581

HUMAN  GVLRFISEPAPLFHLAMLAHDSHSGWTEEHGPKEGLAEYIVEFLKKKAEMIADHFSLEIDEEG--------NHIGLPLIIDNYVFHEGLHFILRLATH 663
YEAST  GKINIQSTNVSDLIVLYNHIS-HFDEINDIASKEK---HISKIWDMSSMINEHYSIELVNDHLDNDLKSVRHKSLPLLKGYIHSLVKLFFFYRIGKH 676

HUMAN  VNWDEEKEQFESLSKHCAMFH---SIRKQYISEESTLSGQOSEVPGSIPNSWKWTVEFIVYKALRSHIHFHKHFTEGNILQLANLPDLYKVFERQ 756
YEAST  VDWEDQELDGILRHHALLIHIPDMVPKVDTLDASLSEDEKAQFINRKEHISSLLEHVLFPCIKRRFLAHRHILKH--VVETANLPDLYKVFERQ 769
```

Figure 5

```
human MLH1  affected  VNRIAAGEVIQRPANAIKEMIENCLDAKFTSIQVIVKEGGLKLIQIQDNGTGIRKEDLDIVCER
human MLH1  normal    VNRIAAGEVIQRPANAIKEMIENCLDAKSTSIQVIVKEGGLKLIQIQDNGTGIRKEDLDIVCER
mouse MLH1            ............PANAIKEMIENCLDAKSTNIQVVVKEGGLKLIQIQDNGTGIRKEDLDIVCER  ·
S. cerevisiae MLH1    VNKIAAGEIIISPVNALKEMMENSIDANATMIDILVKEGGIKVLQITDNGSGINKADLPILCER  ·
S. cerevisiae PMS1    VHRITSGQVITDLTTAVKELVDNSIDANANQIEIIFKDYGLESIECSDNGDGIDPSNYEFLALK  ·
E. coli MutL          ANQIAAGEVVERPASVVKELVENSLDAGATRIDIDIERGGAKLIRIRDNGCGIKKDELALALAR  ·
S. typhimurium MutL   ANQIAAGEVVERPASVVKELVENSLDAGATRVDIDIERGGAKLIRIRDNGCGIKKEELALALAR  ·
S. pneumoniae HexB    ANQIAAGEVIERPASVCKELVENAIDAGSSQIIEIEEAGLKKVQITDNGHGIAHDEVELALRR  ·
```

Figure 9

Figure 10:
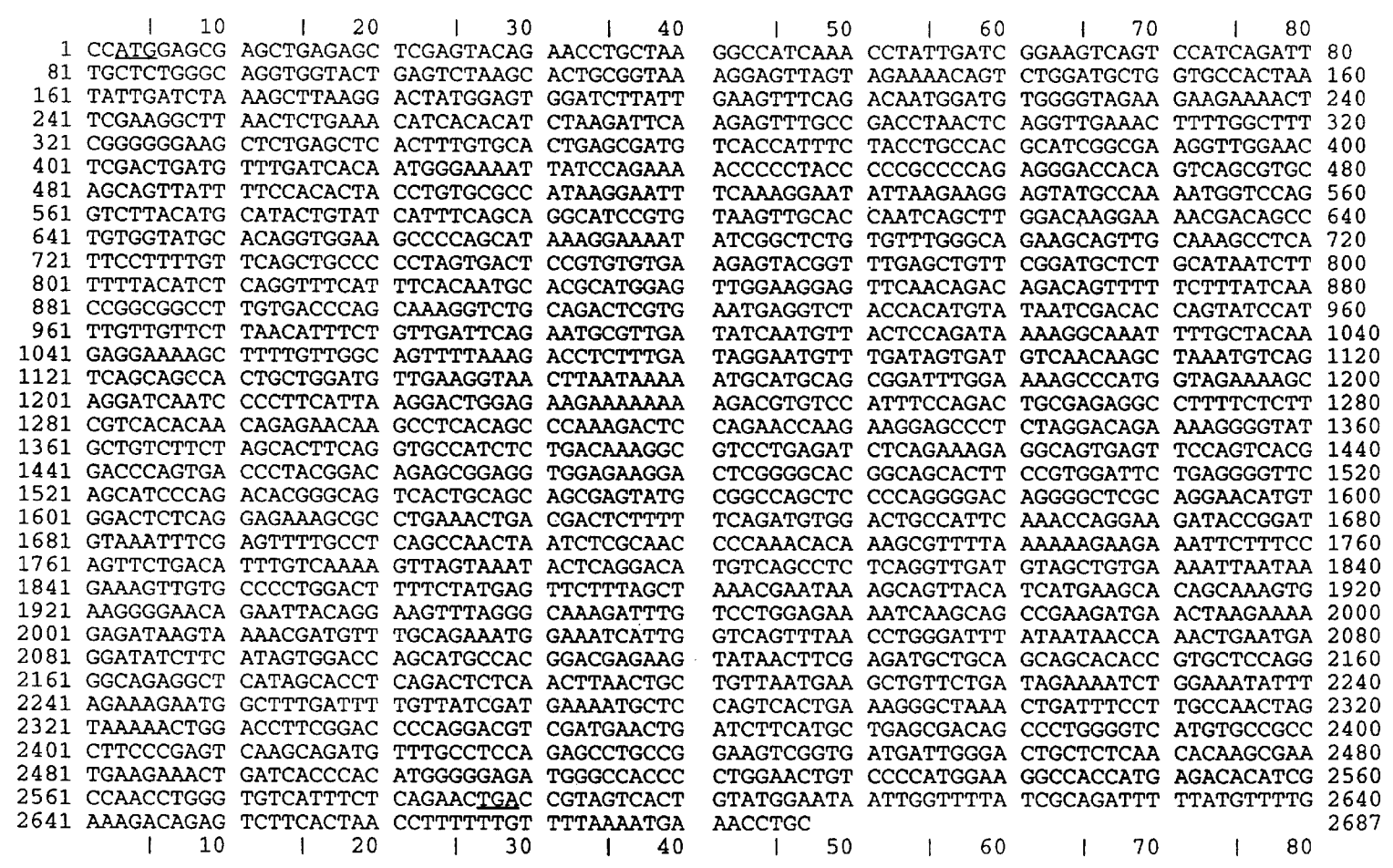

```
          |  10       |  20       |  30       |  40        |  50       |  60       |  70       |  80
   1 CCATGGAGCG AGCTGAGAGC TCGAGTACAG AACCTGCTAA  GGCCATCAAA CCTATTGATC GGAAGTCAGT CCATCAGATT 80
  81 TGCTCTGGGC AGGTGGTACT GAGTCTAAGC ACTGCGGTAA  AGGAGTTAGT AGAAAACAGT CTGGATGCTG GTGCCACTAA 160
 161 TATTGATCTA AAGCTTAAGG ACTATGGAGT GGATCTTATT  GAAGTTTCAG ACAATGGATG TGGGGTAGAA GAAGAAAACT 240
 241 TCGAAGGCTT AACTCTGAAA CATCACACAT CTAAGATTCA  AGAGTTTGCC GACCTAACTC AGGTTGAAAC TTTTGGCTTT 320
 321 CGGGGGGAAG CTCTGAGCTC ACTTTGTGCA CTGAGCGATG  TCACCATTTC TACCTGCCAC GCATCGGCGA AGGTTGGAAC 400
 401 TCGACTGATG TTTGATCACA ATGGGAAAAT TATCCAGAAA  ACCCCCTACC CCCGCCCCAG AGGGACCACA GTCAGCGTGC 480
 481 AGCAGTTATT TTCCACACTA CCTGTGCGCC ATAAGGAATT  TCAAAGGAAT ATTAAGAAGG AGTATGCCAA AATGGTCCAG 560
 561 GTCTTACATG CATACTGTAT CATTTCAGCA GGCATCCGTG  TAAGTTGCAC CAATCAGCTT GGACAAGGAA AACGACAGCC 640
 641 TGTGGTATGC ACAGGTGGAA GCCCCAGCAT AAAGGAAAAT  ATCGGCTCTG TGTTTGGGCA GAAGCAGTTG CAAAGCCTCA 720
 721 TTCCTTTTGT TCAGCTGCCC CCTAGTGACT CCGTGTGTGA  AGAGTACGGT TTGAGCTGTT CGGATGCTCT GCATAATCTT 800
 801 TTTTACATCT CAGGTTTCAT TTCACAATGC ACGCATGGAG  TTGGAAGGAG TTCAACAGAC AGACAGTTTT TCTTTATCAA 880
 881 CCGGCGGCCT TGTGACCCAG CAAAGGTCTG CAGACTCGTG  AATGAGGTCT ACCACATGTA TAATCGACAC CAGTATCCAT 960
 961 TTGTTGTTCT TAACATTTCT GTTGATTCAG AATGCGTTGA  TATCAATGTT ACTCCAGATA AAAGGCAAAT TTTGCTACAA 1040
1041 GAGGAAAAGC TTTTGTTGGC AGTTTTAAAG ACCTCTTTGA  TAGGAATGTT TGATAGTGAT GTCAACAAGC TAAATGTCAG 1120
1121 TCAGCAGCCA CTGCTGGATG TTGAAGGTAA CTTAATAAAA  ATGCATGCAG CGGATTTGGA AAAGCCCATG GTAGAAAAGC 1200
1201 AGGATCAATC CCCTTCATTA AGGACTGGAG AAGAAAAAAA  AGACGTGTCC ATTTCCAGAC TGCGAGAGGC CTTTTCTCTT 1280
1281 CGTCACACAA CAGAGAACAA GCCTCACAGC CCAAAGACTC  CAGAACCAAG AAGGAGCCCT CTAGGACAGA AAAGGGGTAT 1360
1361 GCTGTCTTCT AGCACTTCAG GTGCCATCTC TGACAAAGGC  GTCCTGAGAT CTCAGAAAGA GGCAGTGAGT TCCAGTCACG 1440
1441 GACCCAGTGA CCCTACGGAC AGAGCGGAGG TGGAGAAGGA  CTCGGGGCAC GGCAGCACTT CCGTGGATTC TGAGGGGTTC 1520
1521 AGCATCCCAG ACACGGGCAG TCACTGCAGC AGCGAGTATG  CGGCCAGCTC CCCAGGGGAC AGGGGCTCGC AGGAACATGT 1600
1601 GGACTCTCAG GAGAAAGCGC CTGAAACTGA CGACTCTTTT  TCAGATGTGG ACTGCCATTC AAACCAGGAA GATACCGGAT 1680
1681 GTAAATTTCG AGTTTTGCCT CAGCCAACTA ATCTCGCAAC  CCCAAACACA AAGCGTTTTA AAAAAGAAGA AATTCTTTCC 1760
1761 AGTTCTGACA TTTGTCAAAA GTTAGTAAAT ACTCAGGACA  TGTCAGCCTC TCAGGTTGAT GTAGCTGTGA AAATTAATAA 1840
1841 GAAAGTTGTG CCCCTGGACT TTTCTATGAG TTCTTTAGCT  AAACGAATAA AGCAGTTACA TCATGAAGCA CAGCAAAGTG 1920
1921 AAGGGGAACA GAATTACAGG AAGTTTAGGG CAAAGATTTG  TCCTGGAGAA AATCAAGCAG CCGAAGATGA ACTAAGAAAA 2000
2001 GAGATAAGTA AAACGATGTT TGCAGAAATG GAAATCATTG  GTCAGTTTAA CCTGGGATTT ATAATAACCA AACTGAATGA 2080
2081 GGATATCTTC ATAGTGGACC AGCATGCCAC GGACGAGAAG  TATAACTTCG AGATGCTGCA GCAGCACACC GTGCTCCAGG 2160
2161 GGCAGAGGCT CATAGCACCT CAGACTCTCA ACTTAACTGC  TGTTAATGAA GCTGTTCTGA TAGAAAATCT GGAAATATTT 2240
2241 AGAAAGAATG GCTTTGATTT TGTTATCGAT GAAAATGCTC  CAGTCACTGA AAGGGCTAAA CTGATTTCCT TGCCAACTAG 2320
2321 TAAAAACTGG ACCTTCGGAC CCCAGGACGT CGATGAACTG  ATCTTCATGC TGAGCGACAG CCCTGGGGTC ATGTGCCGCC 2400
2401 CTTCCCGAGT CAAGCAGATG TTTGCCTCCA GAGCCTGCCG  GAAGTCGGTG ATGATTGGGA CTGCTCTCAA CACAAGCGAA 2480
2481 TGAAGAAACT GATCACCCAC ATGGGGGAGA TGGGCCACCC  CTGGAACTGT CCCCATGGAA GGCCACCATG AGACACATCG 2560
2561 CCAACCTGGG TGTCATTTCT CAGAACTGAC CGTAGTCACT  GTATGGAATA ATTGGTTTTA TCGCAGATTT TTATGTTTTG 2640
2641 AAAGACAGAG TCTTCACTAA CCTTTTTTGT TTTAAAATGA  AACCTGC                                     2687
          |  10       |  20       |  30       |  40        |  50       |  60       |  70       |  80
```

```
   1 TTCCGGCCAA TGCTATCAAA GAGATGATAG AAAACTGTTT AGATGCAAAA TCTACAAATA TTCAAGTGTT TGTTAAGGAA   80
  81 GGTGGCCTGA AGCTAATTCA GATCCAAGAC CTTTTGAGGA AATGGCACTG GAATCAGGAA GGAAGATCTG GATATTGTGT GTGAGAGTT  160
 161 CACTACGAGT AAACTGCAGA CTTTGAGGA ACTATTACAA TTTAGCCAGT ATTTCTACCT ATGGCTTTCG TGGTGAGCAT TTGGCAAGCA  240
 241 TAAGTCATGT GGCCCATGTC CCCTCCTAA CCAAAACAGC CCAAACAGC TGATGGGAAA TGTGCGTACA GAGCAAGTTA CTCAGATGA  320
 321 AGCTGCAAG CCCCTCCTAA ACCCTGTGCA GGCAACCAGG GCACCCTGAT CACGGTGGAA GACCTTTTTT ACAACATAAT  400
 401 CACAAGGAGG AAAGCTTTAA AAAATCCAAG TGAAGAGTAC GGAAAAATTT TGGCAGTGT TGGCAGTAT TCAATACACA  480
 481 ATTCAGGCAT TAGTATCTCA GTTAAAAAAC AAGGTGAGAC AGTATCTGAT GTCAGAACAC TGCCCAATGC CACAACCGTG  560
 561 GACAACATTC GCTCCATCTT TGGAAATGCG GTTAGTCGAG AACTGATAGA AGTTGGGTGT GAGGATAAAA CCCTAGCTTT  640
 641 CAAAATGAAT GGCTATATAT CGAATGCAAA GTATTCAGTG AAGAAGTGCA TTTTCCTACT CTTCATCAAC CACCGTCTGG  720
 721 TAGAATCAGC TGCCTTGAGA AAAGCCATTG AAACTGTATA TGCAGCATAC TTGCCAAAAA CACACACCA TTCCTGTACC  800
 801 TCAGTTTGAA ATCAGCCCTC AGAACGTGAC GTCAATGTAC ACCCACCAA GACAGAAGTT CATTTTCTGC ACGAGGAGAG  880
 881 CATTCTGCAG CGTGTGCAGC AGCACATTGA GAGCAAGCTG CTGGGCTCCA ATTCCTCCAG GATGTATTTC ACCCAGACCT  960
 961 TGCTTCCAGG ACTTGCTGGG CCTCTGGGGA GGCAGCTAGA CCCACGACAG GGGTGGCTTC CTCATCCACT AGTGGAAGTG 1040
1041 GCGACAAGGT CTACGCTTAC CAGATGTCGC GTACGGACTC AAGCTTGACG CCTTTCTGCA GCCTGTAAGC 1120
1121 AGCCTGTGC CCAGCCAGCC CCAGGACCCT CGCCCTGTCC GAGGGCCAG ACAGAGGGC TCTCCTGAAA GGGCCACGCG 1200
1201 GGAGGATGAG GAGATGCTTG CTCTCCCAGC CCCCGCTGAA GCAGCTGCTG AGAGTGAGAA CTTGGAGAGG GAATCACTAA 1280
1281 TGGAGACTTC AGACGCAGCC CAGAAAGCGG TGCTTCCGGG AAGGAAATGA CAGTCCAGA AGCTCCAGA AGAGTCATCG GGAGGACTCT 1360
1361 GATGTGAAA TGGTGAAAA TGCTTCCGGG AAGGATTAG TGAGCGGTGC CTACCCAGG TACCTGCTG AGAGGAGATCA TTAACCTCAC 1440
1441 CAGCGTCTTG AGTCTCCCAG AAGAGATTAG TGAGCGGTGC CACAGCACCA CATGAGACTC ACTCCGTAAC CATTCCTTTG 1520
1521 TGGCTGTTCT GAATCCTCAG ACCAGATACT CATTTATGAT TTTGCCAACT GACCAAGCTA TACCTCCTCA GCTCAGTGAA 1600
1601 GAGCTGTTCT CCTGGTTAGA CAGTCCTGAA AGTGGCTGGA CACAGCACCA TTGGTTCCT GAGGTTATCG GAACCAGCGC CACTCCTCGA 1680
1681 CCTGGCCATG CTGGCTTAGA CAGTCCTGAA AGTGGCTGGA GCAGACTATT CAGAGGACGA CGGCCCGAAG AAGGGCTTGC AGTAGTACAT 1760
1761 GTCGAGTTTC TGAAGAGAAG CGATATGTGC CACCTTTTGA GGGACTGCCT CTCTGTGAGA TCGATGAGAA GGGAACCTGA TTGATTACTC 1840
1841 TTCTGATGAC AGCTATGTGC GTCTCAGTAA GTCCTTTGGA GGGACTGCCT ATCTTCATTC TTCGACTGGC CACTGAGGTG AATTGGGTGA 1920
1921 AGAAAAGGAG TGTTTTGAAA AGGCCAGCAG AGTGACATGC CTGGCTCCAC AGAATGTGCT ATGTTTTACT CCATTCGGAA GCAGTATATA CTGGAGAGT 2000
2001 CGACCCCTC AGGCCAGCAG AGTGACATGC CTGGCTCCAC AAGCATTTCA GTCAAAGCCC TGGAAGTGGA CTGTGAAGCA CATTATCTAT 2080
2081 AAAGCCTTCC GCTCACACCT CCTACCTCCG AAGCATTTCA ACAATCATAG CAGAAGATGG CAATGTCCTG CAGCTTGCCA ACCTGCCAGA 2160
2161 TCTATACAAA GTCTTTGAGC GGTGTTAAAT ACAATCATAG CAGAAGATGG CAATGTCCTG CAGCTTGCCA ACCTGCCAGA CGAAGTGTAT 2240
2241 GGTACTAATC TGGAAGCCAC AGAATAGGAC TTAATGTACT AGTGGCTGCA TTTTCAGTGC TCACTATTCT TGTTCTGTAT 2320
2321 CCCAGTATTG GTGCTGCAAC TTAATGTACT TCACCTGTGG AATAAACTCA CGTGTAGTGC AAAAAAGGAA 2400
2401 TTCCTGCAGC CGGGGGATC CACTAGTTCT AGAGCGGCCG AGCTCCAGCT TTTGTTCCCT TTAGTGAGGG 2480
2481 TTAATTTCGA GCTTGGCGTA ATCATGGTCA TAGCTGTTTC TGTGTAAA TTGTTATCCG CTCACAATTC CACACAACAT 2560
2561 ACGAGCCGGA AGCATAA                                                                                2577
```

Figure 13

```
mouse    1  ..........................PANAIKEMIENCLDAKSTNIQVVVKEGGLKLIQIQDNGTGIRKEDLDIVCERFTTSKLQTFEDLASISTYGFR   73
                                      ||||||||||||||||  ||| ||||||||||||||||||||||||||||||||||||| |||||||||||
human    1  MSFVAGVIRRLDETVVNRIAAGEVIQRPANAIKEMIENCLDAKSTSIQVIVKEGGLKLIQIQDNGTGIRKEDLDIVCERFTTSKLQSFEDLASISTYGFR  100

74  GEHLASISHVAHVTITTKTADGKCAYRASYSDGKLQAPPKPCAGNQGTLITVEDLFYNIITRRKALKNPSEEYGKILEVGRYSIHNSGISISVKKQGET  173
            || ||||||||||||||||||||||||||||||||||||||||||||||||||||| |||||||||||||||||||||| |||| ||| ||||||||
       101  GEALASISHVAHVTITTKTADGKCAYRASYSDGKLKAPPKPCAGNQGTQITVEDLFYNIATRRKALKNPSEEYGKILEVGRYSVHNAGISFSVKKQGET  200

174  VSDVRTLPNATTVDNIRSIFGNAVSRELIEVGCEDKTLAFKMNGYISNAKYSVKKCIFLLFINHRLVESAALRKAIETVYAAYLPK-THTHSCTSVZNQP  272
            | |||||||| |||||||||||||||||| ||||||||||||||||||||||||||||||||||||||||   ||||||||||| |
       201  VADVRTLPNASTVDNIRSIFGNAVSRELIEIGCEDKTLAFKMNGYISNANYSVKKCIFLLFINHRLVESTSLRKAIETVYAAYLPKNTHPFLYLSLEISP  300

273  SERDVNVHPTKTEVHFLHEESILQRVQQHIESKLLGSNSSRMVFHPDLASRTCWASGEAARPTTGVASSSTSGSGDKVYAYQMSRTDSRDQKLDAFLQPV  372
            | ||||||||| |||||||||| |||||||||||||||||||  ||                    |  |||||||  |      |||||||||| |
       301  QNVDVNVHPTKHEVHFLHEESILERVQQHIESKLLGSNSSRMYFTQTLLPGLAGPSGEMVKSTTSLTSSSTSGSSDKVYAHQMVRTDSREQKLDAFLQPL  400

373  SSLVPSQPQDPRPVRGARTEGSPERATREDEEMLALPAPAEAAAESENLERESLMETSDAAQKAAPTSSPGSSRKSHREDSDVEMVENASGKEMTAACYP  472
             |  |||||                ||  ||||  || ||                            ||      ||||||||||| ||||| |
       401  SKPLSSQPQA--IVTEDKTDISSGRARQQDEEMLELPAPAEVAAKNQSLEGDTTKGTSEMSEKRGPTSS--NPRKRHREDSDVEMVEDDSRKEMTAACTP  496

473  RRRIINLTSVLSLQEEISERCHETLREILRNHSFVGCVNPQWALAQHQTKLYLLNTTKLSEELFYQILIYDFANFGVLRLSEPAPLFDLAMLAZTVLKVA  572
            |||||||||||||||| |||| ||| ||| |||||||||||||||||||||||||||||||||||||||||||||||||||||||||||||
       497  RRRIINLTSVLSLQEEINEQGHEVLREMLHNHSFVGCVNPQWALAQHQTKLYLLNTTKLSEELFYQILIYDFANFGVLRLSEPAPLFDLAMLA--LDSPE  594

573  GQRTTAR-RRACRVHCRVSEEKRDACRLFSVRSMRREPDZ-----LLFZZQLCATFGGTAYLHSSTGHZGELGEEKECFESLSKECAMFYSIRKQYILEE  666
                 ||    |  |   |  |  |                                                 ||||||||||||||||||||||||
       595  SGWTEEDGPKEGLAEYIVEFLKKKAEMLADYFSLEIDEEGNLIGLPLLIDNYVPPLEGLPIFILRLATEVNWDEEKECFESLSKECAMFYSIRKQYISEE  694

667  STLSGQQSDMPGSTSKPWKWTVEHIIYKAFRSHLLPPKHFTEDGNVLQLANLPDLYKVFERC  728
            |||||||| ||| |||||||||||| |||||||||||||||| |||||||||||||||||
       695  STLSGQQSEVPGSIPNSWKWTVEHIVYKALRSHILPPKHFTEDGNILQLANLPDLYKVFERC  756
```

Figure 14

| | | | | | | | | |
|---|---|---|---|---|---|---|---|---|
| | 10 | 20 | 30 | 40 | 50 | 60 | 70 | 80 |
| 1 | CGGTGAAGGT | CCTGAAGAAT | TTCCAGATTC | CTGAGTATCA | TTGGAGGAGA | CAGATAACCT | GTCGTCAGGT | AACGATGGTG | 80 |
| 81 | TATATGCAAC | AGAAATGGGT | GTTCCTGGAG | ACGGTCTTT | TCCCGAGAGC | GGCACCGCAA | CTCTCCCGCG | GTGACTGTGA | 160 |
| 161 | CTGGAGAGT | CCTGCATCCA | TGGAGCAAAC | GGAAGGCGTG | AGTACAGAAT | GTGCTAAGGC | CATCAAGCCT | ATTGATGGGA | 240 |
| 241 | AGTCAGTCCA | TCAAATTTGT | TCTGGGCAGG | TGATACTCAG | TTTAAGCACC | GCTGTGAAGG | AGTTGATAGA | AAATAGTGTA | 320 |
| 321 | GATGCTGGTG | CTACTACTAT | TGATCTAAGG | CTTAAAGACT | ATGGGGTGA | CCTCATTGAA | GTTTCAGACA | ATGGATGTGG | 400 |
| 401 | GGTAGAAGAA | GAAAACTTTG | AAGGTCTAGC | TCTGAAACAT | CACACATCTA | AGATTCAAGA | GTTTGCCGAC | CTCACGCAGG | 480 |
| 481 | TTGAAACTTT | CGGCTTTCGG | GGGGAAGCTC | TGAGCTCTCT | GTGTGCACTA | AGTGATGTCA | CTATATCTAC | CTGCCACGGG | 560 |
| 561 | TCTGCAAGCG | TTGGGACTCG | ACTGGTGTTT | GACCATAATG | GGAAAATCAC | CCAGAAAACT | CCCTACCCCC | GACCTAAAGG | 640 |
| 641 | AACCACAGTC | AGTGTGCAGC | ACTTATTTTA | TACACTACCC | GTGCGTTACA | AAGAGTTTCA | GAGGAACJ.IT | AAAAAGGAGT | 720 |
| 721 | ATTCCAAAAT | GTGCAGGTC | TTACAGGCGT | ACTGTATCAT | CTCAGCAGGC | GTCCGTGTAA | GCTGCACTAA | TCAGCTCGGA | 800 |
| 801 | CAGGGAAGC | GGCACGCTGT | GGTGTGCACA | AGCGGCACGT | CTGGCATGAA | GGAAAATATC | GGTCTGTGT | TTGCCAGAA | 880 |
| 881 | GCAGTTGCAA | AGCCCTCATTC | CTTTTGTTCA | GCTGCCCCCT | AGTGACGCTG | TGTGTGAAGA | GTACGGCCTG | AGCACTTCAG | 960 |
| 961 | GACGCCACA | AACCTTTTCT | ACGTTTTCGG | GCTTCATTTC | ACAGTGCACG | CACGGCGCCG | GGAGGAGTGC | AACAGACAGG | 1040 |
| 1041 | CAGTTTTTCT | TCATCAATCA | GAGGCCCTGT | GACCCAGCAA | AGGTCTCTAA | GCTTGTCAAT | GAGGTTTATC | ACATGTATAA | 1120 |
| 1121 | CCGGCATCAG | TACCCATTTG | TCGTCCTTAA | CGTTTCCGTT | GACTCAGAAT | GTGTGGATAT | TAATGTAACT | CCAGATAAAA | 1200 |
| 1201 | GGCAAATTCT | ACTACAAGAA | GAGAAGCTAT | TGCTGGCCGT | TTTAAAGACC | TCCTTGATAG | GAATGTTTGA | CAGTGATGCA | 1280 |
| 1281 | AACAAGCTTA | ATGTCAACCA | GCAGCCACTG | CTAGATGTTG | AAGGTAACTT | AGTAAAGTCG | CATACTGCAG | AACTAGAAAA | 1360 |
| 1361 | GCCTGTCCA | GAAAGCAAG | ATAACTCTCC | TTCACTGAGG | AGCACACAAG | ACAGAGACTG | GGTAGCATCC | ATCTCCAGGC | 1440 |
| 1441 | TGAGAGAGG | CTTTTCTCTT | CATCCTACTA | AAGAGATCAA | GTCTAGGGGT | CCAGAGACTC | CTGAACTGAC | ACGGAGTTTT | 1520 |
| 1521 | CCAAGTGAGA | AAAGGGGCGT | GTTATCCTCT | TATCCTTCAG | ACGTCATCTC | TTACAGAGGC | CTCCGTGGCT | CGCAGGACAA | 1600 |
| 1601 | ATTGGTGAGT | CCCACGGACA | GCCCTGGTGA | CTGTATGGAC | AGAGAAAAA | TAGAAAAAGA | CTCAGGGCTC | AGCAGCACCT | 1680 |
| 1681 | CAGCTGGCTC | TGAGGAAGAG | TTCAGCACCC | CAGAAGTGGC | CAGTAGCTTT | AGCAGTGACT | ATAACGTGAG | CTCCCTAGAA | 1760 |
| 1761 | GACACCTT | CTCAGACCAA | CATAAACTGT | GGTGACCTGC | TGCCGTCCTC | CAGGTACAGG | ACAGTCCTTG | AAGCCAGAAG | 1840 |
| 1841 | ACCATGACA | TCAATGCAA | GCTCTACCTC | TAGCTCGTCT | GTCACCCACA | AATGCCAAGC | GCTTCAAGAC | AGAGGAAGAC | 1920 |
| 1921 | CCTCAAATGT | CAACATATCT | CAAAGATTGC | CAGTTCTCTA | GAGCTGAGG | GCAGCTGAGG | TCGATGTAGC | CATAAAAATG | 2000 |
| 2001 | AATAAGAGAT | CGTGCTCCTC | GAGTTCTCTA | GCTAAGCAA | TGAAGCAGTT | ACAGCACCTA | AAGGCGCAGA | ACAAACATGA | 2080 |
| 2081 | ACTGAGTTAC | AGAAAATTTA | GGGCCAAGAT | TTGCCCTGGA | GAAACCAAG | ACAGCAGAGA | TCAACTCAGA | AAAGAGATTA | 2160 |
| 2161 | GTAAATCGAT | GTTTGCAGAG | ATGGAGATCT | TGGGTCAGTT | TAACCTGGA | TTTATAGTAA | TCAAACTGAA | AGAGGACCTC | 2240 |
| 2241 | TTCCTGGTGG | ACCAGCATGC | TGCGGATGAG | AGTTCCAGA | TTGAGATGCT | GCAGCACAC | ACGTGCTCTC | AGCCGACCTG | 2320 |
| 2321 | GCTCATCACG | TGGGTGCACA | CAGGCTTCAG | AGTTCCAGAG | ATGGCTTTGA | GATGAGGATG | TGCTGTCAAT | GAAGCTGTAC | 2400 |
| 2401 | TGATAGAAAA | TCGTACCAAA | TTCAGAAAAC | TGGACCTTTG | ACCCCAAGA | GATGAGGATG | CTCCAGTCAC | TGAAAGGGCT | 2480 |
| 2481 | AAATTGATTT | CCTTACCAAC | TCATGTGCC | AGTCACAG | CTTTTGCTT | GACCCTTGTT | CTGATCTTTA | TGTTAAGTGA | 2560 |
| 2561 | CAGCCCTGGG | GTCATGTGCC | GGCCCTCACG | AGTCAGACAG | ATGTTTGCTT | CCAGAGCCTG | TCGGAAGTCA | GTGATGATTG | 2640 |
| 2641 | GAACGGCGCT | CAATGCCAGC | GAGATGAAGA | AGCTCATCAC | CACATGGGT | GAGATGGACC | ACCCCTGGAA | CTGCCCCCAC | 2720 |
| 2721 | GGCAGGCCAA | CCATGAGCT | CGTTGCCAAT | CTGGATGCA | TCTCTCAGAA | CTGACACACC | CCTTGTAGCA | TAGAGTTTAT | 2800 |
| 2801 | TACAGATTGT | TCGGTTCGCA | AAGAGAAGGT | TTTAAGTAAT | CTGATTATCG | TTGTACAAAA | ATTAGCATGC | TGCTTTAATG | 2880 |
| 2881 | TACTGGATCC | ATTTAAAAGC | AGTGTTAAGG | CAGGCATGAT | GGAGTGTTCC | TCTAGCTCAG | CTACTTGGGT | GATCCGGTGG | 2960 |
| 2961 | GAGCTCATGT | GAGCCCAGA | CTTTGAGACC | ACTCCGAGCC | ACATTCATGA | GACTCAATTC | AAGGACAAAA | AAAAAAGAT | 3040 |
| 3041 | ATTTTTGAAG | CCTTTTAAAA | AAAAA | | | | | | 3065 |

Figure 15

```
mouse   1 MEQTEGVSTECAKAIKPIDGKSVHQICSGQVILSLSTAVKELIENSVDAGATTIDLRLKDYGVDLIEVSDNGCGVEEENFEGLALKHHTSKIQEFADLTQ 100
          ||  |  ||||||||||||||||||  ||||||||||||||||| || |||||||||| ||||||||||||||||||||| |||||||||||||||||
human   1 MERAESSSTEPAKAIKPIDRKSVHQICSGQVVLSLSTAVKELVENSLDAGATNIDLKLKDYGVDLIEVSDNGCGVEEENFEGLTLKHHTSKIQEFADLTQ 100

101 VETFGFRGEALSSLCALSDVTISTCHGSASVGTRLVFDHNGKITQKFTPYPRPKGTTVSVQHLFYTLPVRYKEFQRNIKKEYSKMVQVLQAYCIISAGVRV 200
          ||||||||||||||||||||||||||| |||||||||||||||||||||||||||||||  ||||||| ||||||||||||||| |||| |||||| ||
      101 VETFGFRGEALSSLCALSDVTISTCHASAKVGTRLMFDHNGKIIQKTPYPRPRGTTVSVQQLFSTLPVRHKEFQRNIKKEYAKMVQVLHAYCIISAGIRV 200

201 SCTNQLGQGKRHAVVCTSGTSGMKENIGSVFGQKQLQSLIPFVQLPPSDAVCEEYGLSTSGRHKTFSTFSGFISQCTHGAGRSATDRQFFFINQRPCDPA 300
          |||||||||||| ||||  |  |||||||||||||||||||||||||||| ||||||    |   |  |||||||||||||| |  |||||| | |||
      201 SCTNQLGQGKRQPVVCTGGSPSIKENIGSVFGQKQLQSLIPFVQLPPSDSVCEEYGLSCSDALHNLFYISGFISQCTHGVGRSSTDRQFFFINRRPCDPA 300

301 KVSKLVNEVYHMYNRHQYPPFVVLNVSVDSECVDINVTPDKRQILLQEEKLLLAVLKTSLIGMFDSDANKLNVNQQPLLDVEGNLVKSHTAELEKPVGKQ 400
          ||   |||||||||||||||||||| |||||||||||||||||||||||||||||||||||||||| ||||| |||||||||||||||  | |||  |
      301 KVCRLVNEVYHMYNRHQYPPFVVLNISVDSECVDINVTPDKRQILLQEEKLLLAVLKTSLIGMFDSDVNKLNVSQQPLLDVEGNLIKMHAADLEKPMVEKQ 400

401 DNSPSLKSTADEKRVASISRLREAFSLHPTKEIKSRGPETAELTRSFPSEKRGVLSSYPSDVISYRGLRGSQDKLVSPTDSPGDCMDREKIEKDSGLSST 500
            |  |    | |||||||||||||| ||||||| |   |   |  |      |  |  ||| |       |   |    |        | ||| ||
      401 DQSPSLR-TGEEKKDVSISRLREAFSLRHTTENKPHSPKTPEPRRSPLGQKRGMLSSSTSGAISDKGVLRSQKEAVSSSHGPSDPTDRAEVEKDSGHGST 499

501 SAGSEEEFSTPEVASSFSSDYNVSSLEDRPSQETINC------GDLLPSSRYRTVLEARRPWISMQSSTSSSSVTHKCQALQDRGRPSNVNISQRLPGP 593
                   |            |            |  |      ||  |       |  ||||  | |      |    |     || ||||  |
      500 SVDS-EGFSIPDTGSHCSSEYAASSPGDRGSQEHVDSQEKAPETDDSFSDVDCHSNQEDTGCKFRVLPQPTNLA-TPNTKRFKKEEILSSSDICQKLVNT 597

594 QSTSAAEVDVAIKMNKR---SCSSSSLAKRMKQLQHLKAQNKHELSYRKFRAKICPGENQAAEDELRKEISKSMFAEMEILGQFNLGFIVTKLKEDLFL 689
          |  |   | |||  |     | |||||||||    | |||     |||||||||||||||||||||||||| ||||||||| ||||| | || ||||
      598 QDMSASQVDVAVKINKKVVPLDFSMSSLAKRIKQLHHEAQQSEGEQNYRKFRAKICPGENQAAEDELRKEISKTMFAEMEIIGQFNLGFIITKLNEDIFI 697

690 VDQHAADEKYNFEMLQQHTVLQAQRLITWHTGFRVPRPQTLNLTAVNEAVLIENLEIFRKNGFDFVIDEDAPVTERAKLISLPTSKNWTFGPQDIDELI 789
          ||||| ||||||||||||||| |    |               |||||||||||||||||||||||| |||||||||||||||||||||||||| |||
      698 VDQHATDEKYNFEMLQQHTVLQGQRLIA---------PQTLNLTAVNEAVLIENLEIFRKNGFDFVIDENAPVTERAKLISLPTSKNWTFGPQDVDELI 787

790 FMLSDSPGVMCRPSRVRQMFASRACRKSVMIGTALNASEMKKLITHMGEMDHPWNCPHGRPTMRHVANLDVISQN 864
          ||||||||||||||||||||||||||||||||||||| ||||||||||||||  ||||||||||| |||||||||
      788 FMLSDSPGVMCRPSRVKQMFASRACRKSVMIGTALNTSEMKKLITHMGEMGHPWNCPHGRPTMRHIANLGVISQN 862
```

Figure 16

MAMMALIAN DNA MISMATCH REPAIR GENES MLH1 AND PMS1

This application is a continuation-in-part from U.S. patent application Ser. No. 08/168,877, titled: STRUCTURES FOR AND METHODS OF USING HUMAN DNA MISMATCH REPAIR GENES MLH1 AND MLH2 TO SCREEN FOR CANCER RISK, filed on Dec. 17, 1993, abandoned, the entirety of which is hereby incorporated by reference.

Since filing application Ser. No. 08/168,877, applicants have changed the names of the genes. The "MLH1" gene in the parent application is now named "PMS1". The "MLH2" gene in the parent application is now named "MLH1".

BACKGROUND

This invention was made with government support under Agreement No. GM 32741 awarded by the National Institute of Health in the General Sciences Division. The government has certain rights in the invention.

In recent years, with the development of powerful cloning and amplification techniques such as the polymerase chain reaction (PCR), in combination with the rapidly accumulating body of information concerning the structure and location of numerous human genes and markers, it has become not only possible, but practical and advisable to collect and analyze samples of DNA or RNA from individuals who are members of families which are identified as exhibiting a high frequency of certain genetically transmitted disorders. For example, screening procedures are routinely used to screen for genes involved in sickle cell anemia, cystic fibrosis, fragile X chromosome syndrome and multiple sclerosis. For some types of disorders, early diagnosis can greatly improve the person's long-term prognosis by, for example, adopting an aggressive diagnostic routine, or by making life style changes if appropriate to either prevent or prepare for an anticipated problem.

Once a particular human gene mutation is identified and linked to a disease, development of screening procedures to identify high-risk individuals can be relatively straight forward. For example, after the structure and abnormal phenotypic role of the mutant gene are understood, it is a relatively simple matter to design primers for use in PCR to obtain amplified quantities of the gene from individuals for testing. However, initial discovery of a mutant gene, i.e., its structure, location and linkage with a known inherited health problem, requires substantial experimental effort and creative research strategies.

One approach to discovering the role of a mutant gene in causing a disease begins with clinical studies on individuals who are in families which exhibit a high frequency of the disease. In these studies, the approximate location of the disease-causing locus is determined indirectly by searching for a chromosome marker which tends to segregate with the locus. A principal limitation of this approach is that, although the approximate genomic location of the gene can be determined, it does not generally allow actual isolation or sequencing of the gene.

For example, Lindblom et al.[3] reported results of linkage analysis studies performed with SSLP (simple sequence length polymorphism) markers on individuals from a family known to exhibit a high incidence of hereditary non-polyposis colon cancer (HNPCC). Lindblom et al. found a "tight linkage" between a polymorphic marker on the short arm of human chromosome 3 (3p21–23) and a disease locus apparently responsible for increasing an individual's risk of developing colon cancer. Even though 3p21–23 is a fairly specific location relative to the entire genome, it represents a huge DNA region relative to the probable size of the mutant gene. Searching for the disease locus, i.e., gene mutation, within chromosome 3p21–23 is approximately analogous to searching for a person in San Francisco without knowing their address.

At best, such linkage studies have only limited utility for screening purposes because in order to predict one person's risk, genetic analysis must be performed with tightly linked genetic markers on a number of related individuals in the family. It is often impossible to obtain such information, particularly if affected family members are deceased. Without knowing the gene's structure, it is not possible to sample, amplify, sequence and determine directly whether an individual carries the mutant gene.

Another approach to discovering a disease-causing mutant gene begins with design and trial of PCR primers, based on known information about the disease, for example, theories for disease state mechanisms, related protein structures and function, possible analogous genes in humans or other species, etc. The objective is to isolate and sequence candidate normal genes which are believed to sometimes occur in mutant forms rendering an individual disease prone. This approach is highly dependent on how much is known about the disease at the molecular level, and on the investigator's ability to construct strategies and methods for finding candidate genes.

Association of a mutation in a candidate gene with a disease must ultimately be demonstrated by performing tests on members of a family which exhibits a high incidence of the disease. The most direct and definitive way to confirm such linkage in family studies is to use PCR primers which are designed to amplify portions of the candidate gene in samples collected from the family members. The amplified gene products are then sequenced and compared to the normal gene structure for the purpose of finding and characterizing mutations. A given mutation is ultimately implicated by showing that affected individuals have it while unaffected individuals do not, and that the mutation causes a change in protein function which is not simply a polymorphism.

Another way to show a high probability of linkage between a candidate gene mutation and disease is by determining the chromosome location of the gene, then comparing the gene's map location to known regions of disease-linked loci such as the one identified by Lindblom et al. Coincident map location of a candidate gene in the region of a previously identified disease-linked locus may strongly implicate an association between a mutation in the candidate gene and the disease.

There are other ways to show that mutations in the gene candidate may be linked to the disease. For example, artificially produced mutant forms of the gene can be cloned into animals. Incidence of the disease in animals carrying the mutant gene can then be compared to animals with the normal genotype. Significantly elevated incidence of disease in animals with the mutant genotype, relative to normal animals, may support the theory that mutations in the candidate gene are sometimes responsible for occurrence of the disease in the real world.

One type of disease which has recently received much attention because of the discovery of disease-linkable gene mutations is Hereditary Nonpolyposis Colon Cancer (HNPCC).[1,2] Members of HNPCC families also display increased susceptibility to other cancers including endometrial, gastric and breast. Recent publications have disclosed the identity and role of DNA mismatch repair gene hMSH2 in HNPCC.[1,2,12] Approximately 10% of colorectal cancers are believed to be HNPCC. A significant fraction of HNPCC cancers are believed to be due to mutations in the hMSH2 gene. hMSH2 is one of several genes whose normal function is to identify, and correct DNA mispairs following each round of chromosome replication. When genes of the "DNA Mismatch Repair" pathway are defective, mistakes invariably made during DNA replication remain uncorrected resulting in a greatly increased rate of spontaneous mutation and early onset cancer. It is estimated that as many as 1/200 individuals carry a mutation in either the MSH2 gene or other related genes which encode for another protein in the same DNA mismatch repair pathway.

Based on our knowledge of DNA mismatch repair mechanisms in bacteria and yeast including conservation of mismatch repair genes, we reasoned that, in addition to hMSH2, other human DNA mismatch repair homologs should exist. Further, mutations in such homologs affecting protein function, would be likely to cause genetic instability, possibly leading to an increased risk of certain forms of human cancer. Therefore, an important objective of our work has been to identify other candidate human genes which are useful for screening and identifying individuals who are at elevated risk of developing cancer.

SUMMARY OF THE INVENTION

We have isolated and sequenced two human genes, hPMS1 and hMLH1 each of which we believe encodes for a protein involved in DNA mismatch repair. Our studies strongly support an association between a mutation in hMLH1 and susceptibility to HNPCC. We believe mutations in hPMS1 may also result in an elevated risk of cancer. We believe our characterization and localization of hMLH1 and hPMS1 will be useful in the diagnosis, prevention and treatment of cancer. The most immediate use will be in screening tests on individuals who are members of families which exhibit an unusually high frequency of early onset cancer, for example, HNPCC.

Here we describe the isolation, sequence characterization and chromosomal map positions of hMLH1 and hPMS1. Each of these genes, based upon its similarity to bacterial and yeast genes of known function, is likely to have a role in repairing DNA replication errors that invariably occur during each cell division. The DNA correction process appears to be highly conserved from bacteria to humans, and is commonly referred to as DNA mismatch repair. Based upon studies in bacteria and yeast and the recent finding that mutations in a mismatch repair gene underlie certain forms of human cancer, inheritance of a mutation affecting protein function in either hMLH1 or hPMS1 is expected to raise mutation rates, and therefore predispose such individuals to multiple forms of cancer.

Recent evidence from our lab places the location of hMLH1 at human chromosome 3p21-23. This is a region of the human genome that, based upon family studies, harbors a locus that predisposes individuals to HNPCC. Additionally, we have found a mutation in a conserved region of the hMLH1 cDNA in HNPCC-affected individuals from a Swedish family. The mutation is not found in unaffected individuals from the same family, nor is it a simple polymorphism. Our discovery of a cancer-linked mutation, in hMLH1, combined with the gene's map position which is coincident with a previously identified HNPCC-linked locus, plus the likely role of the hMLH1 gene in mutation avoidance makes the hMLH1 gene a prime candidate for underlying one form of common inherited human cancer, and a prime candidate to screen and identify individuals who have an elevated risk of developing cancer.

We have also isolated and sequenced mouse MLH1 (mMLH1) and PMS1 (mPMS1) genes. We believe mMLH1 and mPMS1 will be useful for constructing animal models to study cancer. For example, such models may be used to identify additional oncogenes and to study environmental effects on mutagenesis.

We have produced polyclonal antibodies directed to a portion of the protein encoded by mPMS1 cDNA These antibodies also react with hPMS1 protein and are useful for detecting the presence of the protein encoded by a normal hPMS1 gene. We are also producing monoclonal antibodies directed to hMLH1.

In addition to diagnostic and therapeutic uses for the genes, our knowledge of hMLH1 and hPMS1 can be used to search for other genes of related function which play a role in certain forms of human cancer.

BRIEF DESCRIPTION OF THE FIGURES

FIG. 2 is an alignment of protein sequences for MutL homologs showing two highly-conserved regions (underlined) which we used to create degenerate PCR oligonucleotides for isolating additional MutL homologs. In FIG. 2, the MutL protein is SEQ ID NO: 5. The HexB protein is SEQ ID NO: 6. The PMS1 protein is SEQ ID NO: 7.

FIG. 3 shows the entire cDNA nucleotide sequence for the human MLH1 gene, and the corresponding predicted amino acid sequence for the human MLH1 protein. The underlined DNA sequences are the regions of cDNA that correspond to the degenerate PCR primers that were originally used to amplify a portion of the MLH1 gene (nucleotides 118–135 and 343–359). In FIG. 3, the cDNA sequence for the human MLH1 gene is SEQ ID NO: 8. The predicted amino acid sequence for the human MLH1 protein is SEQ ID NO: 9.

FIG. 4 shows the nucleotide sequences of two genomic segments of the human MLH1 gene. The first segment shows the genomic sequence surrounding exon corresponding to nucleotides 139–228 of the cDNA (uppercase). The second segment shows the genomic sequence surrounding exon corresponding to nucleotides 229–327 of the cDNA (uppercase). In FIG. 4, the genomic sequence including the exon corresponding to nucleotides 139–228 of the cDNA is SEQ ID NO: 10. The genomic sequence including the exon corresponding to nucleotides 229–327 of the cDNA is SEQ ID NO: 11.

FIG. 5 is an alignment of the predicted amino acid sequences for human and yeast MLH1 proteins. Amino acid identities are indicated by boxes and gaps are indicated by dashes. In FIG. 5, the predicted amino acid sequence for human MLH1 protein is SEQ ID NO: 12. The predicted amino acid for yeast MLH1 protein is SEQ ID NO: 13.

FIG. 9 is an amino acid sequence alignment of the highly-conserved region of the MLH family of proteins surrounding the site of the predicted amino acid substitution. Bold type indicates the position of the predicted serine to phenylalanine amino acid substitution in affected individuals. Also highlighted are the serine or alanine residues conserved at this position in MutL-like proteins. Bullets indicate positions of highest amino acid conservation. For the MLH1 protein, the dots indicate that the sequence has not been obtained. Sequences were aligned as described below in reference to the phylogenetic tree of FIG. 6. The segment of affected human MLH1 is SEQ ID NO: 14. The segment of normal human MLH1 protein is SEQ ID NO: 15. The mouse MLH1 protein is SEQ ID NO: 16. The segment of S. cerevisiae MLH1 protein is SEQ ID NO: 17. The segment of S. cerevisiae PMS1 protein is SEQ ID NO: 18. The segment of E. coli MutL protein is SEQ ID NO: 19. The segment of S. typhimutium MutL protein is SEQ ID NO: 20. The segment of S. pneumoniae HexB protein is SEQ ID NO: 21.

FIG. 10 shows the entire nucleotide sequence for hPMS1. In FIG. 10, the nucleotide sequence for hPMS1 is SEQ ID NO: 22.

FIG. 11 is an alignment of the predicted amino acid sequences for human and yeast PMS1 protein. Amino acid identities are indicated by boxes and gaps are indicated by dashes. The predicted amino acid sequence for hPMS1 protein is SEQ ID NO: 23. The predicted amino acid sequence for yeast PMS1 protein is SEQ ID NO: 24.

FIG. 13 is a partial nucleotide sequence of mMLH1 cDNA. In FIG. 13, the partial nucleotide sequence of mMLH1 cDNA is SEQ ID NO: 25.

FIG. 14 is a comparison of the predicted amino acid sequence for mMLH1 and hMLH1 proteins. The predicted amino acid sequence for mMLH1 is SEQ ID NO: 26. The predicted amino acid sequence for hMLH1 is SEQ ID NO: 27.

FIG. 15 The cDNA nucleotide sequence for mPMS1 is SEQ ID NO: 28.

FIG. 16 is a comparison of the predicted amino acid sequences for mPMS1 and hPMS1 proteins. The predicted amino acid sequence for mPMS1 is SEQ ID NO: 29. The predicted amino acid sequence for hPMS1 is SEQ ID NO: 30.

References

Figure 1:
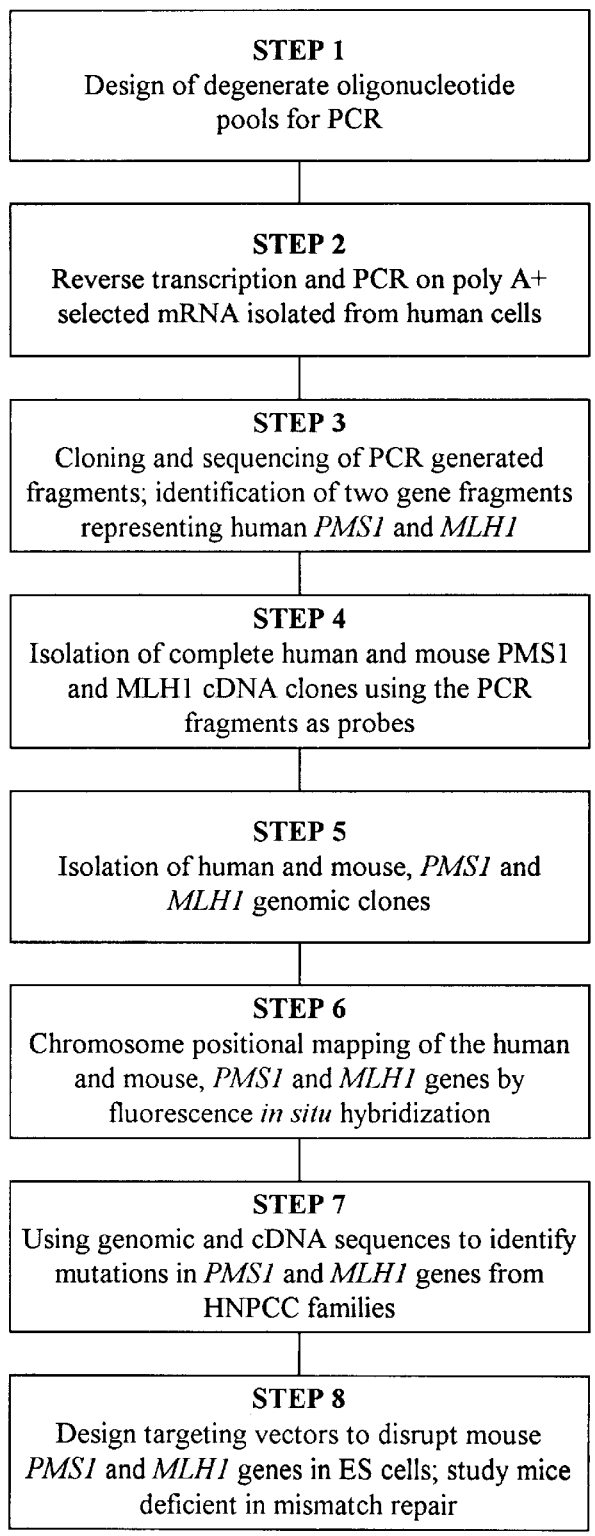
FIG. 1 is a flow chart showing an overview of the sequence of experimental steps we used to isolate, characterize and use human and mouse PMS1 and MLH1 genes.

The following publications are referred to by number in the text of the application. Each of the publications is incorporated here by reference.

1. Fishel, R., et al. Cell 75, 1027–1038 (1993).
2. Leach, F., et al. Cell 75, 1215–1225 (1993).
3. Lindblom, A., Tannergard, P. I., Werelius, B. & Nordenskjold, M. Nature Genetics 5, 279–282 (1993).
4. Prolla, T. A., Christie, D. M. & Liskay, R. M. Molec. and Cell. Biol. 14, 407–415 (1994).
5. Strand, M. Prolla, T. A., Liskay, R. M. & Petes, T. D. Nature 365, 274–276 (1993).
6. Aaltonen, L. A., et al. Science 260, 812–816 (1993).
7. Han, H. J., Yanagisawa, A., Kato, Y., Park, J. G. & Nakamura, Y. Cancer 53, 5087–5089 (1993).
8. Ionov, Y., Peinado, M. A., Malkhosyan, S., Shibata, D. & Perucho, M. Nature 363, 558–561 (1993).
9. Risinger, J. I. et al. Cancer 53, 5100–5103 (1993).
10. Thibodeau, S. N., Bren, G. & Shaid, D. Science 260, 816–819 (1993).
11. Levinson, G. & Gutman, GA. Nucleic Acids Res. 15, 5323–5338 (1987).
12. Parsons, R., et al. Cell 75, 1227–1236 (1993).
13. Modrich, P. Ann. Rev. of Genet. 25, 229–53 (1991).
14. Reenan, R. A. & Kolodner, R. D. Genetics 132, 963–73 (1992).
15. Bishop, D. K., Anderson, J. & Kolodner, R. D. PNAS 86, 3713–3717 (1989).
16. Kramer, W., Kramer, B., Williamson, M. S. & Fogel, S. J. Bacteriol. 171, 5339–5346 (1989).
17. Williamson, M. S., Game, J. C. & Fogel, S., Genetics 110, 609–646 (1985).
18. Prudhomme, M., Martin, B., Mejean, V. & Claverys, J. J. Bacteriol. 171, 5332–5338 (1989).
19. Mankovich, J. A., McIntyre, C. A. & Walker, G. C. J. Bacteriol. 171, 5325–5331 (1989).
20. Lichter, P., et al. Science 247, 64–69 (1990).
21. Boyle, A., Feltquite, D. M., Dracopoli, N., Housman, D. & Ward, D.C. Genomics 12, 106–115 (1992).
22. Lyon, M. F. & Kirby, M. C., Mouse Genome 91, 40–80 (1993).
23. Reenan, R. A. & Kolodner, R. D. Genetics 132, 975–85 (1992).
24. Latif, F. et al. Cancer Research 52, 1451–1456 (1992).
25. Naylor, S. L., Johnson, B. E., Minna, J. D. & Sakaguchi, A. Y. Nature 329, 451–454 (1987).
26. Ali, I. U., Lidereau, R. & Callahan, R. Journal of the National Cancer Institute 81, 1815–1820 (1989).
27. Higgins, D., Bleasby, A. & Fuchs, R. Comput. Apple Biosci. 8, 189–191 (1992).
28. Fields, S. & Song, O. K. Nature 340, 245–246 (1989).
29. Lynch, H. T., et al. Gastroenterology 104, 1535–1549 (1993).
30. Elledge, S. J., Mulligan, J. T., Ramer, S. W., Spottswood, M. & Davis, R. W. Proc. Natl. Acad. Sci. U.S.A. 88, 1731–1735 (1991).
31. Frohman, M. Amplifications, a forum for PCR users 1, 11–15 (1990).
32. Powell, S. M., et al. New England Journal of Medicine 329, 1982–1987 (1993).
33. Wu, D. Y., Nozari, G. Schold, M., Conner, B. J. & Wallace, R. B. DNA 8, 135–142 (1989).
34. Mullis, K. E. B. & Faloona, F. A. Methods in Enzymology 155, 335–350 (1987).
35. Bishop, T. D., Thomas, H. Cancer Sur. 9, 585–604 (1990).
36. Capecchi, M. R. Scientific American 52–59 (March 1994).
37. Erlich, H. A. PCR Technology, Principles and Applications for DNA Amplification (1989).

DESCRIPTION OF THE INVENTION

We have discovered two mammalian genes which are apparently involved in DNA mismatch repair. One of the genes, PMS1, encodes a protein which is homologous to the yeast DNA mismatch repair protein PMS1. We have mapped the locations of PMS1 to human chromosome 7q and to mouse chromosome 5, band G. The other gene, MLH1 (MutL Homolog) encodes a protein which is homologous to the bacterial DNA mismatch repair protein MutL. We have mapped the locations of MLH1 to human chromosome 3p21.3–23 and to mouse chromosome 9, band E.

Recent studies [1,2] have demonstrated involvement of a human DNA mismatch repair gene homolog, hMSH2, on chromosome 2p in HNPCC. Based upon linkage data, a second HNPCC locus has been assigned to chromosome 3p21–23.[3] Examination of tumor DNA from the chromosome 3-linked kindreds revealed dinucleotide repeat instability similar to that observed for other INPCC families[6] and several types of sporadic tumors.7–10 Because dinucleotide repeat instability is characteristic of a defect in DNA mismatch repair, [5, 11, 12] we reasoned that HNPCC linked to chromosome 3p21–23 could result from a mutation in a second DNA mismatch repair gene.

Repair of mismatched DNA in *Escherchia coli* requires a number of genes including mutS, mutL and mutH, defects in any one of which result in elevated spontaneous mutation rates.[13] Genetic analysis in the yeast *Saccharomyces cerevisiae* has identified three DNA mismatch repair genes: a mutS homolog, MSH2,[14] and two mutL homologs, PMS[16] and MLH1.[4] Each of these three genes play an indispensable role in DNA replication fidelity, including the stabilization of dinucleotide repeats.[5]

We believe that hMLH1 is the HNPCC gene previously linked to chromosome 3p based upon the similarity of the hMLH1 gene product to the yeast DNA mismatch repair protein, MLH1,[4] the coincident location of the hMLH1 gene and the HNPCC locus on chromosome 3, and hMLH1 missense mutations which we found in affected individuals from a chromosome 3-linked HNPCC family.

Our knowledge of the human and mouse MLH1 and PMS1 gene structures has many important uses. The gene sequence information can be used to screen individuals for cancer risk. Knowledge of the gene structures makes it possible to easily design PCR primers which can be used to selectively amplify portions of hMLH1 and hPMS1 genes for subsequent comparison to the normal sequence and cancer risk analysis. This type of testing also makes it possible to search for and characterize hMLH1 and hPMS1 cancer-linked mutations for the purpose of eventually focusing the cancer screening effort on specific gene loci. Specific characterization of cancer-linked mutations in hMLH1 and hPMS1 makes possible the production of other valuable diagnostic tools such as allele specific probes which may be used in screening tests to determine the presence or absence of specific gene mutations.

Additionally, the gene sequence information can be used, for example, in a two hybrid system, to search for other genes of related function which are candidates for cancer involvement.

The MLH1 and PMS1 gene structures are useful for making proteins which are used to develop antibodies directed to specific portions or the complete MLH1 and PMS1 proteins. Such antibodies can then be used to isolate the corresponding protein and possibly related proteins for research and diagnostic purposes.

The mouse MLH1 and PMS1 gene sequences are useful for producing mice that have mutations in the respective gene. The mutant mice are useful for studying the gene's function, particularly its relationship to cancer.

Methods for Isolating and Characterizing Mammalian MLH1 and PMS1 Genes.

We have isolated and characterized four mammalian genes, i.e., human MLH1 (hMLH1), human PMS1 (hPMS1), mouse MLH1 (mMLH1) and mouse PMS1 (mPMS1). Due to the structural similarity between these genes, the methods we have employed to isolate and characterize them are generally the same. FIG. 1 shows in broad terms, the experimental approach which we used to isolate and characterize the four genes. The following discussion refers to the step-by-step procedure shown in FIG. 1.

Step 1 Design of degenerate oligonucleotide pools for PCR

Earlier reports indicated that portions of three MutL-like proteins, two from bacteria, MutL and HexB, and one from yeast, PMS1 are highly conserved.[16,18,19] After inspection of the amino acid sequences of HexB, MutL and PMS1 proteins, as shown in FIG. 2, we designed pools of degenerate oligonucleotide pairs corresponding to two highly-conserved regions, KELVEN and GFRGEA, of the mutL-like proteins. The sequences of the degenerate oligonucleotides which we used to isolate the four genes are:

5'-CTTGATTCTAGAGC(T/C)TCNCCNC(T/G)(A/G)AANCC-3' and

5'-AGGTCGGAGCTCAA(A/G)GA(A/G)(T/C)TNGTNGANAA-3'. The sequences of the degenerate oligonucleotides shown above are SEQ ID NOs: 1 and 2, respectively.

The underlined sequences within the primers are XbaI and SacI restriction endonuclease sites respectively. They were introduced in order to facilitate the cloning of the PCR-amplified fragments. In the design of the oligonucleotides, we took into account the fact that a given amino acid can be coded for by more than one DNA triplet (codon). The degeneracy within these sequences are indicated by multiple nucleotides within parentheses or N, for the presence of any base at that position.

Step 2 Reverse transcription and PCR on poly A+ selected MRNA isolated from human cells We isolated messenger (poly A+ enriched) RNA from cultured human cells, synthesized double-stranded cDNA from the mRNA, and performed PCR with the degenerate oligonucleotides.[4] After trying a number of different PCR conditions, for example, adjusting the annealing temperature, we successfully amplified a DNA of the size predicted (~210 bp) for a MutL-like protein.

Step 3 Cloning and sequencing of PCR-generated fragments; identification of two gene fragments representing human PMS1 and MLH1.

We isolated the PCR amplified material (~210bp) from an agarose gel and cloned this material into a plasmid (pUC19). We determined the DNA sequence of several different clones. The amino acid sequence inferred from the DNA sequence of two clones showed strong similarity to other known MutL-like proteins.[4,16,18,19] The predicted amino acid sequence for one of the clones was most similar to the yeast PMS1 protein. Therefore we named it hPMS1, for human PMS1. The second clone was found to most closely resemble yeast MLH1 protein and was named, hMLH1, for human MLH1.

Step 4 Isolation of complete human and mouse PMS1 and MLH1 cDNA clones using the PCR fragments as probes We used the 210bp PCR-generated fragments of the hMLH1 and hPMS1 cDNAs, as probes to screen both human and mouse cDNA libraries (from Stratagene, or as described in reference 30). A number of cDNAs were isolated that corresponded to these two genes. Many of the cDNAs were truncated at the 5' end. Where necessary, PCR techniques [31] were used to obtain the 5'-end of the gene in addition to further screening of cDNA libraries. Complete composite cDNA sequences were used to predict the amino acid sequence of the human and mouse, MLH1 and PMS1 proteins.

Step 5 Isolation of human and mouse, PMS1 and MLH1 genomic clones

Information on genomic and cDNA structure of the human MLH1 and PMS1 genes are necessary in order to thoroughly screen for mutations in cancer prone families. We have used human cDNA sequences as probes to isolate the genomic sequences of human PMS1 and MLH1. We have isolated four cosmids and one P1 clone for hPMS1, that together are likely to contain most, if not all, of the cDNA (exon) sequence. For hMLH1 we have isolated four overlapping λ-phage clones containing 5'-MLH1 genomic sequences and a P1 clone. PCR analysis using pairs of oligonucleotides specific to the 5' and 3' ends of the hMLH1 cDNA, clearly indicates that the P1 clone contains the complete hMLH1 cDNA information. Similarly, genomic clones for mouse PMS1 and MLH1 genes have been isolated and partially characterized (described in Step 8).

Step 6 Chromosome positional mapping of the human and mouse, PMS1 and MLH1 genes by fluorescence in situ hybridization We used genomic clones isolated from human and mouse PMS1 and MLH1 for chromosomal localization by fluorescence in situ hybridization (FISH).[20,21] We mapped the human MLH1 gene to chromosome 3p21.3–23, shown in FIG. 7 as discussed in more detail below. We mapped the mouse MLH1 gene to chromosome 9 band E, a region of synteny between mouse and human.22 In addition to FISH techniques, we used PCR with a pair of hMLH1-specific oligonucleotides to analyze DNA from a rodent/human somatic cell hybrid mapping panel (Coriell Institute for Medial Research, Camden, N.J.). Our PCR results with the panel clearly indicate that hMLH1 maps to chromosome 3. The position of hMLH1 3p21.3–23 is coincident to a region known to harbor a second locus for HNPCC based upon linkage data.

Figure 12:
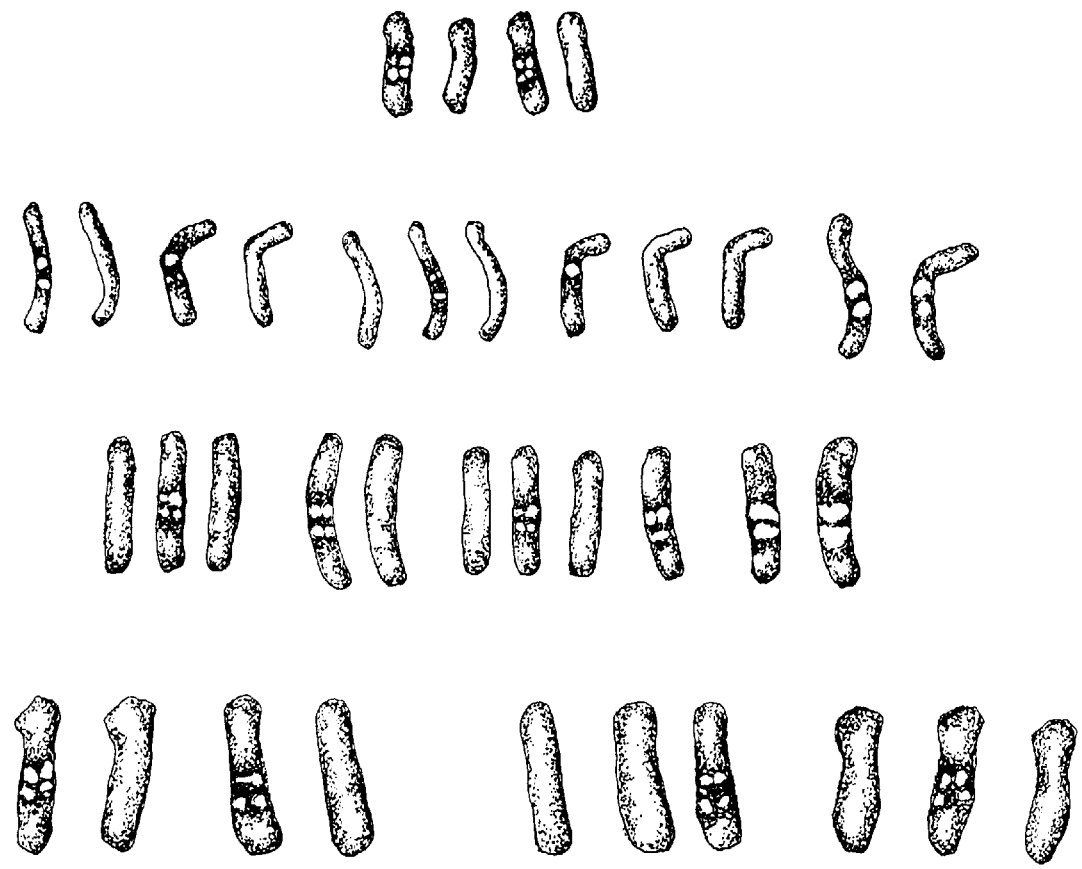
FIG. 12 is a photograph of a composite of chromosome 7 from multiple metaphase spreads showing hybridization of hPMS1.

We mapped the hPMS1 gene, as shown in FIG. 12, to the long (q) arm of chromosome 7 (either 7q11 or 7q22) and the mouse PMS1 to chromosome 5 band G, two regions of synteny between the human and the mouse.[22] We performed PCR using oligonucleotides specific to hPMS1 on DNA from a rodent/human cell panel. In agreement with the FISH data, the location of hPMS1 was confirmed to be on chromosome 7. These observations assure us that our human map position for hMLH1 to chromosome 7q is correct. The physical localization of hPMS1 is useful for the purpose of identifying families which may potentially have a cancer linked mutation in hPMS1.

Step 7 Using genomic and cDNA sequences to identify mutations in hPMS1 and hMLH1 genes from HNPCC Families We are currently analyzing samples collected from individuals in HNPCC families for the purpose of identifying mutations in hPMS1 or hMLH1 genes. Our approach is to design PCR primers based on our knowledge of the gene structures, to obtain exon/intron segments which we can compare to the known normal sequences. We refer to this approach as an "exon-screening".

Using cDNA sequence information we designed hPMS1 and hMLH1 specific oligonucleotides to delineate exon/intron boundaries within genomic sequences. The hPMS1 and hMLH1 specific oligonucleotides were used to probe genomic clones for the presence of exons containing that sequence. Oligonucleotides that hybridized were used as primers for DNA sequencing from the genomic clones. Exon-intron junctions were identified by comparing genomic with cDNA sequences.

Amplification of specific exons from genomic DNA by PCR and sequencing of the products is one method to screen HNPCC families for mutations.[1,2] We have identified genomic clones containing hMLH1 cDNA information and have so far determined several exon-intron junctions. We have designed two pairs of oligonucleotides for PCR, that specifically amplify two exons (corresponding to nucleotides 139–228 and 229–327 in the hMLH1 cDNA, as shown in FIG. 4). We are continuing to use our knowledge of the complete cDNA sequence to determine the remaining exon-intron boundaries.

We have used the exon-screening approach to examine the MLH1 gene of individuals from HNPCC families showing linkage to chromosome 3.[3] As will be discussed in more detail below, we identified a mutation in the MLH1 gene of one such family, consisting of a C to T substitution. We predict that the C to T mutation causes a serine to phenylalanine substitution in a highly-conserved region of the protein. We are continuing to identify HNPCC families from whom we can obtain samples in order to find additional mutations in hMLH1 and hPMS1 genes.

We are also using a second approach to identify mutations in hPMS1 and hMLH1. The approach is to design hPMS1 or hMLH1 specific oligonucleotide primers to produce first-strand cDNA by reverse transcription off RNA. PCR using gene-specific primers will allow us to amplify specific regions from these genes. DNA sequencing of the amplified fragments will allow us to detect mutations.

Step 8 Design targeting vectors to disrupt mouse PMS1 and MLH1 genes in ES cells; study mice deficient in mismatch repair.

We constructed a gene targeting vector based on our knowledge of the genomic mouse PMS1 DNA structure. We used the vector to disrupt the PMS1 gene in mouse embryonic stem cells.[36] The cells were injected into mouse blastocysts which developed into mice that are chimeric (mixtures) for cells carrying the PMS1 mutation. The chimeric animals will be used to breed mice that are heterozygous and homozygous for the PMS1 mutation. These mice will be useful for studying the role of the PMS1 gene in the whole organism.

Human MLH1

The following discussion is a more detailed explanation of our experimental work relating to hMLH1. As mentioned above, to clone mammalian MLH genes, we used polymerase chain reaction (PCR) techniques like those used to identify the yeast MSH1, MSH2 and MLH1 genes and the human MSH2 gene.[1,2,4,14] As template in the PCR, we used double-stranded cDNA synthesized from poly (A+) enriched RNA prepared from cultured primary human fibroblasts. The degenerate oligonucleotides were targeted at the N-terminal amino acid sequences KELVEN and GFRGEA (see FIG. 3), two of the most conserved regions of the MutL family of proteins previously described for bacteria and yeast.[16,18,19] Two PCR products of the predicted size were identified, cloned and shown to encode a predicted amino acid sequence with homology to MutL-like proteins. These two fragments generated by PCR were used to isolate human cDNA and genomic DNA clones.

The oligonucleotide primers which we used to amplify human MutL-related sequences were 5'-CTTGATTCTAGAGC(T/C)TCNCCNC(T/G)(A/G)AANCC-3' SEQ ID NO: 1 and 5'- AGGTCGGAGCTCAA(A/G)GA(A/G)(T/C)TNGTNGANAA-3' SEQ NO 2. PCR was carried out in 50 µL reactions containing cDNA template, 1.0 mM each primer, 5 IU of Taq polymerase (C) 50 mM KCl, 10 mM Tris buffer pH 7.5 and 1.5 mM MgCl. PCR was carried out for 35 cycles of 1 minute at 94° C., 1 minute at 43° C. and 1.5 minutes at 62° C. Fragments of the expected size, approximately 212 bp, were cloned into pUC19 and sequenced. The cloned MLH1 PCR products were labeled with a random primer labeling kit (RadPrime, Gibco BRL) and used to probe human cDNA and genomic cosmid libraries by standard procedures. DNA sequencing of double-stranded plasmid DNAs was performed as previously described.[1]

The hMLH1 cDNA nucleotide sequence as shown in FIG. 3 encodes an open reading frame of 2268 bp. Also shown in FIG. 3 is the predicted protein sequence encoded for by the hMLH1 cDNA. The underlined DNA sequences are the regions of cDNA that correspond to the degenerate PCR primers that were originally used to amplify a portion of the MLH1 gene (nucleotides 118–135 and 343–359).

FIG. 4 shows two genomic segments of the hMLH1 gene. The first sequence shows the nucleotide structure surrounding exon corresponding to nucleotides 139–228 of the cDNA. The second sequence shows the genomic structure surrounding exon corresponding to nucleotides 229–327 of the cDNA.

As shown in FIG. 5, the hMLH1 protein is comprised of 756 amino acids and shares 41% identity with the protein product of the yeast DNA mismatch repair gene, MLH1.[4] The regions of the hMLH1 protein most similar to yeast MLH1 correspond to amino acids 11 through 317, showing 55% identity, and the last 13 amino acids which are identical between the two proteins. FIG. 5 shows an alignment of the predicted human MLH1 and S. cerevisiae MLH1 protein sequences. Amino acid identities are indicated by boxes, and gaps are indicated by dashes. The pair wise protein sequence alignment was performed with DNAStar MegAlign using the clustal method.[27] Pair wise alignment parameters were a ktuple of 1, gap penalty of 3, window of 5 and diagonals of 5. Furthermore, as shown in FIG. 14, the predicted amino acid sequences of the human and mouse Mull proteins show at least 74% identity.

Figure 6:
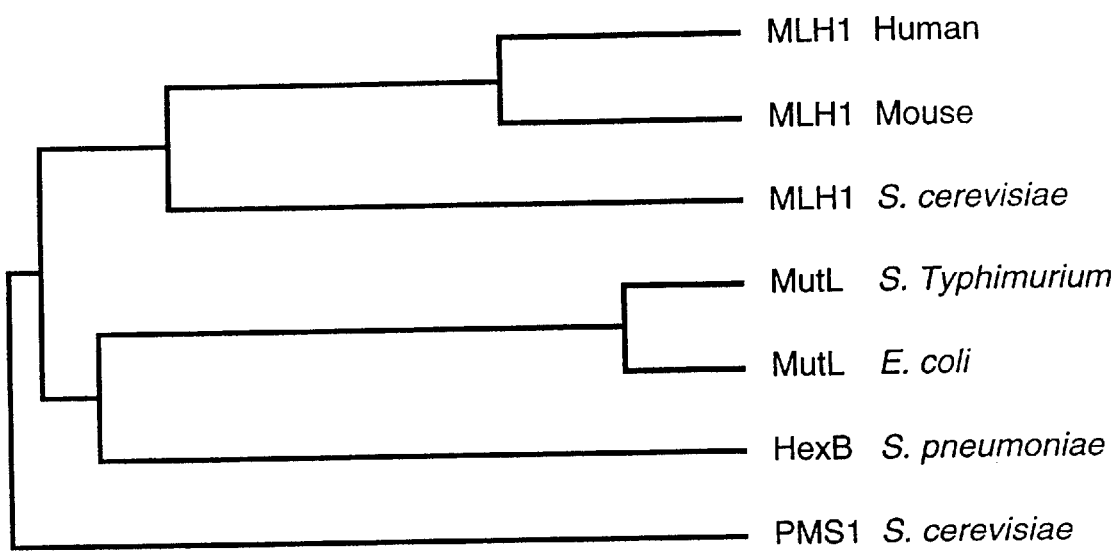
FIG. 6 is a phylogenetic tree of MutL-related proteins.

FIG. 6 shows a phylogenetic tree of MutL-related proteins. The phylogenetic tree was constructed using the predicted amino acid sequences of 7 MutL-related proteins: human MLH1; mouse MLH1; S. cerevisiae MLH1; S. cerevisiae PMS1; E. coli; MutL; S. typhimurium MutL and S. pneumoniae HexB. Required sequences were obtained from GenBank release 7.3. The phylogenetic tree was generated with the PILEUP program of the Genetics Computer Group software using a gap penalty of 3 and a length penalty of 0.1. The recorded DNA sequence has been submitted to GenBank.

Human MLH1 Link to Cancer

As a first step to determine whether hMLH1 was a candidate for the HNPCC locus on human chromosome 3p21–23,[3] we mapped hMLH1 by fluorescence in situ hybridization (FISH).[20,21] We used two separate genomic fragments (data not shown) of the hMLH1 gene in FISH analysis. Examination of several metaphase chromosome spreads localized hMLH1 to chromosome 3p21.3–23.

Figure 7:
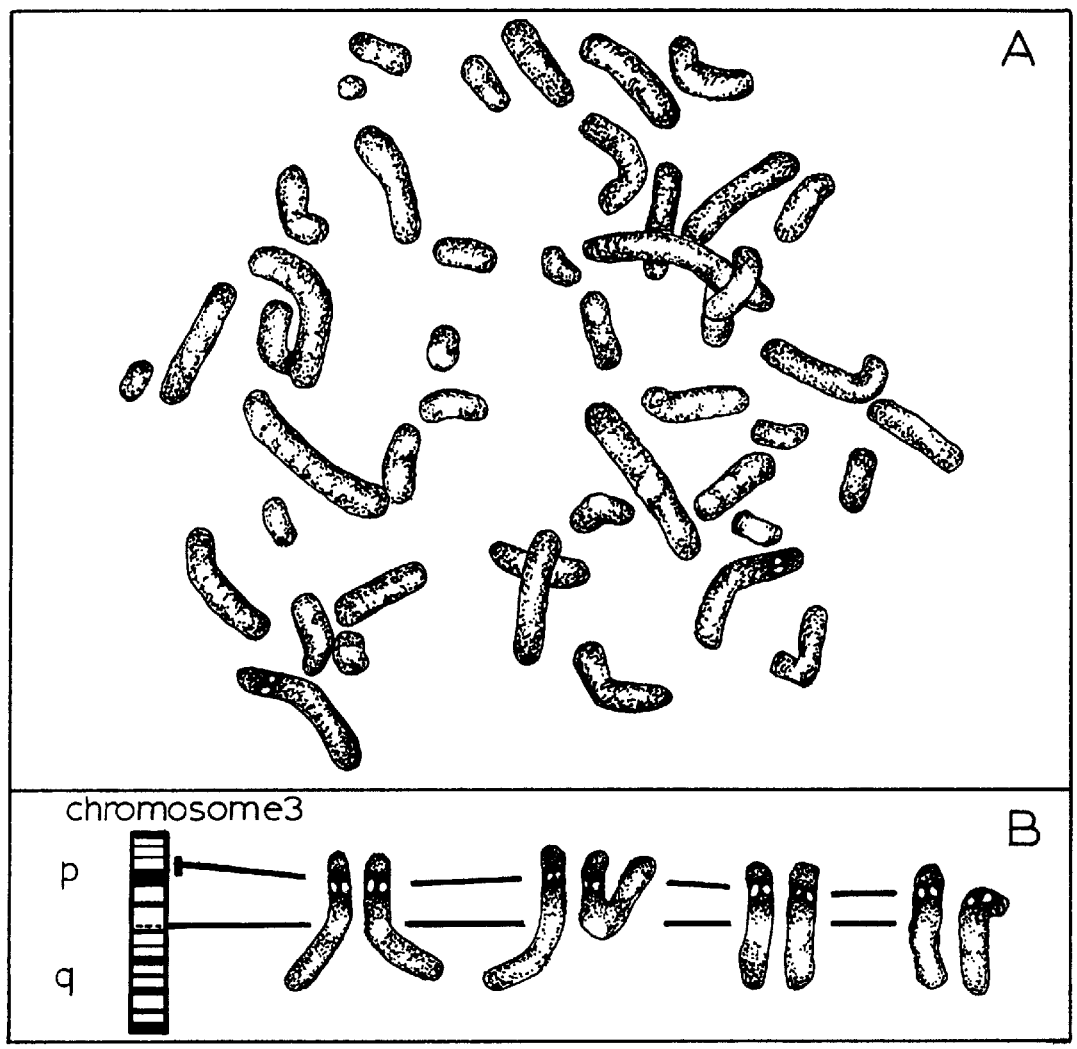
FIG. 7 is a two-panel photograph. The first panel (A) is a metaphase spread showing hybridization of the hMLH1 gene of chromosome 3. The second panel (B) is a composite of chromosome 3 from multiple metaphase spreads aligned with a human chromosome 3 ideogram. The region of hybridization is indicated in the ideogram by a vertical bar.

Panel A of FIG. 7 shows hybridization of hMLH1 probes in a metaphase spread. Biotinylated hMLH1 genomic probes were hybridized to banded human metaphase chromosomes as previously described.20,21 Detection was performed with fluorescein isothiocyanate (FITC)-conjugated avidin (green signal); chromosomes, shown in blue, were counterstained with 4'6-diamino-2-phenylindole (DAPI). Images were obtained with a cooled CCD camera, enhanced, pseudocoloured and merged with the following programs: CCD Image Capture; NIH Image 1.4; Adobe Photoshop and Genejoin Maxpix respectively. Panel B of FIG. 7 shows a composite of chromosome 3 from multiple metaphase spreads aligned with the human chromosome 3 ideogram. Region of hybridization (distal portion of 3p21.3–23) is indicated in the ideogram by a vertical bar.

As independent confirmation of the location of hMLH1 on chromosome 3, we used both PCR with a pair of hMLH1-specific oligonucleotides and Southern blotting with a hMLH1-specific probe to analyze DNA from the NIGMS2 rodent/human cell panel (Coriell Inst. for Med. Res., Camden, N.J., USA). Results of both techniques indicated chromosome 3 linkage. We also mapped the mouse MLH1 gene by FISH to chromosome 9 band E. This is a position of synteny to human chromosome 3p.[22] Therefore, the hMLH1 gene localizes to 3p21.3–23, within the genomic region implicated in chromosome 3-linked HNPCC families.[3]

Next, we analyzed blood samples from affected and unaffected individuals from two chromosome-3 candidate HNPCC families [3] for mutations. One family, Family 1, showed significant linkage (lod score=3.01 at recombination fraction of 0) between HNPCC and a marker on 3p. For the second family, Family 2, the reported lod score (1.02) was below the commonly accepted level of significance, and thus only suggested linkage to the same marker on 3p. Subsequent linkage analysis of Family 2 with the microsatellite marker D3S1298 on 3p21.3 gave a more significant lod score of 1.88 at a recombination fraction of 0 (unpublished data). Initially, we screened for mutations in two PCR-amplified exons of the hMLH1 gene by direct DNA sequencing (FIG. 4). We examined these two exons from three affected individuals of Family 1, and did not detect any differences from the expected sequence. In Family 2, we observed that four individuals affected with colon cancer are heterozygous for a C to T substitution in an exon encoding amino acids 4169, which corresponds to a highly-conserved region of the protein (FIG. 9). For one affected individual, we screened PCR-amplified cDNA for additional sequence differences. The combined sequence information obtained from the two exons and cDNA of this one affected individual represents 95% (i.e. all but the first 116 bp) of the open reading frame. We observed no nucleotide changes other than the C to T substitution. In addition, four individuals from Family 2, predicted to be carriers based upon linkage data, and as yet unaffected with colon cancer, were found to be heterozygous for the same C to T substitution. Two of these predicted carriers are below and two are above the mean age of onset (50 years) in this particular family. Two unaffected individuals examined from this same family, both predicted by linkage data to be non carriers, showed the expected normal sequence at this position. Linkage analysis that includes the C to T substitution in Family 2 gives a lod score of 2.23 at a recombination fraction 0. Using low stringency cancer diagnostic criteria, we calculated a lod score of 2.53. These data indicate the C to T substitution shows significant linkage to the HNPCC in Family 2.

Figure 8:
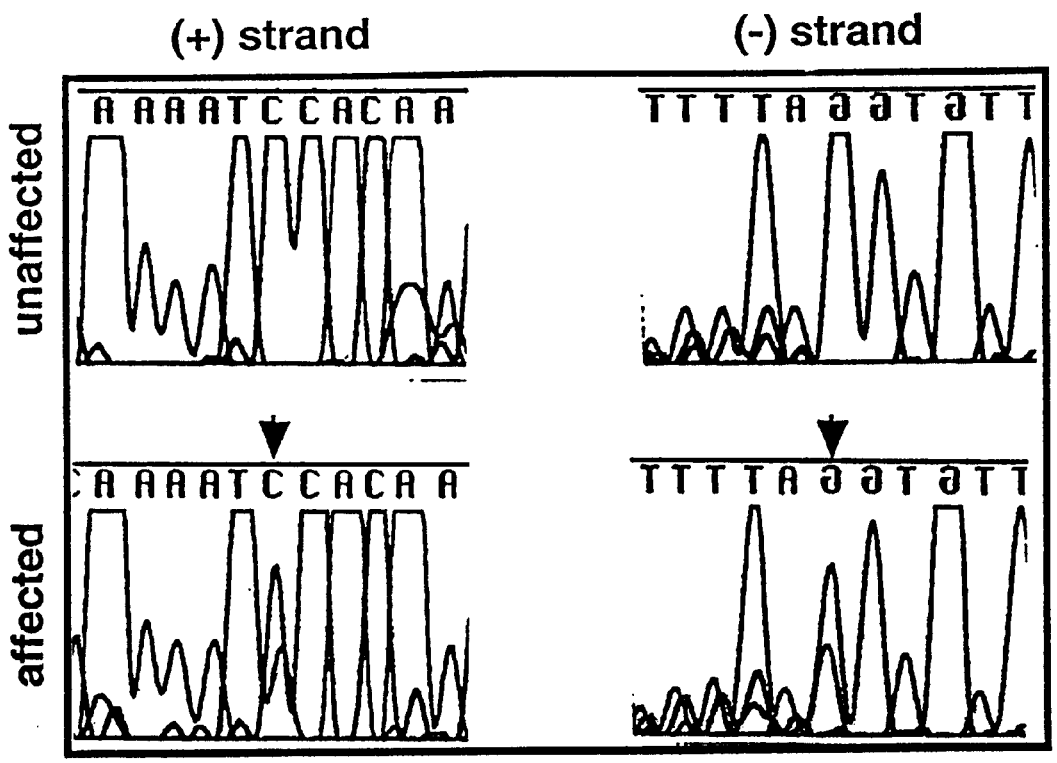
FIG. 8 is a comparison of sequence chromatograms from affected and unaffected individuals showing identification of a C to T transition mutation that produces a non-conservative amino acid substitution at position 44 of the hMLH1 protein.

FIG. 8 shows sequence chromatograms indicating a C to T transition mutation that produces a non-conservative amino acid substitution at position 44 of the hMLH1 protein. Sequence analysis of one unaffected (top panels, plus and minus strands) and one affected individual (lower panels, plus and minus strands) is presented. The position of the heterozygous nucleotide is indicated by an arrow. Analysis of the sequence chromatographs indicates that there is sufficient T signal in the C peak and enough A signal in the G peak for the affected individuals to be heterozygous at this site.

To determine whether this C to T substitution was a polymorphism, we sequenced this same exon amplified from the genomic DNA from 48 unrelated individuals and observed only the normal sequence. We have examined an additional 26 unrelated individuals using allele specific oligonucleotide (ASO) hybridization analysis.[33] The ASO sequences which we used are:
5'-ACTTGTGGATTTTGC-3' and
5'-ACTTGTGAATTTTGC-3'. The ASO sequences shown above are SEQ ID NOs: 3 and 4, respectively.

Based upon direct DNA sequencing and ASO analysis, none of these 74 unrelated individuals carry the C to T substitution. Therefore, the C to T substitution observed in Family 2 individuals is not likely to be a polymorphism. As mentioned above, we did not detect this same C to T substitution in affected individuals from a second chromosome 3-linked family, Family 1.[3] We are continuing to study individuals of Family 1 for mutations in hMLH1.

Table 1 below summarizes our experimental analysis of blood samples from affected and unaffected individuals from Family 2 and unrelated individuals.

TABLE 1

| FAMILY 2 Status | Number of Individuals with C to T Mutation/ Number of Individuals Tested |
|---|---|
| Affected | 4/4 |
| Predicted Carriers | 4/4 |
| Predicted Non-carriers | 0/2 |
| Unrelated Individuals | 0/74 |

Based on several criteria, we suggest that the observed C to T substitution in the coding region of hMLH1 represents the mutation that is the basis for HNPCC in Family 2.[3] First, DNA sequence and ASO analysis did not detect the C to T substitution in 74 unrelated individuals. Thus, the C to T substitution is not simply a polymorphism. Second, the observed C to T substitution is expected to produce a serine to phenylalanine change at position 44 (See FIG. 9). This amino acid substitution is a non-conservative change in a conserved region of the protein (FIGS. 3 and 9). Secondary structure predictions using Chou-Fasman parameters suggest a helix-turn-beta sheet structure with position 44 located in the turn. The observed Ser to Phe substitution, at position 44 lowers the prediction for this turn considerably, suggesting that the predicted amino acid substitution alters the conformation of the hMLH1 protein. Therefore, we propose that hMLH1 represents a second DNA mismatch repair gene that is involved in HNPCC. At present, we have no direct evidence that the hMLH1 gene is involved in the correction of DNA mispairs. In bacteria and yeast, a mutation affecting DNA mismatch repair causes comparable increases in the rate of spontaneous mutation including additions and deletions within dinucleotide repeats.[4,5,11,13,14,15,16] In humans, mutation of hMSH2 is the basis of chromosome-2 HNPCC,[1,2] tumors of which show microsaterlite instability and an apparent defect in mismatch repair.[12] Chromosome 3-linked HNPCC is also associated with instability of dinucleotide repeats.[3] Combined with these observations, the high degree of conservation between the human MLH1 protein and the yeast DNA mismatch repair protein MLH1 suggests that hMLH1 is likely to function in DNA mismatch repair. During isolation of the hMLH1 gene, we identified the hPMS1 gene. This observation suggests that mammalian DNA mismatch repair, like that in yeast,[4] may require at least two MutL-like proteins.

It should be noted that it appears that different HNPCC families show different mutations in the MLH1 gene. As explained above, affected individuals in Family 1 showed "tight linkage" between HNPCC and a locus in the region of 3p21–23. However, affected individuals in Family 1 do not have the C to T mutation found in Family 2. It appears that the affected individuals in Family 1 have a different mutation in their MLH1 gene. Unlike, for example, sickle cell anemia, in which essentially all known affected individuals have the same mutation genotype, it is likely that multiple hMLH1 mutations will be eventually linked to cancer. Therefore, knowledge of the entire cDNA sequence for hMLH1 (and probably hPMS1), as well as genomic sequences particularly those that surround exons, will be useful and important for characterizing mutations in families identified as exhibiting a high frequency of cancer.

In summary, we have described a second DNA mismatch repair gene homolog, hMLH1, which is likely to be the hereditary nonpolyposis colon cancer gene previously localized by linkage analysis to chromosome 3p21–23.[3] Like other HNPCC families,[29,35] chromosome 3p-families show apparent predisposition to several types of cancer.[3] The availability of the hMLH1 and hMSH2 gene sequences will facilitate the screening of HNPCC families for mutations in either gene. In addition, although loss of heterozygosity (LOH) of linked markers is not a feature of either the 2p or 3p forms of HNPCC,[3,6] LOH involving the 3p21.3–23 region has been observed in several human cancers.24-26 This raises the possibility that hMLH1 mutation may play some role in these tumors. Finally, it seems likely that defects in additional DNA mismatch repair genes will prove to be the basis for the cancer in HNPCC families showing neither chromosome 2p or 3p involvement.[3]

Human PMS1

Figure 11:
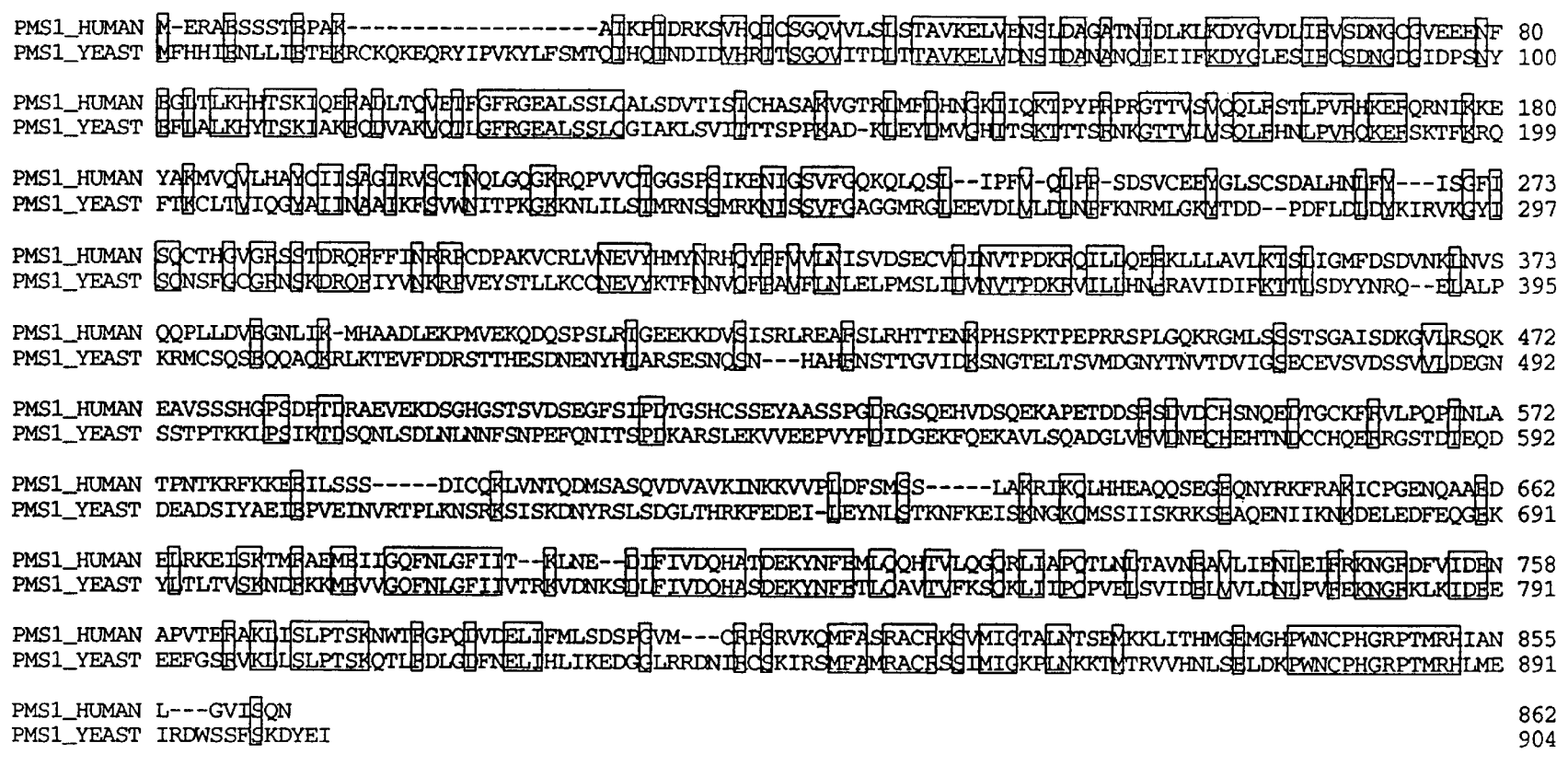

Human PMS1 was isolated using the procedures discussed with reference to FIG. 1. FIG. 10 shows the entire hPMS1 cDNA nucleotide sequence. FIG. 11 shows an alignment of the predicted human and yeast PMS1 protein sequences. FIG. 12 is a metaphase spread showing the results of FISH analysis to determine the map location of human PMS1. The results shown in FIG. 12 indicate two possible loci for human PMS1, namely 7q 11 and 7q 22.

Utility of the hMLH1 and hPMS1 Genes

Our recent map position and mutation data strongly suggest that the hMLH1 gene is the HNPCC locus that, based upon linkage studies, maps to chromosome 3p.[3] The hPMS1 on 7q is, a priori, also a strong candidate to represent HNPCC that maps to neither 2p or 3p.1–3,6 At present, our collaborators in Sweden are checking such "unlinked" HNPCC families for linkage to 7q. Clearly, our data indicate that the hMLH1 gene has significant utility in the screening and diagnosis of hereditary human cancer. Further studies are required to fully determine the utility of the hPMS1 gene in human cancer risk screening. We would like to point out, however, that several observations make the hPMS1 gene a strong DNA mismatch repair gene candidate and hence a possible player in human cancer. These observations include: 1) the involvement of mismatch repair gene homologs, hMSH2 and hMLH1, in HNPCC;[1,2] 2) the close similarity of the human and yeast PMS1 proteins 3) the role of the yeast PMS1 protein in DNA mismatch repair;[4] and 4) our published genetic and unpublished biochemical data strongly suggesting that the yeast PMS1 and MLH1 proteins act as a heteromeric complex during DNA mismatch repair.

Use of MLH genes in the detection of individuals at risk for cancer

It has been estimated that approximately 1,000,000 individuals in the United States carry (are heterozygous for) an HNPCC mutant gene.[29] Furthermore, estimates suggest that 50–60% of HNPCC families segregate mutations in the MSH2 gene that resides on chromosome 2p.[1,2] Another significant fraction would appear to be associated with the HNPCC gene that maps to chromosome 3p21–22, presumably due to hMLH1 mutations such as the C to T transition discussed above. Identification of families that segregate mutant alleles of either the hMSH2 or HMLH1 gene, and the determination of which individuals in these families actually have the mutation will be of great utility in the early intervention into the disease. Such early intervention will likely include early detection through screening and aggressive follow-up treatment of affected individuals. In addition, determination of the genetic basis for both familial and sporadic tumors could direct the method of therapy in the primary tumor, or in recurrences.

Detection of HNPCC families and their mutation(s)

Initially, HNPCC candidate families will be diagnosed partly through the study of family histories, most likely at the local level, e.g., by hospital oncologists. One criterion for HNPCC is the observation of microsatellite instability in these individual's tumors.[3,6] The presenting patient would be tested for mutations in hMSH2, hMLH1 and other genes involved in DNA mismatch repair as they are identified. This is most easily done by sampling blood from the individual. Also highly useful would be freshly frozen tumor tissue. Of importance to note for the screening procedure, the affected individuals are heterozygous for the offending mutation in their normal tissues.

The available tissues, e.g. blood and tumor, are worked up for PCR-based mutation analysis using one or both of the following procedures:

1) Linkage analysis with a microsatellite marker tightly linked to the hMLH1 gene.

One approach to identify cancer prone families with a hMLH1 mutation is to perform linkage analysis with a highly polymorphic marker located within or tightly linked to hMLH1. Microsatellites are highly polymorphic and therefore are very useful as markers in linkage analysis. Because we possess the hMLH1 gene on a single large genomic fragment in a P1 phage clone (~100 kbp), it is very likely that one or more microsatellites, e.g. tracts of dinucleotide repeats, exist within, or very close to, the hMLH1 gene. Once such markers have been identified, PCR primers will be designed to amplify the stretches of DNA containing the microsatellites. DNA of affected and unaffected individuals from a family with a high frequency of cancer will be screened to determine the segregation of the MLH1 markers and the presence of cancer. The resulting data can be used to calculate a lod score and hence determine the likelihood of linkage between hMLH1 and the occurrence of cancer. Once linkage is established in a given family, the same polymorphic marker can be used to test other members of the kindred for the likelihood of their carrying the hMLH1 mutation.

2) Sequencing of reverse transcribed cDNA.
   a) RNA from affected individuals, unaffecteds and unrelated individuals is reverse transcribed (R'd), followed by PCR to amplify the cDNA in 4–5 overlapping portions.34,37 It should be noted that for the purposes of PCR, many different oligonucleotide primer pair sequences may potentially be used to amplify relevant portions of an individual's hMLH1 or hPMS1 gene for genetic screening purposes. With the knowledge of the cDNA structures for the genes, it is a straight-forward exercise to construct primer pairs which are likely to be effective for specifically amplifying selected portions of the gene. While primer sequences are typically between 20 to 30 bases long, it may be possible to use shorter primers, potentially as small as approximately 13 bases, to amplify specifically selected gene segments. The principal limitation on how small a primer sequence may be used is that it must be long enough to bond specifically to the targeted gene segment.

These PCR products, in total representing the entire cDNA, are then sequenced and their sequences compared. In most cases a mutation will be observed in the affected individual. Ideally, the nature of mutation will indicate that it is likely to inactivate the gene product. Otherwise, the possibility that the alteration is not simply a polymorphism must be determined.

b) Certain mutations, e.g. those affecting splicing or resulting in translation stop codons, can destabilize the messenger RNA produced from the mutant gene and hence comprise the normal RT-based mutation detection method. One recently reported technique can circumvent this problem by testing whether the mutant cDNA can direct the synthesis of normal length protein in a coupled in vitro transcription/translation system.[32]

3) Direct sequencing of the genomic DNA.

A second route to detect mutations relies on examining the exons and the exon/intron boundaries by PCR cycle sequencing directly off a DNA template.[1,2] This method requires the use of oligonucleotide pairs that amplify individual exons for direct PCR cycle sequencing. The method depends upon genomic DNA sequence information at each intron/exon boundary (50 bp, or greater, for each boundary). The advantage of the technique is two fold. First, because DNA is more stable than RNA, the condition of the material used for PCR is not as important as it is for RNA-based protocols. Second, most any mutation within the actual transcribed region of the gene, including those in an intron affecting splicing, should be detectable.

Therefore, for each candidate gene, mutation detection may require knowledge of both the entire cDNA structure, and all intron/exon boundaries of the genomic structure. With such information, the type of causal mutation in a particular family can be determined. In turn, a more specific and efficient mutation detection scheme can be adapted to that family. In many cases such a "family by family" delineation will most likely be beneficial for HNPCC. The disease is not only genetically heterogeneous in the sense that more than one gene is involved, but also because for a particular gene, multiple types of mutations are involved.[2] Any given family is highly likely to segregate one particular mutation. However, as the nature of the mutation in multiple families is determined, the spectrum of the most prevalent mutations in the population can be determined. In general, determination of the most frequent mutations will direct and streamline mutation detection.

Because HNPCC is so prevalent in the human population, carrier detection at birth could become part of standardized neonatal testing. Families at risk would be identified and all members not previously tested would be tested. Eventually, all affected kindreds could be determined.

Mode of mutation screening and testing

DNA-based Testing

Some of the initial testing, including detecting likely HNPCC families by standard diagnosis and family history study, will likely be done in local and smaller DNA diagnosis laboratories. However, large scale testing of multiple family members, and certainly population wide testing, will ultimately require large efficient centralized commercial facilities. The exact method of large scale screening at such facilities is not clear but is likely to involve at least some of the methods and techniques described above.

It seems likely that tests will be developed based on the determination of the most common mutations for the two major genes behind HNPCC, the hMSH2 gene on chromosome 2p and the MLH1 gene on chromosome 3p. A variety of tests are likely to be developed. For example, one possibility is a set of tests employing oligonucleotide hybridizations that distinguish the normal vs. mutant alleles.[33] As already noted, our knowledge of the nucleotide structures for hMLH1, hPMS1 and hMSH2 genes makes possible the design of numerous oligonucleotide primer pairs which may be used to amplify specific portions of an individual's mismatch repair gene for genetic screening and cancer risk analysis. Our knowledge of the genes' structures also makes possible the design of labeled probes which can be quickly used to determine the presence or absence of all or a portion of one of the DNA mismatch repair genes. For example, allele-specific oligomer probes (ASO) may be designed to distinguish between alleles. ASOs are short DNA segments that are identical in sequence except for a single base difference that reflects the difference between normal: and mutant alleles. Under the appropriate DNA hybridization conditions, these probes can recognize a single base difference between two otherwise identical DNA sequences. Probes can be labeled radioactively or with a variety of non-radioactive reporter molecules, for example, fluorescent or chemiluminescent moieties. Labeled probes are then used to analyze the PCR sample for the presence of the disease-causing allele. The presence or absence of several different disease-causing genes can readily be determined in a single sample. The length of the probe must be long enough to avoid non-specific binding to nucleotide sequences other than the target. All tests will depend ultimately on accurate and complete structural information on the MLH1 gene on chromosome 3p and the MutS homolog, hMSH2, on chromosome 2p.

Protein Detection-based Screening

Although it is likely that most screening tests will be initially DNA-based, tests based on the status of the protein product, per se, will also have utility. These protein-examining tests will most likely utilize antibody reagents specific to either the hMLH11, hPMS1 and hMSH2 proteins or other related "cancer" gene products as they are identified.

For example, a frozen tumor specimen can be cross-sectioned and prepared for antibody staining using indirect fluorescence techniques. Certain gene mutations are expected to alter or destabilize the protein structure sufficiently such as to give an altered or reduced signal after antibody staining. It is likely that such tests would be performed most often in cases where gene involvement in a family's cancer has not yet been established. Therefore, the development of diagnostic monoclonal antibodies against the human MLH1 and PMS1 proteins is a high priority in our laboratory. We are overexpressing each of these human proteins in bacteria. We will purify the proteins, inject them into mice and derive protein specific monoclonal antibodies which can be used for diagnostic and research purposes.

Use of hPMS1 and hMLH1 cDNAs for Isolating Additional Genes of Related Function

Proteins that interact physically with either hMLH1 and/or hPMS1, are likely to be involved in DNA mismatch repair. By analogy to hMLH1 and hMSH2, mutations in the genes which encode for such proteins would be strong candidates for potential cancer linkage. A powerful molecular genetic approach using yeast, referred to as a "two-hybrid system", allows the relatively rapid detection and isolation of genes encoding proteins that interact with a gene product of interest, e.g. hMLH1.[28]

The two-hybrid system involves two plasmid vectors each intended to encode a fusion protein. Each of the two vectors contains a portion, or domain, of a transcription activator. The yeast cell used in the detection scheme contains a "reporter" gene. The activator alone cannot activate transcription. However, if the two domains are brought into close proximity then transcription may occur. The cDNA for the protein of interest, e.g., hMLH1 is inserted within a reading frame in one of the vectors. This is termed the "bait". A library of human cDNAs, inserted into a second plasmid vector so as to make fusions with the other domain of the transcriptional activator, is introduced into the yeast cells harboring the "bait" vector. If a particular yeast cell receives a library member that contains a human cDNA encoding a protein that interacts with hMLH1 protein, this interaction will bring the two domains of the transcriptional activator into close proximity, activate transcription of the reporter gene and the yeast cell will turn blue. Next, the insert is sequenced to determine whether it is related to any sequence in the data base. The same procedure can be used to identify yeast proteins in DNA mismatch repair or a related process. Performing the yeast and human "hunts" in parallel has certain advantages. The function of novel yeast homologs can be quickly determined in yeast by gene disruption and subsequent examination of the genetic consequences of being defective in the new found gene. These yeast studies will help guide the analysis of novel human "hMLH1-or hPMS1-interacting" proteins in much the same way that the yeast studies on PMS1 and MLH1 have influenced our studies of the human MLH1 and PMS1 genes.

Production of Antibodies

By using our knowledge of the DNA sequences for hMLH1 and hPMS1, we can synthesize all or portions of the predicted protein structures for the purpose of producing antibodies. One important use for antibodies directed to hMLH1 and hPMS1 proteins will be for capturing other proteins which may be involved in DNA mismatch repair. For example, by employing coimmuno-precipitation techniques, antibodies directed to either hMLH1 or hPMS1 may be precipitated along with other associated proteins which are functionally and/or physically related. Another important use for antibodies will be for the purpose of isolating hMLH1 and hPMS1 proteins from tumor tissue. The hMLH1 and hPMS1 proteins from tumors can then be characterized for the purpose of determining appropriate treatment strategies.

We are in the process of developing monoclonal antibodies directed to the hMLH1 protein. We have used the following procedure to produce polyclonal antibodies directed to the human and mouse forms of PMS1 protein.

We inserted a 3' fragment of the mouse PMS1 cDNA in the bacterial expression plasmid vector, pET (Novagen, Madison, Wis.). The expected expressed portion of the mouse PMS1 protein corresponds to a region of approximately 200 amino acids at the end of the PMS1 protein. This portion of the mPMS1 is conserved with yeast PMS1 but is not conserved with either the human or the mouse MLH1 proteins. One reason that we selected this portion of the PMS1 protein for producing antibodies is that we did not want the resulting antibodies to cross-react with MLH1. The mouse PMS1 protein fragment was highly expressed in *E. coli*, purified from a polyacrylamide gel and the eluted protein was then prepared for animal injections. Approximately 2 mg of the PMS1 protein fragment was sent to the Pocono Rabbit Farm (Pa.) for injections into rabbits. Sera from rabbits multiple times was tittered against the PMS1 antigen using standard ELISA techniques. Rabbit antibodies specific to mouse PMS1 protein were affinity-purified using columns containing immobilized mouse PMS1 protein. The affinity-purified polyclonal antibody preparation was tested further using Western blotting and dot blotting. We found that the polyclonal antibodies recognized, not only the mouse PMS1 protein, but also the human PMS1 protein which is very similar. Based upon the Western blots, there is no indication that other proteins were recognized strongly by our antibody, including either the human or mouse MLH1 proteins.

Mouse MLH1

Using the procedure outlined above with reference to FIG. 1, we have determined a partial nucleotide sequence of mouse MLH1 cDNA, as shown in FIG. 13. FIG. 14 shows the corresponding predicted amino acid sequence for mMLH1 protein in comparison to the predicted hMLH1 protein sequence. Comparison of the mouse and human MLH1 proteins as well as the comparison of hMLH1 with yeast MLH1 proteins, as shown in FIG. 9, indicate a high degree of conservation.

Mouse PMS1

Using the procedures discussed above with reference to FIG. 1, we isolated and sequenced the mouse PMS1 gene, as shown in FIG. 15. This cDNA sequence encodes a predicted protein of 864 amino acids, as shown in FIG. 16, where it is compared to the predicted amino acid sequence for hPMS1.

The degree of identity between the predicted mouse and human PMS1 proteins is high, as would be expected between two mammals. Similarly, as noted above, there is strong similarity between the human PMS1 protein and the yeast DNA mismatch repair protein PMS1, as shown in FIG. 11. The fact that yeast PMS1 and MLH1 function in yeast to repair DNA mismatches, strongly suggests that human and mice PMS1 and MLH1 are also mismatch repair proteins.

Uses for Mouse MLH1 and PMS1

We believe our isolation and characterization of mMLH1 and mPMS1 genes will have many research applications. For example, as already discussed above, we have used our knowledge of the mPMS1 gene to produce antibodies which react specifically with hPMS1. We have already explained that antibodies directed to the human proteins, MLH1 or PMS1 may be used for both research purposes as well as diagnostic purposes.

We also believe that our knowledge of mPMS1 and mMLH1 will be useful for constructing mouse models in order to study the consequences of DNA mismatch repair defects. We expect that mPMS1 or mMLH1 defective mice will be highly prone to cancer because chromosome 2p and 3p-associated HNPCC are each due to a defect in a mismatch repair gene.[1,2] As noted above, we have already produced chimeric mice which carry an mPMS1 defective gene. We are currently constructing mice heterozygous for mPMS1 or mMLH1 mutation. These heterozygous mice should provide useful animal models for studying human cancer, in particular HNPCC. The mice will be useful for analysis of both intrinsic and extrinsic factors that determine cancer risk and progression. Also, cancers associated with mismatch repair deficiency may respond differently to conventional therapy in comparison to other cancers. Such animal models will be useful for determining if differences exist, and allow the development of regimes for the effective treatment of these types of tumors. Such animal models may also be used to study the relationship between hereditary versus dietary factors in carcinogenesis.

We claim:

1. A purified mouse mPMS1 gene shown in SEQ ID NO:28.
2. Isolated and purified DNA comprising a segment of at least 13 nucleotides of mPMS1 as shown in SEQ ID NO:28.
3. An isolated polynucleotide comprising at least two separate segments, each segment having a sequence of at least 13 nucleotides the same as any 13 nucleotide sequence in SEQ ID NO: 28, wherein the sequences of the segments can be used to design a pair of olizonucleotide primers for amplifying specifically at least a portion of mPMS1.

* * * * *

SEQUENCE LISTING (1) GENERAL INFORMATION:

(iii) NUMBER OF SEQUENCES: 30

(2) INFORMATION FOR SEQ ID NO:1:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

CTTGATTCTA GAGCYTCNCC NCKRAANCC                    29

(2) INFORMATION FOR SEQ ID NO:2:

(i) SEQUENCE CHARACTERISTICS:
      (A) LENGTH: 29 base pairs
      (B) TYPE: nucleic acid
      (C) STRANDEDNESS: single (D) TOPOLOGY: linear (ii) MOLECULE TYPE: cDNA (xi) SEQUENCE DESCRIPTION: SEQ ID NO:2:

AGGTCGGAGC TCAARGARYT NGTNGANAA                                            29

(2) INFORMATION FOR SEQ ID NO:3:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:3:

ACTTGTGGAT TTTGC                                                           15

(2) INFORMATION FOR SEQ ID NO:4:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:4:

ACTTGTGAAT TTTGC                                                           15

(2) INFORMATION FOR SEQ ID NO:5:

(i) SEQUENCE CHARACTERISTICS:
            (A) LENGTH: 361 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:5:

Met Pro Ile Gln Val Leu Pro Pro Gln Leu Ala Asn Gln Ile Ala Ala
    1               5                   10                  15

Gly Glu Val Val Glu Arg Pro Ala Ser Val Val Lys Glu Leu Val Glu
                20                  25                  30

Asn Ser Leu Asp Ala Gly Ala Thr Arg Val Asp Ile Asp Ile Glu Arg
            35                  40                  45

Gly Gly Ala Lys Leu Ile Arg Ile Arg Asp Asn Gly Cys Gly Ile Lys
        50                  55                  60

Lys Glu Glu Leu Ala Leu Ala Leu Ala Arg His Ala Thr Ser Lys Ile
    65                  70                  75                  80

Ala Ser Leu Asp Asp Leu Glu Ala Ile Ile Ser Leu Gly Phe Arg Gly
                    85                  90                  95

Glu Ala Leu Ala Ser Ile Ser Ser Val Ser Arg Leu Thr Leu Thr Ser
                100                 105                 110

Arg Thr Ala Glu Gln Ala Glu Ala Trp Gln Ala Tyr Ala Glu Gly Arg
                115                 120                 125

Asp Met Asp Val Thr Val Lys Pro Ala Ala His Pro Val Gly Thr Thr
            130                 135                 140

Leu Glu Val Leu Asp Leu Phe Tyr Asn Thr Pro Ala Arg Arg Lys Phe
    145                 150                 155                 160

```
Met Arg Thr Glu Lys Thr Glu Phe Asn His Ile Asp Glu Ile Ile Arg
                165                 170                 175
Arg Ile Ala Leu Ala Arg Phe Asp Val Thr Leu Asn Leu Ser His Asn
            180                 185                 190
Gly Lys Leu Val Arg Gln Tyr Arg Ala Val Ala Lys Asp Gly Gln Lys
        195                 200                 205
Glu Arg Arg Leu Gly Ala Ile Cys Gly Thr Pro Phe Leu Glu Gln Ala
    210                 215                 220
Leu Ala Ile Glu Trp Gln His Gly Asp Lys Thr Lys Arg Gly Trp Val
225                 230                 235                 240
Ala Asp Pro Asn His Thr Thr Thr Ala Leu Thr Glu Ile Gln Tyr Cys
                245                 250                 255
Tyr Val Asn Gly Arg Met Met Arg Asp Arg Leu Ile Asn His Ala Ile
            260                 265                 270
Arg Gln Ala Cys Glu Asp Lys Leu Gly Ala Asp Gln Gln Pro Ala Phe
        275                 280                 285
Val Leu Tyr Leu Glu Ile Asp Pro His Gln Val Asp Val Asn Val His
    290                 295                 300
Pro Ala Lys His Glu Val Arg Phe His Gln Ser Arg Leu Val His Asp
305                 310                 315                 320
Phe Ile Tyr Gln Gly Val Leu Ser Val Leu Gln Gln Gln Thr Glu Thr
                325                 330                 335
Ala Leu Pro Leu Glu Glu Ile Ala Pro Ala Pro Arg His Val Gln Glu
            340                 345                 350
Asn Arg Ile Ala Ala Gly Arg Asn His
        355                 360
```

(2) INFORMATION FOR SEQ ID NO:6:

(i) SEQUENCE CHARACTERISTICS:
        (A) LENGTH: 538 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Met Ser His Ile Ile Glu Leu Pro Glu Met Leu Ala Asn Gln Ile Ala
1               5                   10                  15
Ala Gly Glu Val Ile Glu Arg Pro Ala Ser Val Cys Lys Glu Leu Val
                20                  25                  30
Glu Asn Ala Ile Asp Ala Gly Ser Ser Gln Ile Ile Glu Ile Glu
            35                  40                  45
Glu Ala Gly Leu Lys Lys Val Gln Ile Thr Asp Asn Gly His Gly Ile
        50                  55                  60
Ala His Asp Glu Val Glu Leu Ala Leu Arg Arg His Ala Thr Ser Lys
65                  70                  75                  80
Ile Lys Asn Gln Ala Asp Leu Phe Arg Ile Arg Thr Leu Gly Phe Arg
                85                  90                  95
Gly Glu Ala Leu Pro Ser Ile Ala Ser Val Ser Val Leu Thr Leu Leu
            100                 105                 110
Thr Ala Val Asp Gly Ala Ser His Gly Thr Lys Leu Val Ala Arg Gly
        115                 120                 125
Gly Glu Val Glu Glu Val Ile Pro Ala Thr Ser Pro Val Gly Thr Lys
    130                 135                 140
```

```
Val Cys Val Glu Asp Leu Phe Phe Asn Thr Pro Ala Arg Leu Lys Tyr
145                 150                 155                 160

Met Lys Ser Gln Gln Ala Glu Leu Ser His Ile Ile Asp Ile Val Asn
            165                 170                 175

Arg Leu Gly Leu Ala His Pro Glu Ile Ser Phe Ser Leu Ile Ser Asp
        180                 185                 190

Gly Lys Glu Met Thr Arg Thr Ala Gly Thr Gly Gln Leu Arg Gln Ala
    195                 200                 205

Ile Ala Gly Ile Tyr Gly Leu Val Ser Ala Lys Lys Met Ile Glu Ile
210                 215                 220

Glu Asn Ser Asp Leu Asp Phe Glu Ile Ser Gly Phe Val Ser Leu Pro
225                 230                 235                 240

Glu Leu Thr Arg Ala Asn Arg Asn Tyr Ile Ser Leu Phe Ile Asn Gly
                245                 250                 255

Arg Tyr Ile Lys Asn Phe Leu Leu Asn Arg Ala Ile Leu Asp Gly Phe
            260                 265                 270

Gly Ser Lys Leu Met Val Gly Arg Phe Pro Leu Ala Val Ile His Ile
        275                 280                 285

His Ile Asp Pro Tyr Leu Ala Asp Val Asn Val His Pro Thr Lys Gln
    290                 295                 300

Glu Val Arg Ile Ser Lys Glu Lys Glu Leu Met Thr Leu Val Ser Glu
305                 310                 315                 320

Ala Ile Ala Asn Ser Leu Lys Glu Gln Thr Leu Ile Pro Asp Ala Leu
                325                 330                 335

Glu Asn Leu Ala Lys Ser Thr Val Arg Asn Arg Glu Lys Val Glu Gln
            340                 345                 350

Thr Ile Leu Pro Leu Ser Phe Pro Glu Leu Glu Phe Phe Gly Gln Met
        355                 360                 365

His Gly Thr Tyr Leu Phe Ala Gln Gly Arg Asp Gly Leu Tyr Ile Ile
    370                 375                 380

Asp Gln His Ala Ala Gln Glu Arg Val Lys Tyr Glu Glu Tyr Arg Glu
385                 390                 395                 400

Ser Ile Gly Asn Val Asp Gln Ser Gln Gln Leu Leu Val Pro Tyr
                405                 410                 415

Ile Phe Glu Phe Pro Ala Asp Asp Ala Leu Arg Leu Lys Glu Arg Met
            420                 425                 430

Pro Leu Leu Glu Glu Val Gly Val Phe Leu Ala Glu Tyr Gly Glu Asn
        435                 440                 445

Gln Phe Ile Leu Arg Glu His Pro Ile Trp Met Ala Glu Glu Ile
450                 455                 460

Glu Ser Gly Ile Tyr Glu Met Cys Asp Met Leu Leu Thr Lys Glu
465                 470                 475                 480

Val Ser Ile Lys Lys Tyr Arg Ala Glu Leu Ala Ile Met Met Ser Cys
                485                 490                 495

Lys Arg Ser Ile Lys Ala Asn His Arg Ile Asp Asp His Ser Ala Arg
            500                 505                 510

Gln Leu Leu Tyr Gln Leu Ser Gln Cys Asp Asn Pro Tyr Asn Cys Pro
        515                 520                 525

His Gly Arg Pro Val Leu Val His Phe Thr
    530                 535
```

(2) INFORMATION FOR SEQ ID NO:7:

(i) SEQUENCE CHARACTERISTICS:
(A) LENGTH: 607 amino acids (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:7:

Met Phe His His Ile Glu Asn Leu Leu Ile Glu Thr Glu Lys Arg Cys
1               5                   10                  15

Lys Gln Lys Glu Gln Arg Tyr Ile Pro Val Lys Tyr Leu Phe Ser Met
                20                  25                  30

Thr Gln Ile His Gln Ile Asn Asp Ile Asp Val His Arg Ile Thr Ser
            35                  40                  45

Gly Gln Val Ile Thr Asp Leu Thr Thr Ala Val Lys Glu Leu Val Asp
50                      55                  60

Asn Ser Ile Asp Ala Asn Ala Asn Gln Ile Glu Ile Ile Phe Lys Asp
65                      70                  75                  80

Tyr Gly Leu Glu Ser Ile Glu Cys Ser Asp Asn Gly Asp Gly Ile Asp
                85                  90                  95

Pro Ser Asn Tyr Glu Phe Leu Ala Leu Lys His Tyr Thr Ser Lys Ile
                100                 105                 110

Ala Lys Phe Gln Asp Val Ala Lys Val Gln Thr Leu Gly Phe Arg Gly
            115                 120                 125

Glu Ala Leu Ser Ser Leu Cys Gly Ile Ala Lys Leu Ser Val Ile Thr
130                 135                 140

Thr Thr Ser Pro Pro Lys Ala Asp Lys Glu Leu Tyr Asp Met Val Gly
145                 150                 155                 160

His Ile Thr Ser Lys Thr Thr Thr Ser Arg Asn Lys Gly Thr Thr Val
                165                 170                 175

Leu Val Ser Gln Leu Phe His Asn Leu Pro Val Arg Gln Lys Glu Phe
            180                 185                 190

Ser Lys Thr Phe Lys Arg Gln Phe Thr Lys Cys Leu Thr Val Ile Gln
            195                 200                 205

Gly Tyr Ala Ile Ile Asn Ala Ala Ile Lys Phe Ser Val Trp Asn Ile
            210                 215                 220

Thr Pro Lys Gly Lys Lys Asn Leu Ile Leu Ser Thr Met Arg Asn Ser
225                 230                 235                 240

Ser Met Arg Lys Asn Ile Ser Ser Val Phe Gly Ala Gly Met Arg
                245                 250                 255

Gly Glu Leu Glu Val Asp Leu Val Leu Asp Leu Asn Pro Phe Lys Asn
            260                 265                 270

Arg Met Leu Gly Lys Tyr Thr Asp Asp Pro Asp Phe Leu Asp Leu Asp
            275                 280                 285

Tyr Lys Ile Arg Val Lys Gly Tyr Ile Ser Gln Asn Ser Phe Gly Cys
            290                 295                 300

Gly Arg Asn Ser Lys Asp Arg Gln Phe Ile Tyr Val Asn Lys Arg Pro
305                 310                 315                 320

Val Glu Tyr Ser Thr Leu Leu Lys Cys Cys Asn Glu Val Tyr Lys Thr
                325                 330                 335

Phe Asn Asn Val Gln Phe Pro Ala Val Phe Leu Asn Leu Glu Leu Pro
            340                 345                 350

Met Ser Leu Ile Asp Val Asn Val Thr Pro Asp Lys Arg Val Ile Leu
            355                 360                 365

Leu His Asn Glu Arg Ala Val Ile Asp Ile Phe Lys Thr Thr Leu Ser
370                 375                 380

```
              Asp Tyr Tyr Asn Arg Gln Glu Leu Ala Leu Pro Lys Arg Met Cys Ser
              385                 390                 395                 400

Gln Ser Glu Gln Gln Ala Gln Lys Arg Leu Leu Thr Glu Val Phe Asp
                              405                 410                 415

Asp Asp Phe Lys Lys Met Glu Val Val Gly Gln Phe Asn Leu Gly Phe
                          420                 425                 430

Ile Ile Val Thr Arg Lys Val Asp Asn Lys Ser Asp Leu Phe Ile Val
                      435                 440                 445

Asp Gln His Ala Ser Asp Glu Lys Tyr Asn Phe Glu Thr Leu Gln Ala
                  450                 455                 460

Val Thr Val Phe Lys Ser Gln Lys Leu Ile Ile Pro Gln Pro Val Glu
              465                 470                 475                 480

Leu Ser Val Ile Asp Glu Leu Val Val Leu Asp Asn Leu Pro Val Phe
                              485                 490                 495

Glu Lys Asn Gly Phe Lys Leu Lys Ile Asp Glu Glu Glu Phe Gly
                          500                 505                 510

Ser Arg Val Lys Leu Leu Ser Leu Pro Thr Ser Lys Gln Thr Leu Phe
                      515                 520                 525

Asp Leu Gly Asp Phe Asn Glu Leu Ile His Leu Ile Lys Glu Asp Gly
                  530                 535                 540

Gly Leu Arg Arg Asp Asn Ile Arg Cys Ser Lys Ile Arg Ser Met Phe
              545                 550                 555                 560

Ala Met Arg Ala Cys Arg Ser Ser Ile Met Ile Gly Lys Pro Leu Asn
                              565                 570                 575

Lys Lys Thr Met Thr Arg Val Val His Asn Leu Ser Glu Leu Asp Lys
                          580                 585                 590

Pro Trp Asn Cys Pro His Gly Arg Pro Thr Met Arg His Leu Met
                      595                 600                 605

(2) INFORMATION FOR SEQ ID NO:8:

(i) SEQUENCE CHARACTERISTICS:
         (A) LENGTH: 2484 base pairs
         (B) TYPE: nucleic acid
         (C) STRANDEDNESS: single
         (D) TOPOLOGY: linear (ii) MOLECULE TYPE: cDNA (viii) POSITION IN GENOME:
         (B) MAP POSITION: 3p21.3-23

(xi) SEQUENCE DESCRIPTION: SEQ ID NO:8:

CTTGGCTCTT CTGGCGCCAA AATGTCGTTC GTGGCAGGGG TTATTCGGCG GCTGGACGAG       60

ACAGTGGTGA ACCGCATCGC GGCGGGGGAA GTTATCCAGC GGCCAGCTAA TGCTATCAAA      120

GAGATGATTG AGAACTGTTT AGATGCAAAA TCCACAAGTA TTCAAGTGAT TGTTAAAGAG      180

GGAGGCCTGA AGTTGATTCA GATCCAAGAC AATGGCACCG GGATCAGGAA AGAAGATCTG      240

GATATTGTAT GTGAAAGGTT CACTACTAGT AAACTGCAGT CCTTTGAGGA TTTAGCCAGT      300

ATTTCTACCT ATGGCTTTCG AGGTGAGGCT TTGGCCAGCA TAAGCCATGT GGCTCATGTT      360

ACTATTACAA CGAAAACAGC TGATGGAAAG TGTGCATACA GAGCAAGTTA CTCAGATGGA      420

AAACTGAAAG CCCCTCCTAA ACCATGTGCT GGCAATCAAG GACCCAGAT CACGGTGGAG       480

GACCTTTTTT ACAACATAGC CACGAGGAGA AAAGCTTTAA AAAATCCAAG TGAAGAATAT      540

GGGAAAATTT TGGAAGTTGT TGGCAGGTAT TCAGTACACA ATGCAGGCAT TAGTTTCTCA      600

GTTAAAAAAC AAGGAGAGAC AGTAGCTGAT GTTAGGACAC TACCCAATGC CTCAACCGTG      660
```

| | | | | |
|---|---|---|---|---|
| GACAATATTC | GCTCCATCTT | TGGAAATGCT | GTTAGTCGAG AACTGATAGA | AATTGGATGT | 720 |
| GAGGATAAAA | CCCTAGCCTT | CAAAATGAAT | GGTTACATAT CCAATGCAAA | CTACTCAGTG | 780 |
| AAGAAGTGCA | TCTTCTTACT | CTTCATCAAC | CATCGTCTGG TAGAATCAAC | TTCCTTGAGA | 840 |
| AAAGCCATAG | AAACAGTGTA | TGCAGCCTAT | TTGCCCAAAA ACACACACCC | ATTCCTGTAC | 900 |
| CTCAGTTTAG | AAATCAGTCC | CCAGAATGTG | GATGTTAATG TGCACCCCAC | AAAGCATGAA | 960 |
| GTTCACTTCC | TGCACGAGGA | GAGCATCCTG | GAGCGGGTGC AGCAGCACAT | CGAGAGCAAG | 1020 |
| CTCCTGGGCT | CCAATTCCTC | CAGGATGTAC | TTCACCCAGA CTTTGCTACC | AGGACTTGCT | 1080 |
| GGCCCCTCTG | GGGAGATGGT | TAAATCCACA | ACAAGTCTGA CCTCGTCTTC | TACTTCTGGA | 1140 |
| AGTAGTGATA | AGGTCTATGC | CCACCAGATG | GTTCGTACAG ATTCCCGGGA | ACAGAAGCTT | 1200 |
| GATGCATTTC | TGCAGCCTCT | GAGCAAACCC | CTGTCCAGTC AGCCCCAGGC | CATTGTCACA | 1260 |
| GAGGATAAGA | CAGATATTTC | TAGTGGCAGG | GCTAGGCAGC AAGATGAGGA | GATGCTTGAA | 1320 |
| CTCCCAGCCC | CTGCTGAAGT | GGCTGCCAAA | AATCAGAGCT TGGAGGGGGA | TACAACAAAG | 1380 |
| GGGACTTCAG | AAATGTCAGA | GAAGAGAGGA | CCTACTTCCA GCAACCCCAG | AAAGAGACAT | 1440 |
| CGGGAAGATT | CTGATGTGGA | AATGGTGGAA | GATGATTCCC GAAAGGAAAT | GACTGCAGCT | 1500 |
| TGTACCCCCC | GGAGAAGGAT | CATTAACCTC | ACTAGTGTTT TGAGTCTCCA | GGAAGAAATT | 1560 |
| AATGAGCAGG | GACATGAGGT | TCTCCGGGAG | ATGTTGCATA ACCACTCCTT | CGTGGGCTGT | 1620 |
| GTGAATCCTC | AGTGGGCCTT | GGCACAGCAT | CAAACCAAGT TATACCTTCT | CAACACCACC | 1680 |
| AAGCTTAGTG | AAGAACTGTT | CTACCAGATA | CTCATTTATG ATTTTGCCAA | TTTTGGTGTT | 1740 |
| CTCAGGTTAT | CGGAGCCAGC | ACCGCTCTTT | GACCTTGCCA TGCTTGCCTT | AGATAGTCCA | 1800 |
| GAGAGTGGCT | GGACAGAGGA | AGATGGTCCC | AAAGAAGGAC TTGCTGAATA | CATTGTTGAG | 1860 |
| TTTCTGAAGA | AGAAGGCTGA | GATGCTTGCA | GACTATTTCT CTTTGGAAAT | TGATGAGGAA | 1920 |
| GGGAACCTGA | TTGGATTACC | CCTTCTGATT | GACAACTATG TGCCCCCTTT | GGAGGGACTG | 1980 |
| CCTATCTTCA | TTCTTCGACT | AGCCACTGAG | GTGAATTGGG ACGAAGAAAA | GGAATGTTTT | 2040 |
| GAAAGCCTCA | GTAAAGAATG | CGCTATGTTC | TATTCCATCC GGAAGCAGTA | CATATCTGAG | 2100 |
| GAGTCGACCC | TCTCAGGCCA | GCAGAGTGAA | GTGCCTGGCT CCATTCCAAA | CTCCTGGAAG | 2160 |
| TGGACTGTGG | AACACATTGT | CTATAAAGCC | TTGCGCTCAC ACATTCTGCC | TCCTAAACAT | 2220 |
| TTCACAGAAG | ATGGAAATAT | CCTGCAGCTT | GCTAACCTGC CTGATCTATA | CAAAGTCTTT | 2280 |
| GAGAGGTGTT | AAATATGGTT | ATTTATGCAC | TGTGGGATGT GTTCTTCTTT | CTCTGTATTC | 2340 |
| CGATACAAAG | TGTTGTATCA | AAGTGTGATA | TACAAAGTGT ACCAACATAA | GTGTTGGTAG | 2400 |
| CACTTAAGAC | TTATACTTGC | CTTCTGATAG | TATTCCTTTA TACACAGTGG | ATTGATTATA | 2460 |
| AATAAATAGA | TGTGTCTTAA | CATA | | | 2484 |

(2) INFORMATION FOR SEQ ID NO:9:

(i) SEQUENCE CHARACTERISTICS:
        (A) LENGTH: 756 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
Met Ser Phe Val Ala Gly Val Ile Arg Arg Leu Asp Glu Thr Val Val
 1               5                  10                  15

Asn Arg Ile Ala Ala Gly Glu Val Ile Gln Arg Pro Ala Asn Ala Ile
                20                  25                  30
```

-continued

```
Lys Glu Met Ile Glu Asn Cys Leu Asp Ala Lys Ser Thr Ser Ile Gln
        35                  40                  45
Val Ile Val Lys Glu Gly Gly Leu Lys Leu Ile Gln Ile Gln Asp Asn
    50                  55                  60
Gly Thr Gly Ile Arg Lys Glu Asp Leu Asp Ile Val Cys Glu Arg Phe
65                  70                  75                  80
Thr Thr Ser Lys Leu Gln Ser Phe Glu Asp Leu Ala Ser Ile Ser Thr
                85                  90                  95
Tyr Gly Phe Arg Gly Glu Ala Leu Ala Ser Ile Ser His Val Ala His
                100                 105                 110
Val Thr Ile Thr Thr Lys Thr Ala Asp Gly Lys Cys Ala Tyr Arg Ala
            115                 120                 125
Ser Tyr Ser Asp Gly Lys Leu Lys Ala Pro Pro Lys Pro Cys Ala Gly
        130                 135                 140
Asn Gln Gly Thr Gln Ile Thr Val Glu Asp Leu Phe Tyr Asn Ile Ala
145                 150                 155                 160
Thr Arg Arg Lys Ala Leu Lys Asn Pro Ser Glu Glu Tyr Gly Lys Ile
                165                 170                 175
Leu Glu Val Val Gly Arg Tyr Ser Val His Asn Ala Gly Ile Ser Phe
                180                 185                 190
Ser Val Lys Lys Gln Gly Glu Thr Val Ala Asp Val Arg Thr Leu Pro
            195                 200                 205
Asn Ala Ser Thr Val Asp Asn Ile Arg Ser Ile Phe Gly Asn Ala Val
        210                 215                 220
Ser Arg Glu Leu Ile Glu Ile Gly Cys Glu Asp Lys Thr Leu Ala Phe
225                 230                 235                 240
Lys Met Asn Gly Tyr Ile Ser Asn Ala Asn Tyr Ser Val Lys Lys Cys
                245                 250                 255
Ile Phe Leu Leu Phe Ile Asn His Arg Leu Val Glu Ser Thr Ser Leu
                260                 265                 270
Arg Lys Ala Ile Glu Thr Val Tyr Ala Ala Tyr Leu Pro Lys Asn Thr
            275                 280                 285
His Pro Phe Leu Tyr Leu Ser Leu Glu Ile Ser Pro Gln Asn Val Asp
        290                 295                 300
Val Asn Val His Pro Thr Lys His Glu Val His Phe Leu His Glu Glu
305                 310                 315                 320
Ser Ile Leu Glu Arg Val Gln Gln His Ile Glu Ser Lys Leu Leu Gly
                325                 330                 335
Ser Asn Ser Ser Arg Met Tyr Phe Thr Gln Thr Leu Leu Pro Gly Leu
                340                 345                 350
Ala Gly Pro Ser Gly Glu Met Val Lys Ser Thr Thr Ser Leu Thr Ser
            355                 360                 365
Ser Ser Thr Ser Gly Ser Ser Asp Lys Val Tyr Ala His Gln Met Val
        370                 375                 380
Arg Thr Asp Ser Arg Glu Gln Lys Leu Asp Ala Phe Leu Gln Pro Leu
385                 390                 395                 400
Ser Lys Pro Leu Ser Ser Gln Pro Gln Ala Ile Val Thr Glu Asp Lys
                405                 410                 415
Thr Asp Ile Ser Ser Gly Arg Ala Arg Gln Gln Asp Glu Glu Met Leu
                420                 425                 430
Glu Leu Pro Ala Pro Ala Glu Val Ala Ala Lys Asn Gln Ser Leu Glu
            435                 440                 445
Gly Asp Thr Thr Lys Gly Thr Ser Glu Met Ser Glu Lys Arg Gly Pro
```

|   |   |   |   |   | 450 |   |   |   |   | 455 |   |   |   |   | 460 |   |   |
|---|---|---|---|---|---|---|---|---|---|---|---|---|---|---|---|---|---|

Thr Ser Ser Asn Pro Arg Lys Arg His Arg Glu Asp Ser Asp Val Glu
465                 470                 475                 480

Met Val Glu Asp Asp Ser Arg Lys Glu Met Thr Ala Ala Cys Thr Pro
            485                 490                 495

Arg Arg Arg Ile Ile Asn Leu Thr Ser Val Leu Ser Leu Gln Glu Glu
            500                 505                 510

Ile Asn Glu Gln Gly His Glu Val Leu Arg Glu Met Leu His Asn His
            515                 520                 525

Ser Phe Val Gly Cys Val Asn Pro Gln Trp Ala Leu Ala Gln His Gln
530                 535                 540

Thr Lys Leu Tyr Leu Leu Asn Thr Thr Lys Leu Ser Glu Glu Leu Phe
545                 550                 555                 560

Tyr Gln Ile Leu Ile Tyr Asp Phe Ala Asn Phe Gly Val Leu Arg Leu
            565                 570                 575

Ser Glu Pro Ala Pro Leu Phe Asp Leu Ala Met Leu Ala Leu Asp Ser
            580                 585                 590

Pro Glu Ser Gly Trp Thr Glu Glu Asp Gly Pro Lys Glu Gly Leu Ala
            595                 600                 605

Glu Tyr Ile Val Glu Phe Leu Lys Lys Ala Glu Met Leu Ala Asp
610                 615                 620

Tyr Phe Ser Leu Glu Ile Asp Glu Glu Gly Asn Leu Ile Gly Leu Pro
625                 630                 635                 640

Leu Leu Ile Asp Asn Tyr Val Pro Pro Leu Glu Gly Leu Pro Ile Phe
            645                 650                 655

Ile Leu Arg Leu Ala Thr Glu Val Asn Trp Asp Glu Glu Lys Glu Cys
            660                 665                 670

Phe Glu Ser Leu Ser Lys Glu Cys Ala Met Phe Tyr Ser Ile Arg Lys
            675                 680                 685

Gln Tyr Ile Ser Glu Glu Ser Thr Leu Ser Gly Gln Gln Ser Glu Val
            690                 695                 700

Pro Gly Ser Ile Pro Asn Ser Trp Lys Trp Thr Val Glu His Ile Val
705                 710                 715                 720

Tyr Lys Ala Leu Arg Ser His Ile Leu Pro Pro Lys His Phe Thr Glu
            725                 730                 735

Asp Gly Asn Ile Leu Gln Leu Ala Asn Leu Pro Asp Leu Tyr Lys Val
            740                 745                 750

Phe Glu Arg Cys
            755

(2) INFORMATION FOR SEQ ID NO:10:

(i) SEQUENCE CHARACTERISTICS:
        (A) LENGTH: 361 base pairs
        (B) TYPE: nucleic acid
        (C) STRANDEDNESS: single
        (D) TOPOLOGY: linear (ii) MOLECULE TYPE: cDNA (viii) POSITION IN GENOME:
        (B) MAP POSITION: 3p21.3-23

(xi) SEQUENCE DESCRIPTION: SEQ ID NO:10:

```
TTAATGAGGC ACTATTGTTT GTATTTGGAG TTTGTTATCA TTGCTTGGCT CATATTAAAA      60

TATGTACATT AGAGTAGTTG CAGACTGATA AATTATTTTC TGTTTGATTT GCCAGTTTAG     120

ATGCAAAATC CACAAGTATT CAAGTGATTG TTAAAGAGGG AGGCCTGAAG TTGATTCAGA     180
```

-continued

```
TCCAAGACAA TGGCACCGGG ATCAGGGTAA GTAAAACCTC AAAGTAGCAG GATGTTTGTG      240

CGCTTCATGG AAGAGTCAGG ACCTTTCTCT GTTCTGGAAA CTAGGCTTTT GCAGATGGGA      300

TTTTTTCACT GAAAAATTCA ACACCAACAA TAAATATTTA TTGAGTACCT ATTATTTGCG      360

G                                                                    361
```

(2) INFORMATION FOR SEQ ID NO:11:

(i) SEQUENCE CHARACTERISTICS:
        (A) LENGTH: 341 amino acids
        (B) TYPE: amino acid
        (C) STRANDEDNESS: single
        (D) TOPOLOGY: linear (ii) MOLECULE TYPE: cDNA (viii) POSITION IN GENOME:
        (B) MAP POSITION: 3p21.3-23

(xi) SEQUENCE DESCRIPTION: SEQ ID NO:11:

```
Gly Ala Ala Thr Thr Cys Ala Ala Gly Ala Gly Ala Thr Thr Thr
 1               5                  10                  15

Gly Gly Ala Ala Ala Ala Thr Gly Ala Gly Thr Ala Ala Cys Ala Thr
            20                  25                  30

Gly Ala Thr Thr Ala Thr Thr Thr Ala Cys Thr Cys Ala Thr Cys Thr
        35                  40                  45

Thr Thr Thr Thr Gly Gly Thr Ala Thr Cys Thr Ala Ala Cys Ala Ala
    50                  55                  60

Ala Ala Gly Ala Ala Gly Ala Thr Cys Thr Gly Gly Ala Thr Ala Thr
65                  70                  75                  80

Thr Gly Thr Ala Thr Gly Thr Gly Ala Ala Ala Gly Gly Lys Thr Cys
                85                  90                  95

Ala Cys Thr Ala Cys Thr Ala Gly Thr Ala Ala Cys Thr Gly Cys
            100                 105                 110

Ala Gly Thr Cys Cys Thr Thr Thr Gly Ala Gly Gly Ala Asp Thr Thr
            115                 120                 125

Thr Ala Gly Cys Cys Ala Gly Thr Ala Thr Thr Thr Cys Thr Ala Cys
    130                 135                 140

Cys Thr Ala Thr Gly Gly Cys Thr Thr Thr Cys Gly Ala Gly Gly Thr
145                 150                 155                 160

Gly Ala Gly Gly Thr Ala Ala Gly Cys Thr Ala Ala Gly Ala Thr
                165                 170                 175

Thr Cys Ala Ala Gly Ala Ala Ala Thr Gly Thr Lys Thr Ala Ala Ala
            180                 185                 190

Ala Thr Ala Thr Cys Cys Thr Cys Cys Thr Gly Thr Gly Ala Thr Gly
        195                 200                 205

Ala Cys Ala Thr Thr Gly Thr Tyr Thr Gly Thr Cys Ala Thr Thr Thr
    210                 215                 220

Gly Thr Thr Ala Gly Thr Ala Thr Gly Thr Ala Thr Thr Cys Thr
225                 230                 235                 240

Cys Ala Ala Cys Ala Thr Ala Gly Ala Thr Ala Ala Thr Ala Ala
                245                 250                 255

Gly Gly Thr Thr Thr Gly Gly Thr Ala Cys Cys Thr Thr Thr Ala
            260                 265                 270

Cys Thr Thr Gly Thr Thr Ala Ala Ala Thr Gly Thr Ala Thr Gly Cys
        275                 280                 285

Ala Ala Ala Thr Gly Thr Ala Thr Gly Cys Ala Ala Ala Thr Cys Thr
```

```
                    290                 295                 300

Gly His Gly Cys Ala Ala Ala Cys Thr Thr Ala Ala Thr Gly Ala Asp
        305                 310                 315                 320

Cys Thr Thr Thr Ala Ala Cys Thr Thr Cys Ala Ala Ala Gly Ala
                            325                 330                 335

Cys Thr Gly Ala Gly
                    340
```

(2) INFORMATION FOR SEQ ID NO:12:

(i) SEQUENCE CHARACTERISTICS:
        (A) LENGTH: 756 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

```
        Met Ser Phe Val Ala Gly Val Ile Arg Arg Leu Asp Glu Thr Val Val
        1               5                   10                  15

Asn Arg Ile Ala Ala Gly Glu Val Ile Gln Arg Pro Ala Asn Ala Ile
                        20                  25                  30

Lys Glu Met Ile Glu Asn Cys Leu Asp Ala Lys Ser Thr Ser Ile Gln
                    35                  40                  45

Val Ile Val Lys Glu Gly Gly Leu Lys Leu Ile Gln Ile Gln Asp Asn
        50                  55                  60

Gly Thr Gly Ile Arg Lys Glu Asp Leu Asp Ile Val Cys Glu Arg Phe
        65                  70                  75                  80

Thr Thr Ser Lys Leu Gln Ser Phe Glu Asp Leu Ala Ser Ile Ser Thr
                        85                  90                  95

Tyr Gly Phe Arg Gly Glu Ala Leu Ala Ser Ile Ser His Val Ala His
                    100                 105                 110

Val Thr Ile Thr Thr Lys Thr Ala Asp Gly Lys Cys Ala Tyr Arg Ala
                    115                 120                 125

Ser Tyr Ser Asp Gly Lys Leu Lys Ala Pro Pro Lys Pro Cys Ala Gly
        130                 135                 140

Asn Gln Gly Thr Gln Ile Thr Val Glu Asp Leu Phe Tyr Asn Ile Ala
        145                 150                 155                 160

Thr Arg Arg Lys Ala Leu Lys Asn Pro Ser Glu Glu Tyr Gly Lys Ile
                        165                 170                 175

Leu Glu Val Val Gly Arg Tyr Ser Val His Asn Ala Gly Ile Ser Phe
                    180                 185                 190

Ser Val Lys Lys Gln Gly Glu Thr Val Ala Asp Val Arg Thr Leu Pro
                    195                 200                 205

Asn Ala Ser Thr Val Asp Asn Ile Arg Ser Ile Phe Gly Asn Ala Val
        210                 215                 220

Ser Arg Glu Leu Ile Glu Ile Gly Cys Glu Asp Lys Thr Leu Ala Phe
        225                 230                 235                 240

Lys Met Asn Gly Tyr Ile Ser Asn Ala Asn Tyr Ser Val Lys Lys Cys
                        245                 250                 255

Ile Phe Leu Leu Phe Ile Asn His Arg Leu Val Glu Ser Thr Ser Leu
                    260                 265                 270

Arg Lys Ala Ile Glu Thr Val Tyr Ala Ala Tyr Leu Pro Lys Asn Thr
                    275                 280                 285

His Pro Phe Leu Tyr Leu Ser Leu Glu Ile Ser Pro Gln Asn Val Asp
                    290                 295                 300
```

```
Val Asn Val His Pro Thr Lys His Glu Val His Phe Leu His Glu Glu
305                 310                 315                 320

Ser Ile Leu Glu Arg Val Gln Gln His Ile Glu Ser Lys Leu Leu Gly
            325                 330                 335

Ser Asn Ser Ser Arg Met Tyr Phe Thr Gln Thr Leu Leu Pro Gly Leu
                340                 345                 350

Ala Gly Pro Ser Gly Glu Met Val Lys Ser Thr Thr Ser Leu Thr Ser
            355                 360                 365

Ser Ser Thr Ser Gly Ser Ser Asp Lys Val Tyr Ala His Gln Met Val
        370                 375                 380

Arg Thr Asp Ser Arg Glu Gln Lys Leu Asp Ala Phe Leu Gln Pro Leu
385                 390                 395                 400

Ser Lys Pro Leu Ser Ser Gln Pro Gln Ala Ile Val Thr Glu Asp Lys
                405                 410                 415

Thr Asp Ile Ser Ser Gly Arg Ala Arg Gln Gln Asp Glu Glu Met Leu
            420                 425                 430

Glu Leu Pro Ala Pro Ala Glu Val Ala Ala Lys Asn Gln Ser Leu Glu
            435                 440                 445

Gly Asp Thr Thr Lys Gly Thr Ser Glu Met Ser Glu Lys Arg Gly Pro
450                 455                 460

Thr Ser Ser Asn Pro Arg Lys Arg His Arg Glu Asp Ser Asp Val Glu
465                 470                 475                 480

Met Val Glu Asp Asp Ser Arg Lys Glu Met Thr Ala Ala Cys Thr Pro
                485                 490                 495

Arg Arg Arg Ile Ile Asn Leu Thr Ser Val Leu Ser Leu Gln Glu Glu
                500                 505                 510

Ile Asn Glu Gln Gly His Glu Val Leu Arg Glu Met Leu His Asn His
            515                 520                 525

Ser Phe Val Gly Cys Val Asn Pro Gln Trp Ala Leu Ala Gln His Gln
            530                 535                 540

Thr Lys Leu Tyr Leu Leu Asn Thr Thr Lys Leu Ser Glu Glu Leu Phe
545                 550                 555                 560

Tyr Gln Ile Leu Ile Tyr Asp Phe Ala Asn Phe Gly Val Leu Arg Leu
                565                 570                 575

Ser Glu Pro Ala Pro Leu Phe Asp Leu Ala Met Leu Ala Leu Asp Ser
            580                 585                 590

Pro Glu Ser Gly Trp Thr Glu Glu Asp Gly Pro Lys Glu Gly Leu Ala
            595                 600                 605

Glu Tyr Ile Val Glu Phe Leu Lys Lys Ala Glu Met Leu Ala Asp
    610                 615                 620

Tyr Phe Ser Leu Glu Ile Asp Glu Glu Gly Asn Leu Ile Gly Leu Pro
625                 630                 635                 640

Leu Leu Ile Asp Asn Tyr Val Pro Pro Leu Glu Gly Leu Pro Ile Phe
                645                 650                 655

Ile Leu Arg Leu Ala Thr Glu Val Asn Trp Asp Glu Glu Lys Glu Cys
                660                 665                 670

Phe Glu Ser Leu Ser Lys Glu Cys Ala Met Phe Tyr Ser Ile Arg Lys
                675                 680                 685

Gln Tyr Ile Ser Glu Glu Ser Thr Leu Ser Gly Gln Gln Ser Glu Val
            690                 695                 700

Pro Gly Ser Ile Pro Asn Ser Trp Lys Trp Thr Val Glu His Ile Val
705                 710                 715                 720

Tyr Lys Ala Leu Arg Ser His Ile Leu Pro Pro Lys His Phe Thr Glu
```

```
                       725                 730                    735
       Asp Gly Asn Ile Leu Gln Leu Ala Asn Leu Pro Asp Leu Tyr Lys Val
                       740                 745                    750

Phe Glu Arg Cys
              755
```

(2) INFORMATION FOR SEQ ID NO:13:

(i) SEQUENCE CHARACTERISTICS:
        (A) LENGTH: 770 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

```
       Met Ser Leu Arg Ile Lys Ala Leu Asp Ala Ser Val Val Asn Lys Ile
       1               5                  10                      15

Ala Ala Gly Glu Ile Ile Ile Ser Pro Val Asn Ala Leu Lys Glu Met
                       20                 25                      30

Met Glu Asn Ser Ile Asp Ala Asn Ala Thr Met Ile Asp Ile Leu Val
                       35                 40                 45

Lys Glu Gly Gly Ile Lys Val Leu Gln Ile Thr Asp Asn Gly Ser Gly
       50                  55                 60

Ile Asn Lys Ala Asp Leu Pro Ile Leu Cys Glu Arg Phe Thr Thr Ser
       65                  70                 75                      80

Lys Leu Gln Lys Phe Glu Asp Leu Ser Gln Ile Gln Thr Tyr Gly Phe
                       85                 90                      95

Arg Gly Glu Ala Leu Ala Ser Ile Ser His Val Ala Arg Val Thr Val
                       100                105                     110

Thr Thr Lys Val Lys Glu Asp Arg Cys Ala Trp Arg Val Ser Tyr Ala
                       115                120                125

Glu Gly Lys Met Leu Glu Ser Pro Lys Pro Val Ala Gly Lys Asp Gly
                       130                135                140

Thr Thr Ile Leu Val Glu Asp Leu Phe Phe Asn Ile Pro Ser Arg Leu
       145                 150                155                     160

Arg Ala Leu Arg Ser His Asn Asp Glu Tyr Ser Lys Ile Leu Asp Val
                       165                170                     175

Val Gly Arg Tyr Ala Ile His Ser Lys Asp Ile Gly Phe Ser Cys Lys
                       180                185                190

Lys Phe Gly Asp Ser Asn Tyr Ser Leu Ser Val Lys Pro Ser Tyr Thr
                       195                200                205

Val Gln Asp Arg Ile Arg Thr Val Phe Asn Lys Ser Val Ala Ser Asn
                       210                215                220

Leu Ile Thr Phe His Ile Ser Lys Val Glu Asp Leu Asn Leu Glu Ser
       225                 230                235                     240

Val Asp Gly Lys Val Cys Asn Leu Asn Phe Ile Ser Lys Lys Ser Ile
                       245                250                255

Ser Leu Ile Phe Phe Ile Asn Asn Arg Leu Val Thr Cys Asp Leu Leu
                       260                265                270

Arg Arg Ala Leu Asn Ser Val Tyr Ser Asn Tyr Leu Pro Lys Gly Phe
                       275                280                285

Arg Pro Phe Ile Tyr Leu Gly Ile Val Ile Asp Pro Ala Ala Val Asp
                       290                295                300

Val Asn Val His Pro Thr Lys Arg Glu Val Arg Phe Leu Ser Gln Asp
       305                 310                315                     320
```

-continued

```
Glu Ile Ile Glu Lys Ile Ala Asn Gln Leu His Ala Glu Leu Ser Ala
                325                 330                 335

Ile Asp Thr Ser Arg Thr Phe Lys Ala Ser Ser Ile Ser Thr Asn Lys
            340                 345                 350

Pro Glu Ser Leu Ile Pro Phe Asn Asp Thr Ile Glu Ser Asp Arg Asn
            355                 360                 365

Arg Lys Ser Leu Arg Gln Ala Gln Val Val Glu Asn Ser Tyr Thr Thr
    370                 375                 380

Ala Asn Ser Gln Leu Arg Lys Ala Lys Arg Gln Glu Asn Lys Leu Val
385                 390                 395                 400

Arg Ile Asp Ala Ser Gln Ala Lys Ile Thr Ser Phe Leu Ser Ser Ser
                405                 410                 415

Gln Gln Phe Asn Phe Glu Gly Ser Ser Thr Lys Arg Gln Leu Ser Glu
                420                 425                 430

Pro Lys Val Thr Asn Val Ser His Ser Gln Glu Ala Glu Lys Leu Thr
            435                 440                 445

Leu Asn Glu Ser Glu Gln Pro Arg Asp Ala Asn Thr Ile Asn Asp Asn
    450                 455                 460

Asp Leu Lys Asp Gln Pro Lys Lys Gln Lys Gln Leu Gly Asp Tyr
465                 470                 475                 480

Lys Val Pro Ser Ile Ala Asp Asp Glu Lys Asn Ala Leu Pro Ile Ser
                485                 490                 495

Lys Asp Gly Tyr Ile Arg Val Pro Lys Glu Arg Val Asn Val Asn Leu
            500                 505                 510

Thr Ser Ile Lys Lys Leu Arg Glu Lys Val Asp Asp Ser Ile His Arg
            515                 520                 525

Glu Leu Thr Asp Ile Phe Ala Asn Leu Asn Tyr Val Gly Val Val Asp
    530                 535                 540

Glu Glu Arg Arg Leu Ala Ala Ile Gln His Asp Leu Lys Leu Phe Leu
545                 550                 555                 560

Ile Asp Tyr Gly Ser Val Cys Tyr Glu Leu Phe Tyr Gln Ile Gly Leu
                565                 570                 575

Thr Asp Phe Ala Asn Phe Gly Lys Ile Asn Leu Gln Ser Thr Asn Val
            580                 585                 590

Ser Asp Asp Ile Val Leu Tyr Asn Leu Leu Ser Glu Phe Asp Glu Leu
            595                 600                 605

Asn Asp Asp Ala Ser Lys Glu Lys Ile Ile Ser Lys Ile Trp Asp Met
    610                 615                 620

Ser Ser Met Leu Asn Glu Tyr Tyr Ser Ile Glu Leu Val Asn Asp Gly
625                 630                 635                 640

Leu Asp Asn Asp Leu Lys Ser Val Lys Leu Lys Ser Leu Pro Leu Leu
                645                 650                 655

Leu Lys Gly Tyr Ile Pro Ser Leu Val Lys Leu Pro Phe Phe Ile Tyr
            660                 665                 670

Arg Leu Gly Lys Glu Val Asp Trp Glu Asp Glu Gln Glu Cys Leu Asp
            675                 680                 685

Gly Ile Leu Arg Glu Ile Ala Leu Leu Tyr Ile Pro Asp Met Val Pro
    690                 695                 700

Lys Val Asp Thr Leu Asp Ala Ser Leu Ser Glu Asp Glu Lys Ala Gln
705                 710                 715                 720

Phe Ile Asn Arg Lys Glu His Ile Ser Ser Leu Leu Glu His Val Leu
                725                 730                 735

Phe Pro Cys Ile Lys Arg Arg Phe Leu Ala Pro Arg His Ile Leu Lys
```

```
                    740              745              750
    Asp Val Val Glu Ile Ala Asn Leu Pro Asp Leu Tyr Lys Val Phe Glu
            755              760              765

Arg Cys
        770
```

(2) INFORMATION FOR SEQ ID NO:14:

(i) SEQUENCE CHARACTERISTICS:
        (A) LENGTH: 64 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

```
    Val Asn Arg Ile Ala Ala Gly Glu Val Ile Gln Arg Pro Ala Asn Ala
    1               5                   10                  15

Ile Lys Glu Met Ile Glu Asn Cys Leu Asp Ala Lys Phe Thr Ser Ile
                20                  25                  30

Gln Val Ile Val Lys Glu Gly Gly Leu Lys Leu Ile Gln Ile Gln Asp
            35                  40                  45

Asn Gly Thr Gly Ile Arg Lys Glu Asp Leu Asp Ile Val Cys Glu Arg
        50                  55                  60
```

(2) INFORMATION FOR SEQ ID NO:15:

(i) SEQUENCE CHARACTERISTICS:
        (A) LENGTH: 64 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:15:

```
    Val Asn Arg Ile Ala Ala Gly Glu Val Ile Gln Arg Pro Ala Asn Ala
    1               5                   10                  15

Ile Lys Glu Met Ile Glu Asn Cys Leu Asp Ala Lys Ser Thr Ser Ile
                20                  25                  30

Gln Val Ile Val Lys Glu Gly Gly Leu Lys Leu Ile Gln Ile Gln Asp
            35                  40                  45

Asn Gly Thr Gly Ile Arg Lys Glu Asp Leu Asp Ile Val Cys Glu Arg
        50                  55                  60
```

(2) INFORMATION FOR SEQ ID NO:16:

(i) SEQUENCE CHARACTERISTICS:
        (A) LENGTH: 52 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

```
    Pro Ala Asn Ala Ile Lys Glu Met Ile Glu Asn Cys Leu Asp Ala Lys
    1               5                   10                  15

Ser Thr Asn Ile Gln Val Val Lys Glu Gly Gly Leu Lys Leu Ile
                20                  25                  30

Gln Ile Gln Asp Asn Gly Thr Gly Ile Arg Lys Glu Asp Leu Asp Ile
            35                  40                  45
```

-continued

```
       Val Cys Glu Arg
                 50
```

(2) INFORMATION FOR SEQ ID NO:17:

(i) SEQUENCE CHARACTERISTICS:
        (A) LENGTH: 64 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

```
   Val Asn Lys Ile Ala Ala Gly Glu Ile Ile Ile Ser Pro Val Asn Ala
   1               5                  10                  15

Leu Lys Glu Met Met Glu Asn Ser Ile Asp Ala Asn Ala Thr Met Ile
                  20                  25                  30

Asp Ile Leu Val Lys Glu Gly Gly Ile Lys Val Leu Gln Ile Thr Asp
                  35                  40                  45

Asn Gly Ser Gly Ile Asn Lys Ala Asp Leu Pro Ile Leu Cys Glu Arg
              50                  55                  60
```

(2) INFORMATION FOR SEQ ID NO:18:

(i) SEQUENCE CHARACTERISTICS:
        (A) LENGTH: 64 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:18:

```
   Val His Arg Ile Thr Ser Gly Gln Val Ile Thr Asp Leu Thr Thr Ala
   1               5                  10                  15

Val Lys Glu Leu Val Asp Asn Ser Ile Asp Ala Asn Ala Asn Gln Ile
                  20                  25                  30

Glu Ile Ile Phe Lys Asp Tyr Gly Leu Glu Ser Ile Glu Cys Ser Asp
                  35                  40                  45

Asn Gly Asp Gly Ile Asp Pro Ser Asn Tyr Glu Phe Leu Ala Leu Lys
              50                  55                  60
```

(2) INFORMATION FOR SEQ ID NO:19:

(i) SEQUENCE CHARACTERISTICS:
        (A) LENGTH: 64 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:19:

```
   Ala Asn Gln Ile Ala Ala Gly Glu Val Val Glu Arg Pro Ala Ser Val
   1               5                  10                  15

Val Lys Glu Leu Val Glu Asn Ser Leu Asp Ala Gly Ala Thr Arg Ile
                  20                  25                  30

Asp Ile Asp Ile Glu Arg Gly Gly Ala Lys Leu Ile Arg Ile Arg Asp
                  35                  40                  45

Asn Gly Cys Gly Ile Lys Lys Asp Glu Leu Ala Leu Ala Leu Ala Arg
              50                  55                  60
```

(2) INFORMATION FOR SEQ ID NO:20:

(i) SEQUENCE CHARACTERISTICS:
    (A) LENGTH: 64 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:20:

```
Ala Asn Gln Ile Ala Ala Gly Glu Val Val Glu Arg Pro Ala Ser Val
 1               5                  10                  15

Val Lys Glu Leu Val Glu Asn Ser Leu Asp Ala Gly Ala Thr Arg Val
            20                  25                  30

Asp Ile Asp Ile Glu Arg Gly Gly Ala Lys Leu Ile Arg Ile Arg Asp
        35                  40                  45

Asn Gly Cys Gly Ile Lys Lys Glu Glu Leu Ala Leu Ala Leu Ala Arg
    50                  55                  60
```

(2) INFORMATION FOR SEQ ID NO:21:

(i) SEQUENCE CHARACTERISTICS:
        (A) LENGTH: 64 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:21:

```
Ala Asn Gln Ile Ala Ala Gly Glu Val Ile Glu Arg Pro Ala Ser Val
 1               5                  10                  15

Cys Lys Glu Leu Val Glu Asn Ala Ile Asp Ala Gly Ser Ser Gln Ile
            20                  25                  30

Ile Ile Glu Ile Glu Glu Ala Gly Leu Lys Lys Val Gln Ile Thr Asp
        35                  40                  45

Asn Gly His Gly Ile Ala His Asp Glu Val Glu Leu Ala Leu Arg Arg
    50                  55                  60
```

(2) INFORMATION FOR SEQ ID NO:22:

(i) SEQUENCE CHARACTERISTICS:
        (A) LENGTH: 2687 base pairs
        (B) TYPE: nucleic acid
        (C) STRANDEDNESS: single
        (D) TOPOLOGY: linear (ii) MOLECULE TYPE: DNA (genomic)

(viii) POSITION IN GENOME:
        (B) MAP POSITION: 7q (xi) SEQUENCE DESCRIPTION: SEQ ID NO:22:

```
CCATGGAGCG AGCTGAGAGC TCGAGTACAG AACCTGCTAA GGCCATCAAA CCTATTGATC      60

GGAAGTCAGT CCATCAGATT TGCTCTGGGC AGGTGGTACT GAGTCTAAGC ACTGCGGTAA     120

AGGAGTTAGT AGAAAACAGT CTGGATGCTG GTGCCACTAA TATTGATCTA AAGCTTAAGG     180

ACTATGGAGT GGATCTTATT GAAGTTTCAG ACAATGGATG TGGGGTAGAA GAAGAAAACT     240

TCGAAGGCTT AACTCTGAAA CATCACACAT CTAAGATTCA AGAGTTTGCC GACCTAACTC     300

AGGTTGAAAC TTTTGGCTTT CGGGGGGAAG CTCTGAGCTC ACTTTGTGCA CTGAGCGATG     360

TCACCATTTC TACCTGCCAC GCATCGGCGA AGGTTGGAAC TCGACTGATG TTTGATCACA     420

ATGGGAAAAT TATCCAGAAA ACCCCCTACC CCCGCCCCAG AGGGACCACA GTCAGCGTGC     480
```

```
AGCAGTTATT TTCCACACTA CCTGTGCGCC ATAAGGAATT TCAAAGGAAT ATTAAGAAGG      540

AGTATGCCAA AATGGTCCAG GTCTTACATG CATACTGTAT CATTTCAGCA GGCATCCGTG      600

TAAGTTGCAC CAATCAGCTT GGACAAGGAA ACGACAGCC TGTGGTATGC ACAGGTGGAA       660

GCCCCAGCAT AAAGGAAAAT ATCGGCTCTG TGTTTGGGCA GAAGCAGTTG CAAAGCCTCA      720

TTCCTTTTGT TCAGCTGCCC CCTAGTGACT CCGTGTGTGA AGAGTACGGT TTGAGCTGTT      780

CGGATGCTCT GCATAATCTT TTTTACATCT CAGGTTTCAT TTCACAATGC ACGCATGGAG      840

TTGGAAGGAG TTCAACAGAC AGACAGTTTT TCTTTATCAA CCGGCGGCCT TGTGACCCAG      900

CAAAGGTCTG CAGACTCGTG AATGAGGTCT ACCACATGTA TAATCGACAC CAGTATCCAT      960

TTGTTGTTCT TAACATTTCT GTTGATTCAG AATGCGTTGA TATCAATGTT ACTCCAGATA     1020

AAAGGCAAAT TTTGCTACAA GAGGAAAAGC TTTTGTTGGC AGTTTTAAAG ACCTCTTTGA     1080

TAGGAATGTT TGATAGTGAT GTCAACAAGC TAAATGTCAG TCAGCAGCCA CTGCTGGATG     1140

TTGAAGGTAA CTTAATAAAA ATGCATGCAG CGGATTTGGA AAAGCCCATG GTAGAAAAGC     1200

AGGATCAATC CCCTTCATTA AGGACTGGAG AAGAAAAAAA AGACGTGTCC ATTTCCAGAC     1260

TGCGAGAGGC CTTTTCTCTT CGTCACACAA CAGAGAACAA GCCTCACAGC CCAAAGACTC     1320

CAGAACCAAG AAGGAGCCCT CTAGGACAGA AAAGGGGTAT GCTGTCTTCT AGCACTTCAG     1380

GTGCCATCTC TGACAAAGGC GTCCTGAGAT CTCAGAAAGA GGCAGTGAGT TCCAGTCACG     1440

GACCCAGTGA CCCTACGGAC AGAGCGGAGG TGGAGAAGGA CTCGGGGCAC GGCAGCACTT     1500

CCGTGGATTC TGAGGGGTTC AGCATCCCAG ACACGGGCAG TCACTGCAGC AGCGAGTATG     1560

CGGCCAGCTC CCCAGGGGAC AGGGGCTCGC AGGAACATGT GGACTCTCAG GAGAAAGCGC     1620

CTGAAACTGA CGACTCTTTT TCAGATGTGG ACTGCCATTC AAACCAGGAA GATACCGGAT     1680

GTAAATTTCG AGTTTTGCCT CAGCCAACTA ATCTCGCAAC CCCAAACACA AGCGTTTTA     1740

AAAAAGAAGA AATTCTTTCC AGTTCTGACA TTTGTCAAAA GTTAGTAAAT ACTCAGGACA     1800

TGTCAGCCTC TCAGGTTGAT TGAGCTGTGA AAATTAATAA GAAAGTTGTG CCCCTGGACT     1860

TTTCTATGAG TTCTTTAGCT AAACGAATAA AGCAGTTACA TCATGAAGCA CAGCAAAGTG     1920

AAGGGGAACA GAATTACAGG AAGTTTAGGG CAAAGATTTG TCCTGGAGAA AATCAAGCAG     1980

CCGAAGATGA ACTAAGAAAA GAGATAAGTA AAACGATGTT TGCAGAAATG GAAATCATTG     2040

GTCAGTTTAA CCTGGGATTT ATAATAACCA AACTGAATGA GGATATCTTC ATAGTGGACC     2100

AGCATGCCAC GGACGAGAAG TATAACTTCG AGATGCTGCA GCAGCACACC GTGCTCCAGG     2160

GGCAGAGGCT CATAGCACCT CAGACTCTCA ACTTAACTGC TGTTAATGAA GCTGTTCTGA     2220

TAGAAAATCT GGAAATATTT AGAAAGAATG GCTTTGATTT TGTTATCGAT GAAAATGCTC     2280

CAGTCACTGA AAGGGCTAAA CTGATTTCCT TGCCAACTAG TAAAAACTGG ACCTTCGGAC     2340

CCCAGGACGT CGATGAACTG ATCTTCATGC TGAGCGACAG CCCTGGGGTC ATGTGCCGCC     2400

CTTCCCGAGT CAAGCAGATG TTTGCCTCCA GAGCCTGCCG GAAGTCGGTG ATGATTGGGA     2460

CTGCTCTCAA CACAAGCGAA TGAAGAAACT GATCACCCAC ATGGGGGAGA TGGGCCACCC     2520

CTGGAACTGT CCCCATGGAA GGCCACCATG AGACACATCG CCAACCTGGG TGTCATTTCT     2580

CAGAACTGAC CGTAGTCACT GTATGGAATA ATTGGTTTTA TCGCAGATTT TTATGTTTTG     2640

AAAGACAGAG TCTTCACTAA CCTTTTTTGT TTTAAAATGA AACCTGC                  2687
```

(2) INFORMATION FOR SEQ ID NO:23:

(i) SEQUENCE CHARACTERISTICS:
        (A) LENGTH: 862 amino acids
        (B) TYPE: amino acid (C) STRANDEDNESS: single
(D) TOPOLOGY: linear (ii) MOLECULE TYPE: protein (xi) SEQUENCE DESCRIPTION: SEQ ID NO:23:

```
Met Glu Arg Ala Glu Ser Ser Thr Glu Pro Ala Lys Ala Ile Lys
 1               5                  10                  15

Pro Ile Asp Arg Lys Ser Val His Gln Ile Cys Ser Gly Gln Val Val
            20                  25                  30

Leu Ser Leu Ser Thr Ala Val Lys Glu Leu Val Glu Asn Ser Leu Asp
        35                  40                  45

Ala Gly Ala Thr Asn Ile Asp Leu Lys Leu Lys Asp Tyr Gly Val Asp
    50                  55                  60

Leu Ile Glu Val Ser Asp Asn Gly Cys Gly Val Glu Glu Asn Phe
65                  70                  75                  80

Glu Gly Leu Thr Leu Lys His His Thr Ser Lys Ile Gln Glu Phe Ala
                85                  90                  95

Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Ala Ser
        115                 120                 125

Ala Lys Val Gly Thr Arg Leu Met Phe Asp His Asn Gly Lys Ile Ile
    130                 135                 140

Gln Lys Thr Pro Tyr Pro Arg Pro Arg Gly Thr Thr Val Ser Val Gln
145                 150                 155                 160

Gln Leu Phe Ser Thr Leu Pro Val Arg His Lys Glu Phe Gln Arg Asn
                165                 170                 175

Ile Lys Lys Glu Tyr Ala Lys Met Val Gln Val Leu His Ala Tyr Cys
            180                 185                 190

Ile Ile Ser Ala Gly Ile Arg Val Ser Cys Thr Asn Gln Leu Gly Gln
        195                 200                 205

Gly Lys Arg Gln Pro Val Val Cys Ile Gly Gly Ser Pro Ser Ile Lys
    210                 215                 220

Glu Asn Ile Gly Ser Val Phe Gly Gln Lys Gln Leu Gln Ser Leu Ile
225                 230                 235                 240

Pro Phe Val Gln Leu Pro Pro Ser Asp Ser Val Cys Glu Glu Tyr Gly
                245                 250                 255

Leu Ser Cys Ser Asp Ala Leu His Asn Leu Phe Tyr Ile Ser Gly Phe
            260                 265                 270

Ile Ser Gln Cys Thr His Gly Val Gly Arg Ser Ser Thr Asp Arg Gln
        275                 280                 285

Phe Phe Phe Ile Asn Arg Arg Pro Cys Asp Pro Ala Lys Val Cys Arg
    290                 295                 300

Leu Val Asn Glu Val Tyr His Met Tyr Asn Arg His Gln Tyr Pro Phe
305                 310                 315                 320

Val Val Leu Asn Ile Ser Val Asp Ser Glu Cys Val Asp Ile Asn Val
                325                 330                 335

Thr Pro Asp Lys Arg Gln Ile Leu Leu Gln Glu Glu Lys Leu Leu Leu
            340                 345                 350

Ala Val Leu Lys Thr Ser Leu Ile Gly Met Phe Asp Ser Asp Val Asn
        355                 360                 365

Lys Leu Asn Val Ser Gln Gln Pro Leu Leu Asp Val Glu Gly Asn Leu
    370                 375                 380

Ile Lys Met His Ala Ala Asp Leu Glu Lys Pro Met Val Glu His Gln
```

```
                385                 390                 395                 400
Asp Gln Ser Pro Ser Leu Arg Ile Gly Glu Glu Lys Lys Asp Val Ser
                    405                 410                 415
Ile Ser Arg Leu Arg Glu Ala Phe Ser Leu Arg His Thr Thr Glu Asn
                    420                 425                 430
Lys Pro His Ser Pro Lys Thr Pro Glu Pro Arg Arg Ser Pro Leu Gly
                    435                 440                 445
Gln Lys Arg Gly Met Leu Ser Ser Thr Ser Gly Ala Ile Ser Asp
            450                 455                 460
Lys Gly Val Leu Arg Ser Gln Lys Glu Ala Val Ser Ser Ser His Gly
465                 470                 475                 480
Pro Ser Asp Pro Thr Asp Arg Ala Glu Val Glu Lys Asp Ser Gly His
                    485                 490                 495
Gly Ser Thr Ser Val Asp Ser Glu Gly Phe Ser Ile Pro Asp Thr Gly
                    500                 505                 510
Ser His Cys Ser Ser Glu Tyr Ala Ala Ser Ser Pro Gly Asp Arg Gly
            515                 520                 525
Ser Gln Glu His Val Asp Ser Gln Glu Lys Ala Pro Glu Thr Asp Asp
        530                 535                 540
Ser Phe Ser Asp Val Asp Cys His Ser Asn Gln Glu Asp Thr Gly Cys
545                 550                 555                 560
Lys Phe Arg Val Leu Pro Gln Pro Ile Asn Leu Ala Thr Pro Asn Thr
                    565                 570                 575
Lys Arg Phe Lys Lys Glu Glu Ile Leu Ser Ser Asp Ile Cys Gln
                    580                 585                 590
Lys Leu Val Asn Thr Gln Asp Met Ser Ala Ser Gln Val Asp Val Ala
            595                 600                 605
Val Lys Ile Asn Lys Lys Val Val Pro Leu Asp Phe Ser Met Ser Ser
        610                 615                 620
Leu Ala Lys Arg Ile Lys Gln Leu His His Glu Ala Gln Ser Glu
625                 630                 635                 640
Gly Glu Gln Asn Tyr Arg Lys Phe Arg Ala Lys Ile Cys Pro Gly Glu
                    645                 650                 655
Asn Gln Ala Ala Glu Asp Glu Leu Arg Lys Glu Ile Ser Lys Thr Met
                    660                 665                 670
Phe Ala Glu Met Glu Ile Ile Gly Gln Phe Asn Leu Gly Phe Ile Ile
                    675                 680                 685
Thr Lys Leu Asn Glu Asp Ile Phe Ile Val Asp Gln His Ala Thr Asp
            690                 695                 700
Glu Lys Tyr Asn Phe Glu Met Leu Gln Gln His Thr Val Leu Gln Gly
705                 710                 715                 720
Gln Arg Leu Ile Ala Pro Gln Thr Leu Asn Leu Thr Ala Val Asn Glu
                    725                 730                 735
Ala Val Leu Ile Glu Asn Leu Glu Ile Phe Arg Lys Asn Gly Phe Asp
                    740                 745                 750
Phe Val Ile Asp Glu Asn Ala Pro Val Thr Glu Arg Ala Lys Leu Ile
                    755                 760                 765
Ser Leu Pro Thr Ser Lys Asn Trp Thr Phe Gly Pro Gln Asp Val Asp
        770                 775                 780
Glu Leu Ile Phe Met Leu Ser Asp Ser Pro Gly Val Met Cys Arg Pro
785                 790                 795                 800
Ser Arg Val Lys Gln Met Phe Ala Ser Arg Ala Cys Arg Lys Ser Val
                    805                 810                 815
```

```
        Met Ile Gly Thr Ala Leu Asn Thr Ser Glu Met Lys Lys Leu Ile Thr
                    820                 825                 830

His Met Gly Glu Met Gly His Pro Trp Asn Cys Pro His Gly Arg Pro
                    835                 840                 845

Thr Met Arg His Ile Ala Asn Leu Gly Val Ile Ser Gln Asn
        850                 855                 860

(2) INFORMATION FOR SEQ ID NO:24:

(i) SEQUENCE CHARACTERISTICS:
        (A) LENGTH: 903 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:24:

Met Phe His His Ile Glu Asn Leu Leu Ile Glu Thr Glu Lys Arg Cys
        1               5                   10                  15

Lys Gln Lys Glu Gln Arg Tyr Ile Pro Val Lys Tyr Leu Phe Ser Met
                    20                  25                  30

Thr Gln Ile His Gln Ile Asn Asp Ile Asp Val His Arg Ile Thr Ser
                    35                  40                  45

Gly Gln Val Ile Thr Asp Leu Thr Ala Val Lys Glu Leu Val Asp
                50                  55                  60

Asn Ser Ile Asp Ala Asn Ala Asn Gln Ile Glu Ile Phe Lys Asp
        65                  70                  75                  80

Tyr Gly Leu Glu Ser Ile Glu Cys Ser Asp Asn Gly Asp Gly Ile Asp
                    85                  90                  95

Pro Ser Asn Tyr Glu Phe Leu Ala Leu Lys His Tyr Thr Ser Lys Ile
                    100                 105                 110

Ala Lys Phe Gln Asp Val Ala Lys Val Gln Thr Leu Gly Phe Arg Gly
                    115                 120                 125

Glu Ala Leu Ser Ser Leu Cys Gly Ile Ala Lys Leu Ser Val Ile Thr
                    130                 135                 140

Thr Thr Ser Pro Pro Lys Ala Asp Lys Leu Glu Tyr Asp Met Val Gly
        145                 150                 155                 160

His Ile Thr Ser Lys Thr Thr Ser Arg Asn Lys Gly Thr Thr Val Leu
                    165                 170                 175

Val Ser Gln Leu Phe His Asn Leu Pro Val Arg Gln Lys Glu Phe Ser
                    180                 185                 190

Lys Thr Phe Lys Arg Gln Phe Thr Lys Cys Leu Thr Val Ile Gln Gly
                    195                 200                 205

Tyr Ala Ile Ile Asn Ala Ala Ile Lys Phe Ser Val Trp Asn Ile Thr
                    210                 215                 220

Pro Lys Gly Lys Lys Asn Leu Ile Leu Ser Thr Met Arg Asn Ser Ser
        225                 230                 235                 240

Met Arg Lys Asn Ile Ser Ser Val Phe Gly Ala Gly Met Phe Gly
                    245                 250                 255

Leu Glu Glu Val Asp Leu Val Leu Asp Leu Asn Pro Phe Lys Asn Arg
                    260                 265                 270

Met Leu Gly Lys Tyr Thr Asp Asp Pro Asp Phe Leu Asp Leu Asp Tyr
                    275                 280                 285

Lys Ile Arg Val Lys Gly Tyr Ile Ser Gln Asn Ser Phe Gly Cys Gly
                    290                 295                 300

Arg Asn Ser Lys Asp Arg Gln Phe Ile Tyr Val Asn Lys Arg Pro Val
```

```
305                 310                 315                 320
Glu Tyr Ser Thr Leu Leu Lys Cys Cys Asn Glu Val Tyr Lys Thr Phe
                325                 330                 335
Asn Asn Val Gln Phe Pro Ala Val Phe Leu Asn Leu Glu Leu Pro Met
            340                 345                 350
Ser Leu Ile Asp Val Asn Val Thr Pro Asp Lys Arg Val Ile Leu Leu
            355                 360                 365
His Asn Glu Arg Ala Val Ile Asp Ile Phe Lys Thr Thr Leu Ser Asp
        370                 375                 380
Tyr Tyr Asn Arg Gln Glu Leu Ala Leu Pro Lys Arg Met Cys Ser Gln
385                 390                 395                 400
Ser Glu Gln Gln Ala Gln Lys Arg Leu Lys Thr Glu Val Phe Asp Asp
                405                 410                 415
Arg Ser Thr Thr His Glu Ser Asp Asn Glu Asn Tyr His Thr Ala Arg
            420                 425                 430
Ser Glu Ser Asn Gln Ser Asn His Ala His Phe Asn Ser Thr Thr Gly
            435                 440                 445
Val Ile Asp Lys Ser Asn Gly Thr Glu Leu Thr Ser Val Met Asp Gly
        450                 455                 460
Asn Tyr Thr Asn Val Thr Asp Val Ile Gly Ser Glu Cys Glu Val Ser
465                 470                 475                 480
Val Asp Ser Ser Val Val Leu Asp Glu Gly Asn Ser Ser Thr Pro Thr
                485                 490                 495
Lys Lys Leu Pro Ser Ile Lys Thr Asp Ser Gln Asn Leu Ser Asp Leu
            500                 505                 510
Asn Leu Asn Asn Phe Ser Asn Pro Glu Phe Gln Asn Ile Thr Ser Pro
            515                 520                 525
Asp Lys Ala Arg Ser Leu Glu Lys Val Val Glu Glu Pro Val Tyr Phe
        530                 535                 540
Asp Ile Asp Gly Glu Lys Phe Gln Glu Lys Ala Val Leu Ser Gln Ala
545                 550                 555                 560
Asp Gly Leu Val Phe Val Asp Asn Glu Cys His Glu His Thr Asn Asp
                565                 570                 575
Cys Cys His Gln Glu Arg Arg Gly Ser Thr Asp Ile Glu Gln Asp Asp
            580                 585                 590
Glu Ala Asp Ser Ile Tyr Ala Glu Ile Glu Pro Val Glu Ile Asn Val
        595                 600                 605
Arg Thr Pro Leu Lys Asn Ser Arg Lys Ser Ile Ser Lys Asp Asn Tyr
        610                 615                 620
Arg Ser Leu Ser Asp Gly Leu Thr His Arg Lys Phe Glu Asp Glu Ile
625                 630                 635                 640
Leu Glu Tyr Asn Leu Ser Thr Lys Asn Phe Lys Glu Ile Ser Lys Asn
                645                 650                 655
Gly Lys Gln Met Ser Ser Ile Ser Lys Arg Lys Ser Glu Ala Gln
            660                 665                 670
Glu Asn Ile Ile Lys Asn Lys Asp Glu Leu Glu Asp Phe Glu Gln Gly
        675                 680                 685
Glu Lys Tyr Leu Thr Leu Thr Val Ser Lys Asn Asp Phe Lys Lys Met
        690                 695                 700
Glu Val Val Gly Gln Phe Asn Leu Gly Phe Ile Ile Val Thr Arg Lys
705                 710                 715                 720
Val Asp Asn Lys Ser Lys Leu Phe Ile Val Asp Gln His Ala Ser Asp
                725                 730                 735
```

```
            Glu Lys Tyr Asn Phe Glu Thr Leu Gln Ala Val Thr Val Phe Lys Ser
                        740                 745                 750

Gln Lys Leu Ile Ile Pro Gln Pro Val Glu Leu Ser Val Ile Asp Glu
                        755                 760                 765

Leu Val Val Leu Asp Asn Leu Pro Val Phe Glu Lys Asn Gly Phe Lys
            770                 775                 780

Leu Lys Ile Asp Glu Glu Glu Phe Gly Ser Arg Val Lys Leu Leu
            785                 790                 795                 800

Ser Leu Pro Thr Ser Lys Gln Thr Leu Phe Asp Leu Gly Asp Phe Asn
                        805                 810                 815

Glu Leu Ile His Leu Ile Lys Glu Asp Gly Gly Leu Arg Arg Asp Asn
                        820                 825                 830

Ile Arg Cys Ser Lys Ile Arg Ser Met Phe Ala Met Arg Ala Cys Arg
                        835                 840                 845

Ser Ser Ile Met Ile Gly Lys Pro Leu Asn Lys Lys Thr Met Thr Arg
                        850                 855                 860

Val Val His Asn Leu Ser Glu Leu Asp Lys Pro Trp Asn Cys Pro His
            865                 870                 875                 880

Gly Arg Pro Thr Met Arg His Leu Met Glu Ile Arg Asp Trp Ser Ser
                        885                 890                 895

Phe Ser Lys Asp Tyr Glu Ile
                        900

(2) INFORMATION FOR SEQ ID NO:25:

(i) SEQUENCE CHARACTERISTICS:
        (A) LENGTH: 2577 base pairs
        (B) TYPE: nucleic acid
        (C) STRANDEDNESS: single
        (D) TOPOLOGY: linear (ii) MOLECULE TYPE: cDNA (viii) POSITION IN GENOME:
        (B) MAP POSITION: Chromosome 9 Band E (xi) SEQUENCE DESCRIPTION: SEQ ID NO:25:

TTCCGGCCAA TGCTATCAAA GAGATGATAG AAAACTGTTT AGATGCAAAA TCTACAAATA      60

TTCAAGTGGT TGTTAAGGAA GGTGGCCTGA AGCTAATTCA GATCCAAGAC AATGGCACTG     120

GAATCAGGAA GGAAGATCTG GATATTGTGT GTGAGAGGTT CACTACGAGT AAACTGCAGA     180

CTTTTGAGGA TTTAGCCAGT ATTTCTACCT ATGGCTTTCG TGGTGAGCAT TTGGCAAGCA     240

TAAGTCATGT GGCCCATGTC ACTATTACAA CCAAAACAGC TGATGGGAAA TGTGCGTACA     300

GAGCAAGTTA CTCAGATGGA AAGCTGCAAG CCCCTCCTAA ACCCTGTGCA GGCAACCAGG     360

GCACCCTGAT CACGGTGGAA GACCTTTTTT ACAACATAAT CACAAGGAGG AAAGCTTTAA     420

AAAATCCAAG TGAAGAGTAC GGAAAAATTT TGGAAGTTGT TGGCAGGTAT TCAATACACA     480

ATTCAGGCAT TAGTATCTCA GTTAAAAAAC AAGGTGAGAC AGTATCTGAT GTCAGAACAC     540

TGCCCAATGC CACAACCGTG GACAACATTC GCTCCATCTT TGGAAATGCG GTTAGTCGAG     600

AACTGATAGA AGTTGGGTGT GAGGATAAAA CCCTAGCTTT CAAAATGAAT GGCTATATAT     660

CGAATGCAAA GTATTCAGTG AAGAAGTGCA TTTTCCTACT CTTCATCAAC CACCGTCTGG     720

TAGAATCAGC TGCCTTGAGA AAAGCCATTG AAACTGTATA TGCAGCATAC TTGCCAAAAA     780

CACACACCCA TTCCTGTACC TCAGTTTGAA ATCAGCCCTC AGAACGTGAC GTCAATGTAC     840

ACCCCACCAA GACAGAAGTT CATTTTCTGC ACGAGGAGAG CATTCTGCAG CGTGTGCAGC     900

AGCACATTGA GAGCAAGCTG CTGGGCTCCA ATTCCTCCAG GATGTATTTC ACCCAGACCT     960
```

```
TGCTTCCAGG ACTTGCTGGG CCTCTGGGGA GGCAGCTAGA CCCACGACAG GGGTGGCTTC      1020

CTCATCCACT AGTGGAAGTG GCGACAAGGT CTACGCTTAC CAGATGTCGC GTACGGACTC      1080

CCGGGATCAG AAGCTTGACG CCTTTCTGCA GCCTGTAAGC AGCCTTGTGC CCAGCCAGCC      1140

CCAGGACCCT CGCCCTGTCC GAGGGGCCAG GACAGAGGGC TCTCCTGAAA GGGCCACGCG      1200

GGAGGATGAG GAGATGCTTG CTCTCCCAGC CCCCGCTGAA GCAGCTGCTG AGAGTGAGAA      1260

CTTGGAGAGG GAATCACTAA TGGAGACTTC AGACGCAGCC CAGAAAGCGG CACCCACTTC      1320

CAGTCCAGGA AGCTCCAGAA AGAGTCATCG GGAGGACTCT GATGTGGAAA TGGTGGAAAA      1380

TGCTTCCGGG AAGGAAATGA CAGCTGCTTG CTACCCCAGG AGGAGGATCA TTAACCTCAC      1440

CAGCGTCTTG AGTCTCCAGG AAGAGATTAG TGAGCGGTGC CATGAGACTC TCCGGGAGAT      1500

ACTCCGTAAC CATTCCTTTG TGGGCTGTGT GAATCCTCAG TGGGCCTTGG CACAGCACCA      1560

GACCAAGCTA TACCTCCTCA ACACTACCAA GCTCAGTGAA GAGCTGTTCT ACCAGATACT      1620

CATTTATGAT TTTGCCAACT TGGTGTTCT GAGGTTATCG GAACCAGCGC CACTCTTCGA       1680

CCTGGCCATG CTGGCTTAGA CAGTCCTGAA AGTGGCTGGA CAGAGGACGA CGGCCCGAAG      1740

AAGGGCTTGC AGAGTACATT GTCGAGTTTC TGAAGAGAAG CGAGATGCTT GCAGACTATT      1800

CTCTGTGAGA TCGATGAGAA GGGAACCTGA TTGATTACTC TTCTGATGAC AGCTATGTGC      1860

CACCTTTGGA GGGACTGCCT ATCTTCATTC TTCGACTGGC CACTGAGGTG AATTGGGTGA      1920

AGAAAAGGAG TGTTTTGAAA GTCTCAGTAA AGAATGTGCT ATGTTTTACT CCATTCGGAA      1980

GCAGTATATA CTGGAGGAGT CGACCCTCTC AGGCCAGCAG AGTGACATGC CTGGCTCCAC      2040

GTCAAAGCCC TGGAAGTGGA CTGTGGAGCA CATTATCTAT AAAGCCTTCC GCTCACACCT      2100

CCTACCTCCG AAGCATTTCA CAGAAGATGG CAATGTCCTG CAGCTTGCCA ACCTGCCAGA      2160

TCTATACAAA GTCTTTGAGC GGTGTTAAAT ACAATCATAG CCACCGTAGA GACTGCATGA      2220

CCATCCAAGG CGAAGTGTAT GGTACTAATC TGGAAGCCAC AGAATAGGAC ACTTGGTTTC      2280

AGCTCCAGGG TTTTCAGTGC TCACTATTCT TGTTCTGTAT CCCAGTATTG GTGCTGCAAC      2340

TTAATGTACT TCACCTGTGG ATTGGCTGCA AATAAACTCA CGTGTATTGG AAAAAAGGAA      2400

TTCCTGCAGC CCGGGGGATC CACTAGTTCT AGAGCGGCCG CCACCGGTGG AGCTCCAGCT      2460

TTTGTTCCCT TTAGTGAGGG TTAATTTCGA GCTTGGCGTA ATCATGGTCA TAGCTGTTTC      2520

CTGTGTGAAA TTGTTATCCG CTCACAATTC CACACAACAT ACGAGCCGGA AGCATAA        2577

(2) INFORMATION FOR SEQ ID NO:26:

(i) SEQUENCE CHARACTERISTICS:
        (A) LENGTH: 728 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:26:

Pro Ala Asn Ala Ile Lys Glu Met Ile Glu Asn Cys Leu Asp Ala Lys
    1               5                  10                  15

Ser Thr Asn Ile Gln Val Val Lys Glu Gly Gly Leu Lys Leu Ile
                20                  25                  30

Gln Ile Gln Asp Asn Gly Thr Gly Ile Arg Lys Glu Asp Leu Asp Ile
                    35                  40                  45

Val Cys Glu Arg Phe Thr Thr Ser Lys Leu Gln Thr Phe Glu Asp Leu
                        50                  55                  60
```

-continued

```
Ala Ser Ile Ser Thr Tyr Gly Phe Arg Gly Glu His Leu Ala Ser Ile
 65                  70                  75                  80

Ser His Val Ala His Val Thr Ile Thr Thr Lys Thr Ala Asp Gly Lys
                 85                  90                  95

Cys Ala Tyr Arg Ala Ser Tyr Ser Asp Gly Lys Leu Gln Ala Pro Pro
            100                 105                 110

Lys Pro Cys Ala Gly Asn Gln Gly Thr Leu Ile Thr Val Glu Asp Leu
        115                 120                 125

Phe Tyr Asn Ile Ile Thr Arg Arg Lys Ala Leu Lys Asn Pro Ser Glu
    130                 135                 140

Glu Tyr Gly Lys Ile Leu Glu Val Val Gly Arg Tyr Ser Ile His Asn
145                 150                 155                 160

Ser Gly Ile Ser Ile Ser Val Lys Lys Gln Gly Glu Thr Val Ser Asp
                165                 170                 175

Val Arg Thr Leu Pro Asn Ala Thr Thr Val Asp Asn Ile Arg Ser Ile
            180                 185                 190

Phe Gly Asn Ala Val Ser Arg Glu Leu Ile Glu Val Gly Cys Glu Asp
        195                 200                 205

Lys Thr Leu Ala Phe Lys Met Asn Gly Tyr Ile Ser Asn Ala Lys Tyr
    210                 215                 220

Ser Val Lys Lys Cys Ile Phe Leu Leu Phe Ile Asn His Arg Leu Val
225                 230                 235                 240

Glu Ser Ala Ala Leu Arg Lys Ala Ile Glu Thr Val Tyr Ala Ala Tyr
                245                 250                 255

Leu Pro Lys Thr His Thr His Ser Cys Thr Ser Val Glx Asn Gln Pro
            260                 265                 270

Ser Glu Arg Asp Val Asn Val His Pro Thr Lys Thr Glu Val His Phe
        275                 280                 285

Leu His Glu Glu Ser Ile Leu Gln Arg Val Gln Gln His Ile Glu Ser
    290                 295                 300

Lys Leu Leu Gly Ser Asn Ser Ser Arg Met Val Phe His Pro Lys Leu
305                 310                 315                 320

Ala Ser Arg Thr Cys Trp Ala Ser Gly Glu Ala Ala Arg Pro Thr Thr
                325                 330                 335

Gly Val Ala Ser Ser Ser Thr Ser Gly Ser Gly Asp Lys Val Tyr Ala
            340                 345                 350

Tyr Gln Met Ser Arg Thr Asp Ser Arg Asp Gln Lys Leu Asp Ala Phe
        355                 360                 365

Leu Gln Pro Val Ser Ser Leu Val Pro Ser Gln Pro Gln Asp Pro Arg
    370                 375                 380

Pro Val Arg Gly Ala Arg Thr Glu Gly Ser Pro Glu Arg Ala Thr Arg
385                 390                 395                 400

Glu Asp Glu Glu Met Leu Ala Leu Pro Ala Pro Ala Glu Ala Ala Ala
                405                 410                 415

Glu Ser Glu Asn Leu Glu Arg Glu Ser Leu Met Glu Thr Ser Asp Ala
            420                 425                 430

Ala Gln Lys Ala Ala Pro Thr Ser Ser Pro Gly Ser Ser Arg Lys Ser
        435                 440                 445

His Arg Glu Asp Ser Asp Val Glu Met Val Glu Asn Ala Ser Gly Lys
    450                 455                 460

Glu Met Thr Ala Ala Cys Tyr Pro Arg Arg Ile Ile Asn Leu Thr
465                 470                 475                 480

Ser Val Leu Ser Leu Gln Glu Glu Ile Ser Glu Arg Cys His Glu Thr
                485                 490                 495
```

```
Leu Arg Glu Ile Leu Arg Asn His Ser Phe Val Gly Cys Val Asn Pro
            500                 505                 510

Gln Trp Ala Leu Ala Gln His Gln Thr Lys Leu Tyr Leu Leu Asn Thr
            515                 520                 525

Thr Lys Leu Ser Glu Glu Leu Phe Tyr Gln Ile Leu Ile Tyr Asp Phe
            530                 535                 540

Ala Asn Phe Gly Val Leu Arg Leu Ser Glu Pro Ala Pro Leu Phe Asp
545                 550                 555                 560

Leu Ala Met Leu Ala Glx Thr Val Leu Lys Val Ala Gly Gln Arg Thr
                565                 570                 575

Thr Ala Arg Arg Arg Ala Cys Arg Val His Cys Arg Val Ser Glu Glu
            580                 585                 590

Lys Arg Asp Ala Cys Arg Leu Phe Ser Val Arg Ser Met Arg Arg Glu
            595                 600                 605

Pro Asp Glx Leu Leu Phe Glx Glx Gln Leu Cys Ala Thr Phe Gly Gly
            610                 615                 620

Thr Ala Tyr Leu His Ser Ser Thr Gly His Glx Gly Glu Leu Gly Glu
625                 630                 635                 640

Glu Lys Glu Cys Phe Glu Ser Leu Ser Lys Glu Cys Ala Met Phe Tyr
            645                 650                 655

Ser Ile Arg Lys Gln Tyr Ile Leu Glu Glu Ser Thr Leu Ser Gly Gln
            660                 665                 670

Gln Ser Asp Met Pro Gly Ser Thr Ser Lys Pro Trp Lys Trp Thr Val
            675                 680                 685

Glu His Ile Ile Tyr Lys Ala Phe Arg Ser His Leu Leu Pro Pro Lys
            690                 695                 700

His Phe Thr Glu Asp Gly Asn Val Leu Gln Leu Ala Asn Leu Pro Asp
705                 710                 715                 720

Leu Tyr Lys Val Phe Glu Arg Cys
            725

(2) INFORMATION FOR SEQ ID NO:27:

(i) SEQUENCE CHARACTERISTICS:
        (A) LENGTH: 756 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:27:

Met Ser Phe Val Ala Gly Val Ile Arg Arg Leu Asp Glu Thr Val Val
1               5                  10                  15

Asn Arg Ile Ala Ala Gly Glu Val Ile Gln Arg Pro Ala Asn Ala Ile
            20                  25                  30

Lys Glu Met Ile Glu Asn Cys Leu Asp Ala Lys Ser Thr Ser Ile Gln
            35                  40                  45

Val Ile Val Lys Glu Gly Gly Leu Lys Leu Ile Gln Ile Gln Asp Asn
        50                  55                  60

Gly Thr Gly Ile Arg Lys Glu Asp Leu Asp Ile Val Cys Glu Arg Phe
65                  70                  75                  80

Thr Thr Ser Lys Leu Gln Ser Phe Glu Asp Leu Ala Ser Ile Ser Thr
                85                  90                  95

Tyr Gly Phe Arg Gly Glu Ala Leu Ala Ser Ile Ser His Val Ala His
            100                 105                 110
```

```
Val Thr Ile Thr Thr Lys Thr Ala Asp Gly Lys Cys Ala Tyr Arg Ala
            115                 120                 125

Ser Tyr Ser Asp Gly Lys Leu Lys Ala Pro Lys Pro Cys Ala Gly
130                 135                 140

Asn Gln Gly Thr Gln Ile Thr Val Glu Asp Leu Phe Tyr Asn Ile Ala
145                 150                 155                 160

Thr Arg Arg Lys Ala Leu Lys Asn Pro Ser Glu Glu Tyr Gly Lys Ile
                165                 170                 175

Leu Glu Val Val Gly Arg Tyr Ser Val His Asn Ala Gly Ile Ser Phe
                180                 185                 190

Ser Val Lys Lys Gln Gly Glu Thr Val Ala Asp Val Arg Thr Leu Pro
            195                 200                 205

Asn Ala Ser Thr Val Asp Asn Ile Arg Ser Ile Phe Gly Asn Ala Val
210                 215                 220

Ser Arg Glu Leu Ile Glu Ile Gly Cys Glu Asp Lys Thr Leu Ala Phe
225                 230                 235                 240

Lys Met Asn Gly Tyr Ile Ser Asn Ala Asn Tyr Ser Val Lys Lys Cys
                245                 250                 255

Ile Phe Leu Leu Phe Ile Asn His Arg Leu Val Glu Ser Thr Ser Leu
            260                 265                 270

Arg Lys Ala Ile Glu Thr Val Tyr Ala Ala Tyr Leu Pro Lys Asn Thr
            275                 280                 285

His Pro Phe Leu Tyr Leu Ser Leu Glu Ile Ser Pro Gln Asn Val Asp
290                 295                 300

Val Asn Val His Pro Thr Lys His Glu Val His Phe Leu His Glu Glu
305                 310                 315                 320

Ser Ile Leu Glu Arg Val Gln Gln His Ile Glu Ser Lys Leu Leu Gly
                325                 330                 335

Ser Asn Ser Ser Arg Met Tyr Phe Thr Gln Thr Leu Leu Pro Gly Leu
            340                 345                 350

Ala Gly Pro Ser Gly Glu Met Val Lys Ser Thr Thr Ser Leu Thr Ser
            355                 360                 365

Ser Ser Thr Ser Gly Ser Ser Asp Lys Val Tyr Ala His Gln Met Val
            370                 375                 380

Arg Thr Asp Ser Arg Glu Gln Lys Leu Asp Ala Phe Leu Gln Pro Leu
385                 390                 395                 400

Ser Lys Pro Leu Ser Ser Gln Pro Gln Ala Ile Val Thr Glu Asp Lys
                405                 410                 415

Thr Asp Ile Ser Ser Gly Arg Ala Arg Gln Gln Asp Glu Glu Met Leu
                420                 425                 430

Glu Leu Pro Ala Pro Ala Glu Val Ala Ala Lys Asn Gln Ser Leu Glu
            435                 440                 445

Gly Asp Thr Thr Lys Gly Thr Ser Glu Met Ser Glu Lys Arg Gly Pro
450                 455                 460

Thr Ser Ser Asn Pro Arg Lys Arg His Arg Glu Asp Ser Asp Val Glu
465                 470                 475                 480

Met Val Glu Asp Asp Ser Arg Lys Glu Met Thr Ala Ala Cys Thr Pro
                485                 490                 495

Arg Arg Arg Ile Ile Asn Leu Thr Ser Val Leu Ser Leu Gln Glu Glu
                500                 505                 510

Ile Asn Glu Gln Gly His Glu Val Leu Arg Glu Met Leu His Asn His
            515                 520                 525

Ser Phe Val Gly Cys Val Asn Pro Gln Trp Ala Leu Ala Gln His Gln
530                 535                 540
```

```
      Thr Lys Leu Tyr Leu Leu Asn Thr Thr Lys Leu Ser Glu Glu Leu Phe
      545                 550                 555                 560

Tyr Gln Ile Leu Ile Tyr Asp Phe Ala Asn Phe Gly Val Leu Arg Leu
                      565                 570                 575

Ser Glu Pro Ala Pro Leu Phe Asp Leu Ala Met Leu Ala Leu Asp Ser
                  580                 585                 590

Pro Glu Ser Gly Trp Thr Glu Asp Gly Pro Lys Gly Leu Ala
              595                 600                 605

Glu Tyr Ile Val Glu Phe Leu Lys Lys Ala Glu Met Leu Ala Asp
          610                 615                 620

Tyr Phe Ser Leu Glu Ile Asp Glu Glu Gly Asn Leu Ile Gly Leu Pro
      625                 630                 635                 640

Leu Leu Ile Asp Asn Tyr Val Pro Pro Leu Glu Gly Leu Pro Ile Phe
                      645                 650                 655

Ile Leu Arg Leu Ala Thr Glu Val Asn Trp Asp Glu Glu Lys Glu Cys
                  660                 665                 670

Phe Glu Ser Leu Ser Lys Glu Cys Ala Met Phe Tyr Ser Ile Arg Lys
                  675                 680                 685

Gln Tyr Ile Ser Glu Glu Ser Thr Leu Ser Gly Gln Gln Ser Glu Val
          690                 695                 700

Pro Gly Ser Ile Pro Asn Ser Trp Lys Trp Thr Val Glu His Ile Val
      705                 710                 715                 720

Tyr Lys Ala Leu Arg Ser His Ile Leu Pro Pro Lys His Phe Thr Glu
                      725                 730                 735

Asp Gly Asn Ile Leu Gln Leu Ala Asn Leu Pro Asp Leu Tyr Lys Val
                  740                 745                 750

Phe Glu Arg Cys
              755

(2) INFORMATION FOR SEQ ID NO:28:

(i) SEQUENCE CHARACTERISTICS:
        (A) LENGTH: 3065 base pairs
        (B) TYPE: nucleic acid
        (C) STRANDEDNESS: single
        (D) TOPOLOGY: linear (ii) MOLECULE TYPE: cDNA (viii) POSITION IN GENOME:
        (B) MAP POSITION: Chromosome 5 Band G (xi) SEQUENCE DESCRIPTION: SEQ ID NO:28:

CGGTGAAGGT CCTGAAGAAT TTCCAGATTC CTGAGTATCA TTGGAGGAGA CAGATAACCT    60

GTCGTCAGGT AACGATGGTG TATATGCAAC AGAAATGGGT GTTCCTGGAG ACGCGTCTTT   120

TCCCGAGAGC GGCACCGCAA CTCTCCCGCG GTGACTGTGA CTGGAGGAGT CCTGCATCCA   180

TGGAGCAAAC CGAAGGCGTG AGTACAGAAT GTGCTAAGGC CATCAAGCCT ATTGATGGGA   240

AGTCAGTCCA TCAAATTTGT TCTGGGCAGG TGATACTCAG TTTAAGCACC GCTGTGAAGG   300

AGTTGATAGA AAATAGTGTA GATGCTGGTG CTACTACTAT TGATCTAAGG CTTAAAGACT   360

ATGGGGTGGA CCTCATTGAA GTTTCAGACA ATGGATGTGG GGTAGAAGAA GAAAACTTTG   420

AAGGTCTAGC TCTGAAACAT CACACATCTA AGATTCAAGA GTTTGCCGAC CTCACGCAGG   480

TTGAAACTTT CGGCTTTCGG GGGGAAGCTC TGAGCTCTCT GTGTGCACTA AGTGATGTCA   540

CTATATCTAC CTGCCACGGG TCTGCAAGCG TTGGGACTCG ACTGGTGTTT GACCATAATG   600

GGAAAATCAC CCAGAAAACT CCCTACCCCC GACCTAAAGG AACCACAGTC AGTGTGCAGC   660
```

```
ACTTATTTTA TACACTACCC GTGCGTTACA AAGAGTTTCA GAGGAACATT AAAAAGGAGT      720

ATTCCAAAAT GGTGCAGGTC TTACAGGCGT ACTGTATCAT CTCAGCAGGC GTCCGTGTAA      780

GCTGCACTAA TCAGCTCGGA CAGGGGAAGC GGCACGCTGT GGTGTGCACA AGCGGCACGT      840

CTGGCATGAA GGAAAATATC GGGTCTGTGT TTGGCCAGAA GCAGTTGCAA AGCCTCATTC      900

CTTTTGTTCA GCTGCCCCCT AGTGACGCTG TGTGTGAAGA GTACGGCCTG AGCACTTCAG      960

GACGCCACAA AACCTTTTCT ACGTTTTCGG GCTTCATTTC ACAGTGCACG CACGGCGCCG     1020

GGAGGAGTGC AACAGACAGG CAGTTTTTCT TCATCAATCA GAGGCCCTGT GACCCAGCAA     1080

AGGTCTCTAA GCTTGTCAAT GAGGTTTATC ACATGTATAA CCGGCATCAG TACCCATTTG     1140

TCGTCCTTAA CGTTTCCGTT GACTCAGAAT GTGTGGATAT TAATGTAACT CCAGATAAAA     1200

GGCAAATTCT ACTACAAGAA GAGAAGCTAT TGCTGGCCGT TTTAAAGACC TCCTTGATAG     1260

GAATGTTTGA CAGTGATGCA AACAAGCTTA ATGTCAACCA GCAGCCACTG CTAGATGTTG     1320

AAGGTAACTT AGTAAAGTCG CATACTGCAG AACTAGAAAA GCCTGTGCCA GGAAAGCAAG     1380

ATAACTCTCC TTCACTGAAG AGCACAGCAG ACGAGAAAAA GGTAGCATCC ATCTCCAGGC     1440

TGAGAGAGGC CTTTTCTCTT CATCCTACTA AAGAGATCAA GTCTAGGGGT CCAGAGACTG     1500

CTGAACTGAC ACGGAGTTTT CCAAGTGAGA AAAGGGGCGT GTTATCCTCT TATCCTTCAG     1560

ACGTCATCTC TTACAGAGGC CTCCGTGGCT CGCAGGACAA ATTGGTGAGT CCCACGGACA     1620

GCCCTGGTGA CTGTATGGAC AGAGAGAAAA TAGAAAAAGA CTCAGGGCTC AGCAGCACCT     1680

CAGCTGGCTC TGAGGAAGAG TTCAGCACCC AGAAGTGGC CAGTAGCTTT AGCAGTGACT     1740

ATAACGTGAG CTCCCTAGAA GACAGACCTT CTCAGGAAAC CATAAACTGT GGTGACCTGC     1800

TGCCGTCCTC CAGGTACAGG ACAGTCCTTG AAGCCAGAAG ACCATGGATA TCAATGCAAA     1860

GCTCTACCTC TAGCTCGTCT GTCACCCACA AATGCCAAGC GCTTCAAGAC AGAGGAAGAC     1920

CCTCAAATGT CAACATATCT CAAAGATTGC CTGGTCCTCA GAGCACCTCA GCAGCTGAGG     1980

TCGATGTAGC CATAAAAATG AATAAGAGAT CGTGCTCCTC GAGTTCTCTA GCTAAGCGAA     2040

TGAAGCAGTT ACAGCACCTA AAGGCGCAGA ACAAACATGA ACTGAGTTAC AGAAAATTTA     2100

GGGCCAAGAT TTGCCCTGGA GAAAACCAAG CAGCAGAAGA TGAACTCAGA AAAGAGATTA     2160

GTAAATCGAT GTTTGCAGAG ATGGAGATCT TGGGTCAGTT TAACCTGGGA TTTATAGTAA     2220

CCAAACTGAA AGAGGACCTC TTCCTGGTGG ACCAGCATGC TGCGGATGAG AAGTACAACT     2280

TTGAGATGCT GCAGCAGCAC ACGGTGCTCC AGGCGCAGAG GCTCATCACG TGGGTGCACA     2340

CAGGCTTCAG AGTTCCCAGA CCCCAGACTC TGAACTTAAC TGCTGTCAAT GAAGCTGTAC     2400

TGATAGAAAA TCTGGAAATA TTCAGAAAGA ATGGCTTTGA CTTTGTCATT GATGAGGATG     2460

CTCCAGTCAC TGAAAGGGCT AAATTGATTT CCTTACCAAC TAGTAAAAAC TGGACCTTTG     2520

GACCCCAAGA TATAGATGAA CTGATCTTTA TGTTAAGTGA CAGCCCTGGG GTCATGTGCC     2580

GGCCCTCACG AGTCAGACAG ATGTTTGCTT CCAGAGCCTG TCGGAAGTCA GTGATGATTG     2640

GAACGGCGCT CAATGCGAGC GAGATGAAGA AGCTCATCAC CCACATGGGT GAGATGGACC     2700

ACCCCTGGAA CTGCCCCCAC GGCAGGCCAA CCATGAGGCA CGTTGCCAAT CTGGATGTCA     2760

TCTCTCAGAA CTGACACACC CCTTGTAGCA TAGAGTTTAT TACAGATTGT TCGGTTCGCA     2820

AAGAGAAGGT TTTAAGTAAT CTGATTATCG TTGTACAAAA ATTAGCATGC TGCTTTAATG     2880

TACTGGATCC ATTTAAAAGC AGTGTTAAGG CAGGCATGAT GGAGTGTTCC TCTAGCTCAG     2940

CTACTTGGGT GATCCGGTGG GAGCTCATGT GAGCCCAGGA CTTTGAGACC ACTCCGAGCC     3000

ACATTCATGA GACTCAATTC AAGGACAAAA AAAAAAGAT ATTTTTGAAG CCTTTTAAAA      3060
```

AAAAA                                                                3065

(2) INFORMATION FOR SEQ ID NO:29:

(i) SEQUENCE CHARACTERISTICS:
        (A) LENGTH: 864 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:29:

```
Met Glu Gln Thr Glu Gly Val Ser Thr Glu Cys Ala Lys Ala Ile Lys
1               5                   10                  15

Pro Ile Asp Gly Lys Ser Val His Gln Ile Cys Ser Gly Gln Val Ile
            20                  25                  30

Leu Ser Leu Ser Thr Ala Val Lys Glu Leu Ile Glu Asn Ser Val Asp
        35                  40                  45

Ala Gly Ala Thr Thr Ile Asp Leu Arg Leu Lys Asp Tyr Gly Val Asp
50                  55                  60

Leu Ile Glu Val Ser Asp Asn Gly Cys Gly Val Glu Glu Asn Phe
65                  70                  75                  80

Glu Gly Leu Ala Leu Lys His His Thr Ser Lys Ile Gln Glu Phe Ala
                85                  90                  95

Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Gly Ser
        115                 120                 125

Ala Ser Val Gly Thr Arg Leu Val Phe Asp His Asn Gly Lys Ile Thr
    130                 135                 140

Gln Lys Thr Pro Tyr Pro Arg Pro Lys Gly Thr Thr Val Ser Val Gln
145                 150                 155                 160

His Leu Phe Tyr Thr Leu Pro Val Arg Tyr Lys Glu Phe Gln Arg Asn
                165                 170                 175

Ile Lys Lys Glu Tyr Ser Lys Met Val Gln Val Leu Gln Ala Tyr Cys
            180                 185                 190

Ile Ile Ser Ala Gly Val Arg Val Ser Cys Thr Asn Gln Leu Gly Gln
        195                 200                 205

Gly Lys Arg His Ala Val Val Cys Thr Ser Gly Thr Ser Gly Met Lys
    210                 215                 220

Glu Asn Ile Gly Ser Val Phe Gly Gln Lys Gln Leu Gln Ser Leu Ile
225                 230                 235                 240

Pro Phe Val Gln Leu Pro Pro Ser Asp Ala Val Cys Glu Glu Tyr Gly
                245                 250                 255

Leu Ser Thr Ser Gly Arg His Lys Thr Phe Ser Thr Phe Ser Gly Phe
            260                 265                 270

Ile Ser Gln Cys Thr His Gly Ala Gly Arg Ser Ala Thr Asp Arg Gln
        275                 280                 285

Phe Phe Phe Ile Asn Gln Arg Pro Cys Asp Pro Ala Lys Val Ser Lys
    290                 295                 300

Leu Val Asn Glu Val Tyr His Met Tyr Asn Arg His Gln Tyr Pro Phe
305                 310                 315                 320

Val Val Leu Asn Val Ser Val Asp Ser Glu Cys Val Asp Ile Asn Val
                325                 330                 335

Thr Pro Asp Lys Arg Gln Ile Leu Leu Gln Glu Glu Lys Leu Leu Leu
```

```
                          340                 345                 350
        Ala Val Leu Lys Thr Ser Leu Ile Gly Met Phe Asp Ser Asp Ala Asn
                        355                 360                 365

Lys Leu Asn Val Asn Gln Gln Pro Leu Leu Asp Val Glu Gly Asn Leu
                        370                 375                 380

Val Lys Ser His Thr Ala Glu Leu Glu Lys Pro Val Pro Gly Lys Gln
        385                 390                 395                 400

Asp Asn Ser Pro Ser Leu Lys Ser Thr Ala Asp Glu Lys Arg Val Ala
                        405                 410                 415

Ser Ile Ser Arg Leu Arg Glu Ala Phe Ser Leu His Pro Thr Lys Glu
                        420                 425                 430

Ile Lys Ser Arg Gly Pro Glu Thr Ala Glu Leu Thr Arg Ser Phe Pro
                        435                 440                 445

Ser Glu Lys Arg Gly Val Leu Ser Ser Tyr Pro Ser Asp Val Ile Ser
                        450                 455                 460

Tyr Arg Gly Leu Arg Gly Ser Gln Asp Lys Leu Val Ser Pro Thr Asp
        465                 470                 475                 480

Ser Pro Gly Asp Cys Met Asp Arg Glu Lys Ile Glu Lys Asp Ser Gly
                        485                 490                 495

Leu Ser Ser Thr Ser Ala Gly Ser Glu Glu Glu Phe Ser Thr Pro Glu
                        500                 505                 510

Val Ala Ser Ser Phe Ser Ser Asp Tyr Asn Val Ser Ser Leu Glu Asp
                        515                 520                 525

Arg Pro Ser Gln Glu Thr Ile Asn Cys Gly Asp Leu Leu Pro Ser Ser
                        530                 535                 540

Arg Tyr Arg Thr Val Leu Glu Ala Arg Arg Pro Trp Ile Ser Met Gln
        545                 550                 555                 560

Ser Ser Thr Ser Ser Ser Val Thr His Lys Cys Gln Ala Leu Gln
                        565                 570                 575

Asp Arg Gly Arg Pro Ser Asn Val Asn Ile Ser Gln Arg Leu Pro Gly
                        580                 585                 590

Pro Gln Ser Thr Ser Ala Ala Glu Val Asp Val Ala Ile Lys Met Asn
                        595                 600                 605

Lys Arg Ser Cys Ser Ser Ser Leu Ala Lys Arg Met Lys Gln Leu
                        610                 615                 620

Gln His Leu Lys Ala Gln Asn Lys His Glu Leu Ser Tyr Arg Lys Phe
        625                 630                 635                 640

Arg Ala Lys Ile Cys Pro Gly Glu Asn Gln Ala Ala Glu Asp Glu Leu
                        645                 650                 655

Arg Lys Glu Ile Ser Lys Ser Met Phe Ala Glu Met Glu Ile Leu Gly
                        660                 665                 670

Gln Phe Asn Leu Gly Phe Ile Val Thr Lys Leu Lys Glu Asp Leu Phe
                        675                 680                 685

Leu Val Asp Gln His Ala Ala Asp Glu Lys Tyr Asn Phe Glu Met Leu
                        690                 695                 700

Gln Gln His Thr Val Leu Gln Ala Gln Arg Leu Ile Thr Trp Val His
        705                 710                 715                 720

Thr Gly Phe Arg Val Pro Arg Pro Gln Thr Leu Asn Leu Thr Ala Val
                        725                 730                 735

Asn Glu Ala Val Leu Ile Glu Asn Leu Glu Ile Phe Arg Lys Asn Gly
                        740                 745                 750

Phe Asp Phe Val Ile Asp Glu Asp Ala Pro Val Thr Glu Arg Ala Lys
                        755                 760                 765
```

```
Leu Ile Ser Leu Pro Thr Ser Lys Asn Trp Thr Phe Gly Pro Gln Asp
    770                 775                 780

Ile Asp Glu Leu Ile Phe Met Leu Ser Asp Ser Pro Gly Val Met Cys
785                 790                 795                 800

Arg Pro Ser Arg Val Arg Gln Met Phe Ala Ser Arg Ala Cys Arg Lys
                805                 810                 815

Ser Val Met Ile Gly Thr Ala Leu Asn Ala Ser Glu Met Lys Lys Leu
                820                 825                 830

Ile Thr His Met Gly Glu Met Asp His Pro Trp Asn Cys Pro His Gly
            835                 840                 845

Arg Pro Thr Met Arg His Val Ala Asn Leu Asp Val Ile Ser Gln Asn
        850                 855                 860
```

(2) INFORMATION FOR SEQ ID NO:30:

(i) SEQUENCE CHARACTERISTICS:
        (A) LENGTH: 862 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:30:

```
Met Glu Arg Ala Glu Ser Ser Thr Glu Pro Ala Lys Ala Ile Lys
1               5                   10                  15

Pro Ile Asp Arg Lys Ser Val His Gln Ile Cys Ser Gly Gln Val Val
                20                  25                  30

Leu Ser Leu Ser Thr Ala Val Lys Glu Leu Val Glu Asn Ser Leu Asp
            35                  40                  45

Ala Gly Ala Thr Asn Ile Asp Leu Lys Leu Lys Asp Tyr Gly Val Asp
50                  55                  60

Leu Ile Glu Val Ser Asp Asn Gly Cys Gly Val Glu Glu Glu Asn Phe
65                  70                  75                  80

Glu Gly Leu Thr Leu Lys His His Thr Ser Lys Ile Gln Glu Phe Ala
                85                  90                  95

Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Ala Ser
            115                 120                 125

Ala Lys Val Gly Thr Arg Leu Met Phe Asp His Asn Gly Lys Ile Ile
130                 135                 140

Gln Lys Thr Pro Tyr Pro Arg Pro Arg Gly Thr Thr Val Ser Val Gln
145                 150                 155                 160

Gln Leu Phe Ser Thr Leu Pro Val Arg His Lys Glu Phe Gln Arg Asn
                165                 170                 175

Ile Lys Lys Glu Tyr Ala Lys Met Val Gln Val Leu His Ala Tyr Cys
            180                 185                 190

Ile Ile Ser Ala Gly Ile Arg Val Ser Cys Thr Asn Gln Leu Gly Gln
            195                 200                 205

Gly Lys Arg Gln Pro Val Val Cys Thr Gly Gly Ser Pro Ser Ile Lys
210                 215                 220

Glu Asn Ile Gly Ser Val Phe Gly Gln Lys Gln Leu Gln Ser Leu Ile
225                 230                 235                 240

Pro Phe Val Gln Leu Pro Pro Ser Asp Ser Val Cys Glu Glu Tyr Gly
                245                 250                 255

Leu Ser Cys Ser Asp Ala Leu His Asn Leu Phe Tyr Ile Ser Gly Phe
```

```
              260                 265                 270
Ile Ser Gln Cys Thr His Gly Val Gly Arg Ser Ser Thr Asp Arg Gln
            275                 280                 285

Phe Phe Phe Ile Asn Arg Arg Pro Cys Asp Pro Ala Lys Val Cys Arg
            290                 295                 300

Leu Val Asn Glu Val Tyr His Met Tyr Asn Arg His Gln Tyr Pro Phe
305                 310                 315                 320

Val Val Leu Asn Ile Ser Val Asp Ser Glu Cys Val Asp Ile Asn Val
                325                 330                 335

Thr Pro Asp Lys Arg Gln Ile Leu Leu Gln Glu Lys Leu Leu Leu
                340                 345                 350

Ala Val Leu Lys Thr Ser Leu Ile Gly Met Phe Asp Ser Asp Val Asn
                355                 360                 365

Lys Leu Asn Val Ser Gln Gln Pro Leu Leu Asp Val Glu Gly Asn Leu
370                 375                 380

Ile Lys Met His Ala Ala Asp Leu Glu Lys Pro Met Val Glu Lys Gln
385                 390                 395                 400

Asp Gln Ser Pro Ser Leu Arg Thr Gly Glu Glu Lys Lys Asp Val Ser
                405                 410                 415

Ile Ser Arg Leu Arg Glu Ala Phe Ser Leu Arg His Thr Thr Glu Asn
                420                 425                 430

Lys Pro His Ser Pro Lys Thr Pro Glu Pro Arg Arg Ser Pro Leu Gly
                435                 440                 445

Gln Lys Arg Gly Met Leu Ser Ser Thr Ser Gly Ala Ile Ser Asp
                450                 455                 460

Lys Gly Val Leu Arg Ser Gln Lys Glu Ala Val Ser Ser Ser His Gly
465                 470                 475                 480

Pro Ser Asp Pro Thr Asp Arg Ala Glu Val Glu Lys Asp Ser Gly His
                485                 490                 495

Gly Ser Thr Ser Val Asp Ser Glu Gly Phe Ser Ile Pro Asp Thr Gly
                500                 505                 510

Ser His Cys Ser Ser Glu Tyr Ala Ala Ser Ser Pro Gly Asp Arg Gly
                515                 520                 525

Ser Gln Glu His Val Asp Ser Gln Glu Lys Ala Pro Glu Thr Asp Asp
                530                 535                 540

Ser Phe Ser Asp Val Asp Cys His Ser Asn Gln Glu Asp Thr Gly Cys
545                 550                 555                 560

Lys Phe Arg Val Leu Pro Gln Pro Thr Asn Leu Ala Thr Pro Asn Thr
                565                 570                 575

Lys Arg Phe Lys Lys Glu Glu Ile Leu Ser Ser Asp Ile Cys Gln
                580                 585                 590

Lys Leu Val Asn Thr Gln Asp Met Ser Ala Ser Gln Val Asp Val Ala
                595                 600                 605

Val Lys Ile Asn Lys Lys Val Val Pro Leu Asp Phe Ser Met Ser Ser
610                 615                 620

Leu Ala Lys Arg Ile Lys Gln Leu His His Glu Ala Gln Ser Glu
625                 630                 635                 640

Gly Glu Gln Asn Tyr Arg Lys Phe Arg Ala Lys Ile Cys Pro Gly Glu
                645                 650                 655

Asn Gln Ala Ala Glu Asp Glu Leu Arg Lys Glu Ile Ser Lys Thr Met
                660                 665                 670

Phe Ala Glu Met Glu Ile Ile Gly Gln Phe Asn Leu Gly Phe Ile Ile
                675                 680                 685
```

```
Thr Lys Leu Asn Glu Asp Ile Phe Ile Val Asp Gln His Ala Thr Asp
    690             695             700
Glu Lys Tyr Asn Phe Glu Met Leu Gln Gln His Thr Val Leu Gln Gly
705             710             715             720
Gln Arg Leu Ile Ala Pro Gln Thr Leu Asn Leu Thr Ala Val Asn Glu
            725             730             735
Ala Val Leu Ile Glu Asn Leu Glu Ile Phe Arg Lys Asn Gly Phe Asp
            740             745             750
Phe Val Ile Asp Glu Asn Ala Pro Val Thr Glu Arg Ala Lys Leu Ile
            755             760             765
Ser Leu Pro Thr Ser Lys Asn Trp Thr Phe Gly Pro Gln Asp Val Asp
    770             775             780
Glu Leu Ile Phe Met Leu Ser Asp Ser Pro Gly Val Met Cys Arg Pro
785             790             795             800
Ser Arg Val Lys Gln Met Phe Ala Ser Arg Ala Cys Arg Lys Ser Val
            805             810             815
Met Ile Gly Thr Ala Leu Asn Thr Ser Glu Met Lys Lys Leu Ile Thr
            820             825             830
His Met Gly Glu Met Gly His Pro Trp Asn Cys Pro His Gly Arg Pro
            835             840             845
Thr Met Arg His Ile Ala Asn Leu Gly Val Ile Ser Gln Asn
850             855             860
```